US008101775B2

(12) United States Patent  
Ahmed et al.

(10) Patent No.: US 8,101,775 B2
(45) Date of Patent: Jan. 24, 2012

(54) INDOLE DERIVATIVES AS S1P1 RECEPTOR

(75) Inventors: Mahmood Ahmed, Singapore (SG); James Myatt, Harlow (GB); David Norton, Harlow (GB); Dean Andrew Rivers, Singapore (SB)

(73) Assignee: Glaxo Group Limited, Middlesex (GB)

( * ) Notice: Subject to any disclaimer, the term of this patent is extended or adjusted under 35 U.S.C. 154(b) by 0 days.

(21) Appl. No.: 12/520,145

(22) PCT Filed: Dec. 19, 2007

(86) PCT No.: PCT/EP2007/064185
§ 371 (c)(1),
(2), (4) Date: Dec. 10, 2009

(87) PCT Pub. No.: WO2008/074821
PCT Pub. Date: Jun. 26, 2008

(65) Prior Publication Data
US 2010/0113796 A1  May 6, 2010

(30) Foreign Application Priority Data

Dec. 21, 2006  (GB) .................................... 0625647.3
Apr. 19, 2007  (GB) .................................... 0707615.1

(51) Int. Cl.
*A61K 31/443* (2006.01)
*A61K 31/405* (2006.01)
*A61K 31/4245* (2006.01)
*C07D 271/06* (2006.01)
*C07D 209/04* (2006.01)
*C07D 413/14* (2006.01)

(52) U.S. Cl. ........ 548/131; 514/364; 514/339; 514/340; 514/419; 546/269.4; 546/277.4; 548/494

(58) Field of Classification Search .................. 514/339, 514/340, 364, 419; 546/269.4, 277.4; 548/131, 548/494
See application file for complete search history.

(56) References Cited

U.S. PATENT DOCUMENTS 7,678,820 B2 *  3/2010  Harada et al. ................. 514/364
2010/0113528 A1  5/2010  Ahmed et al.

FOREIGN PATENT DOCUMENTS

| JP | 2007 262009 A | 10/2007 |
|---|---|---|
| WO | WO-97/44333 A1 | 11/1997 |
| WO | WO-98/17652 A1 | 4/1998 |
| WO | WO-03/105771 A | 12/2003 |
| WO | WO-2004/101556 A1 | 11/2004 |
| WO | WO 2004/103279 A | 12/2004 |
| WO | WO 2005/032465 A | 4/2005 |
| WO | WO 2006/001463 | 1/2006 |
| WO | WO-2007/085451 A2 | 8/2007 |
| WO | WO 2007/116866 A | 10/2007 |
| WO | WO 2007116866 A1 * | 10/2007 |
| WO | WO-2008/029371 A1 | 3/2008 |
| WO | WO-2008/074821 A1 | 6/2008 |

OTHER PUBLICATIONS

Application No.: 08 736 315.6-2101 EP, Communication pursuant to Article 94(3) EPC, Feb 11, 2010.
Application No.: 08 736 315.6-2101 EP, Response to communication under Rule 94(3) EPC dated Jun. 8, 2010.
Application No. 08 736 315.6-2101 EP, Communication under Rule 71(3) EPC, dated Sep. 27, 2010.
Application No. 08736315.6; Decision to Grant a European Patent Pursuant to Article 97(1) EPC dated Feb. 3, 2011.
Application No. 07857804.4-2101 EP, Decision to Grant a European patent pursuant to Article 97(1) EPC dated Aug 26, 2010.
Application No. 07857804.4-2101 EP, Communication under Rule 71(3) EPC dated May 3, 2010.
Application No. 07857804.4-2101 EP, Response to Communication under Rule 94(3) EPC dated Mar. 17, 2010.
Application No. 07857804.7-2101 EP, Communication pursuant to Article 94(3) EPC; dated Sep. 23, 2009.
Application No. 07857804.4; Response to Communication to Rule 71(3) EPC; dated Aug. 9, 2010.
Application No. 10158582.6 EP, Letter requesting further processing; Feb. 24, 2011.
Application No. 10158582.6 EP, Communication pursuant to Article 94(3) EPC Mar. 31, 2011.
Application No. 07857808.May 2101 EP, Communication pursuant to Article 94(3) EPC; Nov 16, 2009.
Application No. 07857808.5-2101 EP, Response to Communication under Rule 94(3) EPC; Mar. 15, 2010.
Application No. 07857808.5-2101 EP, Communication pursuant to Article 94(3) EPC; Jul. 14, 2010.

(Continued)

*Primary Examiner* — Yong Chu
(74) *Attorney, Agent, or Firm* — Linda E. Hall; John L. Lemanowicz

(57) ABSTRACT

The invention relates to compounds of formula (I)

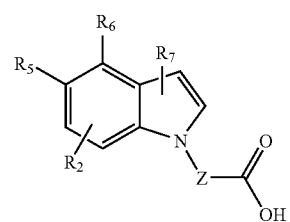

(I)

wherein
one of $R_5$ and $R_6$ is hydrogen or $R_2$ and the other is (a)

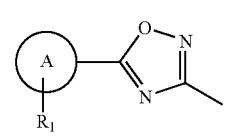

(a)

pharmaceutical compositions containing them and their use in the treatment of conditions or disorders which are mediated via the S1P1 receptor.

4 Claims, No Drawings

OTHER PUBLICATIONS

Application No. 07857808.5-2101 EP, Response to communication under Rule 94(3) EPC; Nov. 8, 2010.

Application No. 07857808.5-2101 EP, Communication under Rule 71(3) EPC; Dec. 30, 2010.

Application No. 07857808.5-2101 EP, Response to communication pursuant to Rule 71(3) EPC; Apr. 7, 2011.

Application No. 07857808.5-2101 EP, Decision to grant a European patent pursuant to Article 97(1) EPC; Apr. 21, 2011.

* cited by examiner

INDOLE DERIVATIVES AS S1P1 RECEPTOR

This application is a 371 of International Application No. PCT/EP2007/064185, filed 19-Dec.-2009, which claims the priority of GB 0625647.3, filed 21-Dec.-2006, and GB 0707615.1, filed 19-Apr. 2007, which are incorporated herein in their entirety.

The present invention relates to novel oxadiazole derivatives having pharmacological activity, processes for their preparation, pharmaceutical compositions containing them and their use in the treatment of various disorders.

Sphingosine 1-phosphate (S1P) is a bioactive lipid mediator formed by the phosphorylation of sphingosine by sphingosine kinases and is found in high levels in the blood. It is produced and secreted by a number of cell types, including those of hematopoietic origin such as platelets and mast cells (Okamoto et al 1998 J Biol Chem 273(42):27104; Sanchez and Hla 2004, J Cell Biochem 92:913). It has a wide range of biological actions, including regulation of cell proliferation, differentiation, motility, vascularisation, and activation of inflammatory cells and platelets (Pyne and Pyne 2000, Biochem J. 349: 385). Five subtypes of S1P responsive receptor have been described, S1P1 (Edg-1), S1P2 (Edg-5), S1P3 (Edg-3), S1P4 (Edg-6), and S1P5 (Edg-8), forming part of the G-protein coupled endothelial differentiation gene family of receptors (Chun et al 2002 Pharmacological Reviews 54:265, Sanchez and Hla 2004 J Cellular Biochemistry, 92:913). These 5 receptors show differential mRNA expression, with S1P1-3 being widely expressed, S1P4 expressed on lymphoid and hematopoietic tissues and S1P5 primarily in brain and to a lower degree in spleen. They signal via different subsets of G proteins to promote a variety of biological responses (Kluk and Hla 2002 Biochem et Biophysica Acta 1582:72, Sanchez and Hla 2004, J Cellular Biochem 92:913).

Proposed roles for the S1P1 receptor include lymphocyte trafficking, cytokine induction/suppression and effects on endothelial cells (Rosen and Goetzl 2005 Nat Rev Immunol. 5:560). Agonists of the S1P1 receptor have been used in a number of autoimmune and transplantation animal models, including Experimental Autoimmune Encephalomelitis (EAE) models of MS, to reduce the severity of the induced disease (Brinkman et al 2003 JBC 277:21453; Fujino et al 2003 J Pharmacol Exp Ther 305:70; Webb et al 2004 J Neuroimmunol 153:108; Rausch et al 2004 J Magn Reson Imaging 20:16). This activity is reported to be mediated by the effect of S1P1 agonists on lymphocyte circulation through the lymph system. Treatment with S1P1 agonists results in the sequestration of lymphocytes within secondary lymphoid organs such as the lymph nodes, inducing a reversible peripheral lymphopoenia in animal models (Chiba et al 1998, J Immunology 160:5037, Forrest et al 2004 J Pharmacol Exp Ther 309:758; Sanna et al 2004 JBC 279:13839). Published data on agonists suggests that compound treatment induces loss of the S1P1 receptor from the cell surface via internalisation (Graler and Goetzl 2004 FASEB J 18:551; Matloubian et al 2004 Nature 427:355; Jo et al 2005 Chem Biol 12:703) and it is this reduction of S1P1 receptor on immune cells which contributes to the reduction of movement of T cells from the lymph nodes back into the blood stream.

S1P1 gene deletion causes embryonic lethality. Experiments to examine the role of the S1P1 receptor in lymphocyte migration and trafficking have included the adoptive transfer of labelled S1P1 deficient T cells into irradiated wild type mice. These cells showed a reduced egress from secondary lymphoid organs (Matloubian et al 2004 Nature 427:355).

S1P1 has also been ascribed a role in endothelial cell junction modulation (Allende et al 2003 102:3665, Blood Singelton et al 2005 FASEB J 19:1646). With respect to this endothelial action, S1P1 agonists have been reported to have an effect on isolated lymph nodes which may be contributing to a role in modulating immune disorders. S1P1 agonists caused a closing of the endothelial stromal 'gates' of lymphatic sinuses which drain the lymph nodes and prevent lymphocyte egress (Wei wt al 2005, Nat. Immunology 6:1228).

The immunosuppressive compound FTY720 (JP11080026-A) has been shown to reduce circulating lymphocytes in animals and man, have disease modulating activity in animal models of immune disorders and reduce remission rates in relapsing remitting Multiple Sclerosis (Brinkman et al 2002 JBC 277:21453, Mandala et al 2002 Science 296:346, Fujino et al 2003 J Pharmacology and Experimental Therapeutics 305:45658, Brinkman et al 2004 American J Transplantation 4:1019, Webb et al 2004 J Neuroimmunology 153:108, Morris et al 2005 Eur J Immunol 35:3570, Chiba 2005 Pharmacology and Therapeutics 108: 308, Kahan et al 2003, Transplantation 76:1079, Kappos et al 2006 New Eng J Medicine 335:1124). This compound is a prodrug that is phosphorylated in vivo by sphingosine kinases to give a molecule that has agonist activity at the S1P1, S1P3, S1P4 and S1P5 receptors. Clinical studies have demonstrated that treatment with FTY720 results in bradycardia in the first 24 hours of treatment (Kappos et al 2006 New Eng J Medicine 335:1124). The bradycardia is thought to be due to agonism at the S1P3 receptor, based on a number of cell based and animal experiments. These include the use of S1P3 knock-out animals which, unlike wild type mice, do not demonstrate bradycardia following FTY720 administration and the use of S1P1 selective compounds. (Hale et al 2004 Bioorganic & Medicinal Chemistry Letters 14:3501, Sanna et al 2004 JBC 279: 13839, Koyrakh et al 2005 American J Transplantation 5:529)

Hence, there is a need for S1P1 receptor agonist compounds with selectivity over S1P3 which might be expected to show a reduced tendency to induce bradycardia.

The following patent applications describe oxadiazole derivatives as S1P1 agonists: WO03/105771, WO05/058848, WO06/047195, WO06/100633, WO06/115188, WO06/131336, WO07/024,922 and WO07/116,866.

The following patent application describes indole-oxadiazole derivatives as antipicornaviral agents: WO96/009822. The following patent applications describe indole-carboxylic acid derivatives as leukotriene receptor antagonists, pesticides and agrochemical fungicides respectively: WO06/090817, EP 0 439 785 and DE 39 39 238.

A structurally novel class of compounds has now been found which provides agonists of the S1P1 receptor.

The present invention therefore provides compounds of formula (I) or a pharmaceutically acceptable salt thereof thereof:

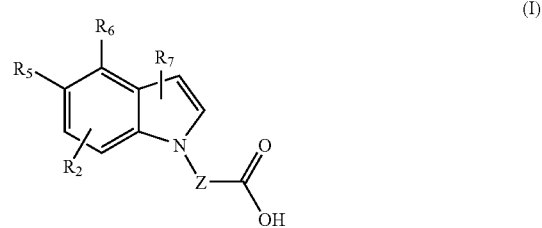

wherein
one of $R_5$ and $R_6$ is hydrogen or $R_2$ and the other is (a)

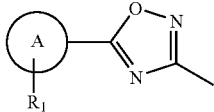

A is a phenyl or a 5 or 6-membered heteroaryl ring;
$R_1$ is hydrogen or up to three substituents independently selected from halogen, $C_{(1-6)}$alkyl, $C_{(3-6)}$cycloalkyl, $C_{(1-6)}$alkoxy, $C_{(3-6)}$cycloalkyloxy, trifluoromethoxy, difluoromethoxy, trifluoromethyl, cyano, nitro, optionally substituted piperidine, optionally substituted pyrrolidine, optionally substituted phenyl and optionally substituted 5 or 6 membered heteroaryl rings;
when $R_1$ is phenyl, piperidine, pyrrolidine or a 5 or 6 membered heteroaryl ring it may be substituted by up to three substituents selected from halogen, $C_{(1-6)}$alkyl, $C_{(1-6)}$alkoxy, trifluoromethoxy, difluoromethoxy, $C_{3-6}$cycloalkyl, trifluoromethyl and cyano;
$R_2$ is hydrogen or up to three substituents independently selected from halogen, $C_{(1-4)}$alkyl, $C_{(1-4)}$alkoxy, trifluoromethoxy, difluoromethoxy, trifluoromethyl and cyano;
$R_7$ is hydrogen or halogen;
Z is $C_{(1-4)}$alkyl which is optionally interrupted by N or O and is optionally substituted by halogen or methyl.

In one embodiment, when A is phenyl or pyridyl $R_1$ is two substituents at the para and meta positions on A relative to the oxadiazole ring.

In one embodiment, when A is thienyl $R_1$ is two substituents at the 4- and 5-positions.

In one embodiment of the invention,
$R_5$ is hydrogen and $R_6$ is (a); and/or
A is thienyl, pyridyl or phenyl; and/or
$R_1$ is up to three substituents selected from halogen, $C_{1-6}$alkoxy, or trifluoromethyl, optionally substituted phenyl, optionally substituted cyclohexyl, cyano, trifluoromethoxy, optionally substituted piperidine, optionally substituted pyrrolidine, $C_{1-6}$alkyl and $NO_2$; and/or
$R_2$ is hydrogen; and/or
$R_7$ is hydrogen or halogen; and/or
Z is $C_{(1-4)}$alkyl which is optionally interrupted by N or O and is optionally substituted by fluoro or methyl.

In one embodiment of the invention,
$R_5$ is hydrogen and $R_6$ is (a); and/or
A is pyridyl or phenyl; and/or
$R_1$ is up to two substituents selected from halogen, $C_{1-6}$alkoxy, or trifluoromethyl, optionally substituted phenyl, optionally substituted cyclohexyl, cyano, trifluoromethoxy, optionally substituted piperidine, optionally substituted pyrrolidine, $C_{1-6}$alkyl and $NO_2$; and/or
$R_2$ is hydrogen; and/or
$R_7$ is hydrogen, chloro or bromo; and/or
Z is unsubstituted $C_{(2-3)}$alkyl.

In one embodiment of the invention,
$R_5$ is hydrogen and $R_6$ is (a); and/or
A is pyridyl or phenyl; and/or
$R_1$ is up to two substituents selected from chloro, bromo, methoxy, propoxy, isopropoxy, trifluoromethyl, halo substituted phenyl, phenyl, cyclohexyl, cyano, trifluoromethoxy, piperidine, pyrrolidine, ethyl or $NO_2$.; and/or
$R_2$ is hydrogen; and/or
$R_7$ is hydrogen, chloro or bromo; and/or Z is unsubstituted $C_{(2-3)}$alkyl.

In one embodiment of the invention,
$R_5$ is hydrogen and $R_6$ is (a); and/or
A is pyridyl or phenyl; and/or
$R_1$ is up to two substituents selected from chloro, isopropoxy and cyano; and/or
$R_2$ is hydrogen; and/or
$R_7$ is hydrogen; and/or
Z is unsubstituted $C_{(2-3)}$alkyl.

In one embodiment of the invention,
$R_5$ is (a) and $R_6$ is hydrogen.
A is optionally substituted thiophene or phenyl; and/or
$R_1$ is hydrogen, halogen, $C_{1-4}$alkoxy, or trifluoromethyl; and/or
$R_2$ is hydrogen; and/or
Z is ethylene.

In another embodiment of the invention,
$R_5$ is (a) and $R_6$ is hydrogen; and/or
A is thiophene substituted by phenyl; and/or
$R_1$ is hydrogen, halogen, $C_{1-4}$alkoxy, or trifluoromethyl; and/or
$R_2$ is hydrogen; and/or
Z is ethylene.

When $R_1$ is phenyl or a 5 or 6 membered heteroaryl ring it may be substituted by up to three substituents selected from halogen, $C_{(1-4)}$alkyl, $C_{(1-4)}$alkoxy, trifluoromethoxy, difluoromethoxy, trifluoromethyl and cyano.

The present invention therefore also provides compounds of formula (IA) or a pharmaceutically acceptable salt thereof:

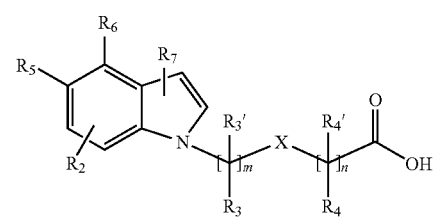

(IA)

wherein:
one of $R_5$ and $R_6$ is hydrogen or $R_2$ and the other is (a)

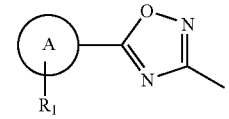

(a)

A is a phenyl or a 5 or 6-membered heteroaryl ring;
$R_1$ is hydrogen or up to three substituents independently selected from halogen, $C_{(1-4)}$alkyl, $C_{(1-4)}$alkoxy, trifluoromethoxy, difluoromethoxy, trifluoromethyl, cyano, optionally substituted phenyl and optionally substituted 5 or 6 membered heteroaryl rings;
$R_2$ is hydrogen or up to three substituents independently selected from halogen, $C_{(1-4)}$alkyl, $C_{(1-4)}$alkoxy, trifluoromethoxy, difluoromethoxy, trifluoromethyl and cyano;
$R_3$, $R_{3'}$, $R_4$ and $R_{4'}$ are each independently selected from hydrogen, halogen and methyl;
$R_7$ is hydrogen or halogen;
X is NH optionally substituted by methyl, O, $CH_2$ optionally substituted by fluoro or methyl, or a direct bond;
m is 0-2; and
n is 0-4.

When $R_1$ is phenyl or a 5 or 6 membered heteroaryl ring it may be substituted by up to three substituents selected from halogen, $C_{(1-4)}$alkyl, $C_{(1-4)}$alkoxy, trifluoromethoxy, difluoromethoxy, trifluoromethyl and cyano.

When X is NH it may be substituted by methyl.

When X is $CH_2$ it may be substituted by fluoro or methyl.

In one embodiment of the invention,

A is optionally substituted thiophene or phenyl;
$R_1$ is hydrogen, halogen, $C_{1-4}$alkoxy, or trifluoromethyl;
$R_2$, $R_3$ and $R_4$ are each hydrogen;
X is a direct bond;
m is 2; and
n is 0.

In another embodiment of the invention,

A is thiophene substituted by phenyl;
$R_1$ is hydrogen, halogen, $C_{1-4}$alkoxy, or trifluoromethyl;
$R_2$, $R_3$ and $R_4$ are each hydrogen;
X is a direct bond;
m is 2; and
n is 0

The term "alkyl" as a group or part of a group e.g. alkoxy or hydroxyalkyl refers to a straight or branched alkyl group in all isomeric forms. The term "$C_{(1-6)}$alkyl" refers to an alkyl group, as defined above, containing at least 1, and at most 6 carbon atoms Examples of such alkyl groups include methyl, ethyl, propyl, iso-propyl, n-butyl, iso-butyl, sec-butyl, or tert-butyl. Examples of such alkoxy groups include methoxy, ethoxy, propoxy, iso-propoxy, butoxy, iso-butoxy, sec-butoxy and tert-butoxy.

Suitable $C_{(3-6)}$cycloalkyl groups include cyclopropyl, cyclobutyl, cyclopentyl and cyclohexyl.

Suitable $C_{(3-6)}$cycloalkyloxy groups include cyclopropoxy, cyclobutoxy, cyclopentoxy and cyclohexyloxy.

As used herein, the term "halogen" refers to fluorine (F), chlorine (Cl), bromine (Br), or iodine (I) and the term "halo" refers to the halogen: fluoro (-F), chloro (-Cl), bromo (-Br) and iodo (-I).

The term "heteroaryl" represents an unsaturated ring which comprises one or more heteroatoms. When the term heteroaryl represents a 5 membered group it contains a heteroatom selected from O, N or S and may optionally contain a further 1 to 3 nitrogen atoms. When heteroaryl represents a 6-membered group it contains from 1 to 3 nitrogen atoms. Examples of such 5 or 6 membered heteroaryl rings include pyrrolyl, triazolyl, thiadiazolyl, tetrazolyl, imidazolyl, pyrazolyl, isothiazolyl, thiazolyl, isoxazolyl, oxazolyl, oxadiazolyl, furazanyl, furanyl, thienyl, pyridyl, pyrimidinyl, pyrazinyl, pyridazinyl and triazinyl.

In certain of the compounds of formula (I), dependent upon the nature of the substituent there are chiral carbon atoms and therefore compounds of formula (I) may exist as stereoisomers. The invention extends to all optical isomers such as stereoisomeric forms of the compounds of formula (I) including enantiomers, diastereoisomers and mixtures thereof, such as racemates. The different stereoisomeric forms may be separated or resolved one from the other by conventional methods or any given isomer may be obtained by conventional stereoselective or asymmetric syntheses.

Certain of the compounds herein can exist in various tautomeric forms and it is to be understood that the invention encompasses all such tautomeric forms.

Suitable compounds of the invention are:

3-(5-{5-[4-phenyl-5-(trifluoromethyl)-2-thienyl]-1,2,4-oxadiazol-3-yl}-1H-indol-1-yl)propanoic acid
3-[5-(5-{3-Chloro-4-[(1-methylethyl)oxy]phenyl}-1,2,4-oxadiazol-3-yl)-1H-indol-1-yl]propanoic acid
3-[3-Chloro-5-(5-{3-chloro-4-[(1-methylethyl)oxy]phenyl}-1,2,4-oxadiazol-3-yl)-1H-indol-1-yl]propanoic acid
3-(3-Chloro-5-{5-[4-phenyl-5-(trifluoromethyl)-2-thienyl]-1,2,4-oxadiazol-3-yl}-1H-indol-1-yl)propanoic acid
3-(4-{5-[4-Phenyl-5-(trifluoromethyl)-2-thienyl]-1,2,4-oxadiazol-3-yl}-1H-indol-1-yl)propanoic acid
3-[4-(5-{3-Chloro-4-[(trifluoromethyl)oxy]phenyl}-1,2,4-oxadiazol-3-yl)-1H-indol-1-yl]propanoic acid
3-[4-(5-{3-Chloro-4-[(1-methylethyl)oxy]phenyl}-1,2,4-oxadiazol-3-yl)-1H-indol-1-yl]propanoic acid
3-[4-(5-{5-Chloro-6-[(1-methylethyl)oxy]-3-pyridinyl}-1,2,4-oxadiazol-3-yl)-1H-indol-1-yl]propanoic acid
3-[5-(5-{3-chloro-4-[(1-methylethyl)oxy]phenyl}-1,2,4-oxadiazol-3-yl)-1H-indol-1-yl]propanoic acid
(5-{5-[4-phenyl-5-(trifluoromethyl)-2-thienyl]-1,2,4-oxadiazol-3-yl}-1H-indol-1-yl)acetic acid
3-[3-bromo-5-(5-{3-chloro-4-[(1-methylethyl)oxy]phenyl}-1,2,4-oxadiazol-3-yl)-1H-indol-1-yl]propanoic acid
5-[5-(5-{3-chloro-4-[(1-methylethyl)oxy]phenyl}-1,2,4-oxadiazol-3-yl)-1H-indol-1-yl]pentanoic acid
4-[5-(5-{3-chloro-4-[(1-methylethyl)oxy]phenyl}-1,2,4-oxadiazol-3-yl)-1H-indol-1-yl]butanoic acid
4-[5-(5-{3-chloro-4-[(1-methylethyl)oxy]phenyl}-1,2,4-oxadiazol-3-yl)-1H-indol-1-yl]butanoic acid
(2S)-3-[5-(5-{3-chloro-4-[(1-methylethyl)oxy]phenyl}-1,2,4-oxadiazol-3-yl)-1H-indol-1-yl]-2-methylpropanoic acid
2,2-dimethyl-3-(5-{5-[4-phenyl-5-(trifluoromethyl)-2-thienyl]-1,2,4-oxadiazol-3-yl}-1H-indol-1-yl)propanoic acid
3-[5-(5-{3-Chloro-4-[(1-methylethyl)oxy]phenyl}-1,2,4-oxadiazol-3-yl)-1H-indol-1-yl]-2,2,3-trifluoropropanoic acid
4-[4-(5-{3-cyano-4-[(1-methylethyl)oxy]phenyl}-1,2,4-oxadiazol-3-yl)-1H-indol-1-yl]butanoic acid
3-[5-(5-{3-cyano-4-[(1-methylethyl)oxy]phenyl}-1,2,4-oxadiazol-3-yl)-1H-indol-1-yl]propanoic acid
3-[4-(5-{3-cyano-4-[(1-methylethyl)oxy]phenyl}-1,2,4-oxadiazol-3-yl)-1H-indol-1-yl]propanoic acid
3-(4-{5-[2-(trifluoromethyl)-4-biphenylyl]-1,2,4-oxadiazol-3-yl}-1H-indol-1-yl)propanoic acid
3-(4-{5-[4-cyclohexyl-3-(trifluoromethyl)phenyl]-1,2,4-oxadiazol-3-yl}-1H-indol-1-yl)propanoic acid
3-(4-{5-[4-[(1-methylethyl)oxy]-3-(trifluoromethyl)phenyl]-1,2,4-oxadiazol-3-yl}-1H-indol-1-yl)propanoic acid
[4-(5-{3-chloro-4-[(1-methylethyl)oxy]phenyl}-1,2,4-oxadiazol-3-yl)-1H-indol-1-yl]acetic acid
[4-(5-{3-cyano-4-[(1-methylethyl)oxy]phenyl}-1,2,4-oxadiazol-3-yl)-1H-indol-1-yl]acetic acid
3-(4-{5-[2'-fluoro-2-(trifluoromethyl)-4-biphenylyl]-1,2,4-oxadiazol-3-yl}-1H-indol-1-yl)propanoic acid
4-[4-(5-{3-chloro-4-[(1-methylethyl)oxy]phenyl}-1,2,4-oxadiazol-3-yl)-1H-indol-1-yl]butanoic acid
4-[4-(5-{3-chloro-4-[(trifluoromethyl)oxy]phenyl}-1,2,4-oxadiazol-3-yl)-1H-indol-1-yl]butanoic acid
4-[4-(5-{5-chloro-6-[(1-methylethyl)oxy]-3-pyridinyl}-1,2,4-oxadiazol-3-yl)-1H-indol-1-yl]butanoic acid
4-(4-{5-[4-phenyl-5-(trifluoromethyl)-2-thienyl]-1,2,4-oxadiazol-3-yl}-1H-indol-1-yl)butanoic acid
4-(4-{5-[2-(trifluoromethyl)-4-biphenylyl]-1,2,4-oxadiazol-3-yl}-1H-indol-1-yl)butanoic acid
3-(4-{5-[4-(methyloxy)-3-(trifluoromethyl)phenyl]-1,2,4-oxadiazol-3-yl}-1H-indol-1-yl)propanoic acid
4-{4-[5-(3-cyano-4-{[(1R)-1-methylpropyl]oxy}phenyl)-1,2,4-oxadiazol-3-yl]-1H-indol-1-yl}butanoic acid
4-{4-[5-(3-cyano-4-{[(1S)-1-methylpropyl]oxy}phenyl)-1,2,4-oxadiazol-3-yl]-1H-indol-1-yl}butanoic acid
3-(4-{5-[3-ethyl-4-(1-piperidinyl)phenyl]-1,2,4-oxadiazol-3-yl}-1H-indol-1-yl)propanoic acid 3-{4-[5-(4-cyclohexyl-3-ethylphenyl)-1,2,4-oxadiazol-3-yl]-1H-indol-1-yl}propanoic acid
3-(4-{5-[5-chloro-6-(1-pyrrolidinyl)-3-pyridinyl]-1,2,4-oxadiazol-3-yl}-1H-indol-1-yl)propanoic acid
4-[4-(5-{3-bromo-4-[(1-methylethyl)oxy]phenyl}-1,2,4-oxadiazol-3-yl)-1H-indol-1-yl]butanoic acid
4-(4-{5-[3-chloro-4-(2-methylpropyl)phenyl]-1,2,4-oxadiazol-3-yl}-1H-indol-1-yl)butanoic acid
3-(4-{5-[4-(2-methylpropyl)-3-(trifluoromethyl)phenyl]-1,2,4-oxadiazol-3-yl}-1H-indol-1-yl)propanoic acid
4-(4-{5-[3-cyano-4-(2-methylpropyl)phenyl]-1,2,4-oxadiazol-3-yl}-1H-indol-1-yl)butanoic acid
4-{4-[5-(2-cyano-4-biphenylyl)-1,2,4-oxadiazol-3-yl]-1H-indol-1-yl}butanoic acid
3-(3-Chloro-4-{5-[4-phenyl-5-(trifluoromethyl)-2-thienyl]-1,2,4-oxadiazol-3-yl}-1H-indol-1-yl)propanoic acid
3-[3-chloro-5-(5-{3-chloro-4-[(trifluoromethyl)oxy]phenyl}-1,2,4-oxadiazol-3-yl)-1H-indol-1-yl]propanoic acid
3-(3-chloro-5-{5-[3-chloro-4-(propyloxy)phenyl]-1,2,4-oxadiazol-3-yl}-1H-indol-1-yl)propanoic acid
3-(3-chloro-5-{5-[3-chloro-4-(methyloxy)phenyl]-1,2,4-oxadiazol-3-yl}-1H-indol-1-yl)propanoic acid
3-(3-chloro-5-{5-[4-(methyloxy)-3-(trifluoromethyl)phenyl]-1,2,4-oxadiazol-3-yl}-1H-indol-1-yl)propanoic acid
3-(3-chloro-5-{5-[3-chloro-4-(ethyloxy)phenyl]-1,2,4-oxadiazol-3-yl}-1H-indol-1-yl)propanoic acid
3-[3-chloro-5-(5-{3-cyano-4-[(1-methylethyl)oxy]phenyl}-1,2,4-oxadiazol-3-yl)-1H-indol-1-yl]propanoic acid
3-(3-chloro-5-{5-[4-nitro-3-(trifluoromethyl)phenyl]-1,2,4-oxadiazol-3-yl}-1H-indol-1-yl)propanoic acid
3-[3-chloro-5-(5-{4-chloro-3-[(1-methylethyl)oxy]phenyl}-1,2,4-oxadiazol-3-yl)-1H-indol-1-yl]propanoic acid
3-(3-chloro-5-{5-[6-(methyloxy)-3-biphenylyl]-1,2,4-oxadiazol-3-yl}-1H-indol-1-yl)propanoic acid
3-(5-{5-[6-(trifluoromethyl)-3-biphenylyl]-1,2,4-oxadiazol-3-yl}-1H-indol-1-yl)propanoic acid
3-{5-[5-(4-phenyl-2-thienyl)-1,2,4-oxadiazol-3-yl]-1H-indol-1-yl}propanoic acid
3-{3-chloro-5-[5-(4-cyclohexylphenyl)-1,2,4-oxadiazol-3-yl]-1H-indol-1-yl}propanoic acid
3-(3-chloro-5-{5-[6-(4-fluorophenyl)-3-pyridinyl]-1,2,4-oxadiazol-3-yl}-1H-indol-1-yl)propanoic acid
3-(3-chloro-5-{5-[6-(4-fluorophenyl)-3-pyridinyl]-1,2,4-oxadiazol-3-yl}-1H-indol-1-yl)propanoic acid
or pharmaceutically acceptable salts thereof.

Pharmaceutically acceptable derivatives of compounds of formula (I) include any pharmaceutically acceptable salt, ester or salt of such ester of a compound of formula (I) which, upon administration to the recipient is capable of providing (directly or indirectly) a compound of formula (I) or an active metabolic or residue thereof.

The compounds of formula (I) can form salts. It will be appreciated that for use in medicine the salts of the compounds of formula (I) should be pharmaceutically acceptable. Suitable pharmaceutically acceptable salts will be apparent to those skilled in the art and include those described in J. Pharm. Sci., 1977, 66, 1-19, such as acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid. Certain of the compounds of formula (I) may form acid addition salts with one or more equivalents of the acid. The present invention includes within its scope all possible stoichiometric and non-stoichiometric forms. Salts may also be prepared from pharmaceutically acceptable bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Salts derived from pharmaceutically acceptable organic bases include salts of primary, secondary, and tertiary amines; substituted amines including naturally occurring substituted amines; and cyclic amines. Particular pharmaceutically acceptable organic bases include arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, procaine, purines, theobromine, triethylamine, trimethylamine, tripropylamine, tris(hydroxymethyl)aminomethane (TRIS, trometamol) and the like. Salts may also be formed from basic ion exchange resins, for example polyamine resins. When the compound of the present invention is basic, salts may be prepared from pharmaceutically acceptable acids, including inorganic and organic acids. Such acids include acetic, benzenesulfonic, benzoic, camphorsulfonic, citric, ethanesulfonic, ethanedisulfonic, fumaric, gluconic, glutamic, hydrobromic, hydrochloric, isethionic, lactic, maleic, malic, mandelic, methanesulfonic, mucic, pamoic, pantothenic, phosphoric, propionic, succinic, sulfuric, tartaric, p-toluenesulfonic acid, and the like.

The compounds of formula (I) may be prepared in crystalline or non-crystalline form, and, if crystalline, may optionally be hydrated or solvated. This invention includes within its scope stoichiometric hydrates or solvates as well as compounds containing variable amounts of water and/or solvent.

Included within the scope of the invention are all salts, solvates, hydrates, complexes, polymorphs, prodrugs, radio-labelled derivatives, stereoisomers and optical isomers of the compounds of formula (I).

In a further aspect, this invention provides processes for the preparation of a compound of formula (I). In one aspect the compound of formula (I) can be prepared by the process in Scheme I where A, Z, $R_1$, $R_2$, $R_7$ are as defined for formula (I).

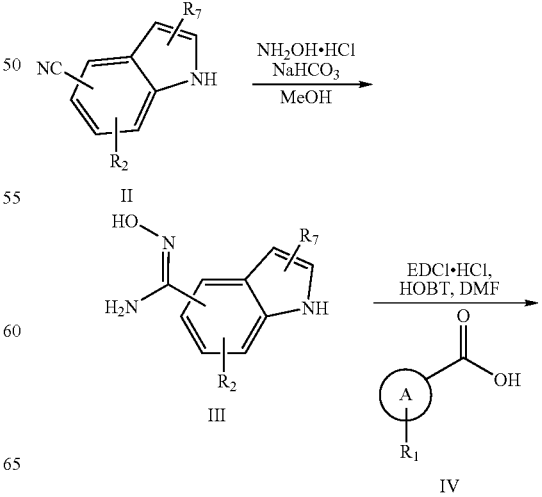

Scheme I

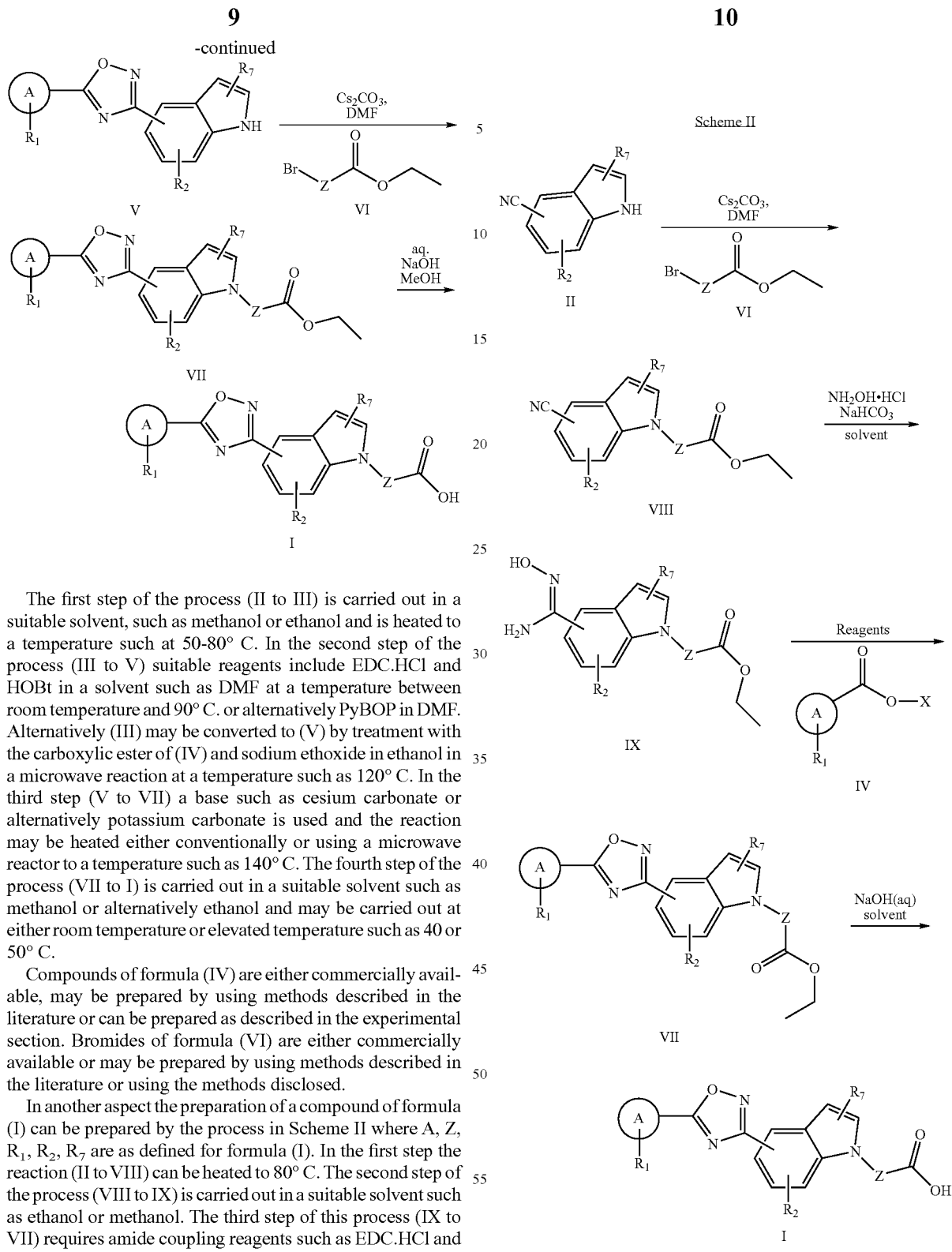

The first step of the process (II to III) is carried out in a suitable solvent, such as methanol or ethanol and is heated to a temperature such at 50-80° C. In the second step of the process (III to V) suitable reagents include EDC.HCl and HOBt in a solvent such as DMF at a temperature between room temperature and 90° C. or alternatively PyBOP in DMF. Alternatively (III) may be converted to (V) by treatment with the carboxylic ester of (IV) and sodium ethoxide in ethanol in a microwave reaction at a temperature such as 120° C. In the third step (V to VII) a base such as cesium carbonate or alternatively potassium carbonate is used and the reaction may be heated either conventionally or using a microwave reactor to a temperature such as 140° C. The fourth step of the process (VII to I) is carried out in a suitable solvent such as methanol or alternatively ethanol and may be carried out at either room temperature or elevated temperature such as 40 or 50° C.

Compounds of formula (IV) are either commercially available, may be prepared by using methods described in the literature or can be prepared as described in the experimental section. Bromides of formula (VI) are either commercially available or may be prepared by using methods described in the literature or using the methods disclosed.

In another aspect the preparation of a compound of formula (I) can be prepared by the process in Scheme II where A, Z, $R_1$, $R_2$, $R_7$ are as defined for formula (I). In the first step the reaction (II to VIII) can be heated to 80° C. The second step of the process (VIII to IX) is carried out in a suitable solvent such as ethanol or methanol. The third step of this process (IX to VII) requires amide coupling reagents such as EDC.HCl and HOBt in a solvent such as DMF at a temperature between room temperature and 120° C. The fourth step of the process is carried out in a suitable solvent such as ethanol or methanol. Compounds of formula (IV) are either commercially available, may be prepared by using methods described in the literature or can be prepared as described in the experimental section. Bromides of formula VI are either commercially available or may be prepared by using methods described in the literature or by the methods disclosed.

In cases where the substituent $R_7$ in formula I is a chlorine atom attached to C-3 of the indole ring this may be introduced in a number of ways. Intermediate (V) in scheme I where $R_7$=H and $R_1$, $R_2$ and A are defined as in formula (I) may be treated with N-chlorosuccinimide in dichloromethane to generate the 3-chloro-compound (Va) which can then be converted to (I) as described in scheme I (Scheme III)

Scheme III

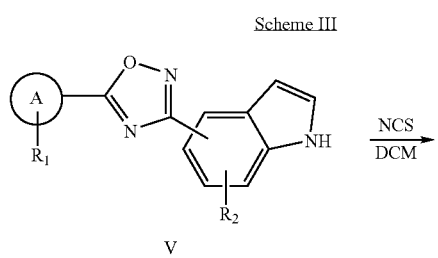

Alternatively, the intermediate (II) where $R_7$=H may be chlorinated by treatment with N-chlorosuccinimide in DMF to generate a 3-chloro-indole (IIa) which can be converted to a compound of structure (I) as described in scheme II (Scheme IV).

Scheme IV

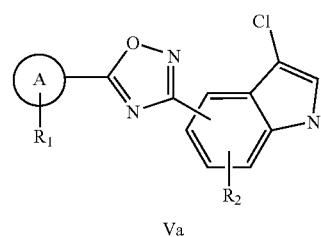

Where $R_7$=Br the intermediate (V) where $R_7$=H and A, $R_1$ and $R_2$ are as defined in formula (I) may be brominated by treatment with $Br_2$ in DMF to generate (Vb) where $R_7$=Br (Scheme V).

Scheme V

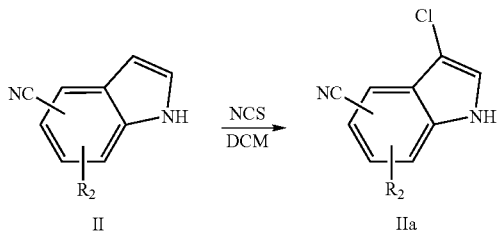

In cases where $R_1$ is a phenyl group it is possible to introduce this group by a cross-coupling reaction on a compound of structure VII to generate VIIa (Scheme VI) where A, Z, $R_2$ and $R_7$ are as defined in formula (I), and Ar is optionally substituted phenyl, followed by hydrolysis to compound I. In this transformation, M is a group such as $B(OH)_2$ which allows the cross-coupling reaction to occur, Y is a group such as bromine, iodine or trifluoromethanesulfonate and the catalyst a palladium species such as tetrakistriphenylphosphine palladium(0). Such reactions are typically carried out at elevated temperature.

Scheme VI

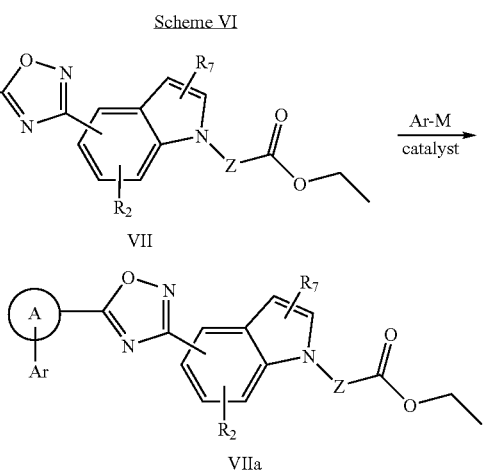

In cases where $R_1$ is an alkoxy group such as O-ethyl or O-isopropyl the alkyl substituent can be introduced into a compound of formula VII where $R_1$=OH and A, Z, $R_7$ and $R_2$ are as defined in formula (I) to generate a compound of formula VIIb where $R_1$=O-alkyl (Scheme VII). In this case Y is a halogen such as iodine. The reaction may be performed in a polar solvent such as DMF in the presence of a base such as potassium carbonate.

Scheme VII

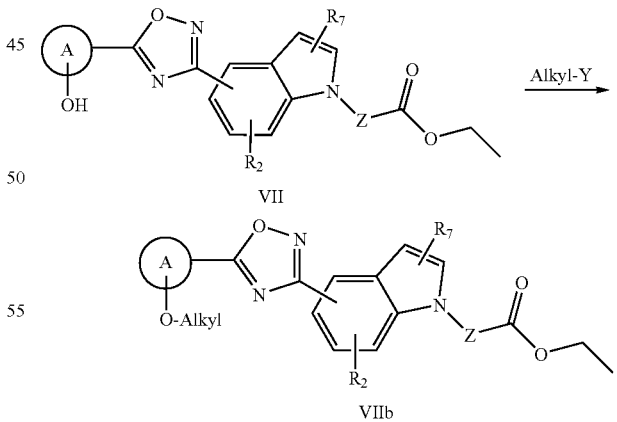

In certain cases it is possible to alkylate the intermediate indole (V) where $R_1$, $R_2$, $R_7$ and A are as defined in formula (I) directly with carboxylic acid-substituted alkyl bromide to generate the final compound (I) without the need for a hydrolysis step (Scheme VIII). A suitable base for this transformation is cesium carbonate.

Scheme VIII

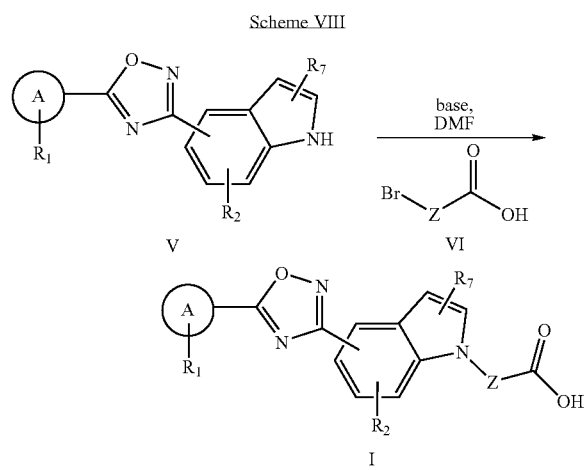

Pharmaceutically acceptable salts may be prepared conventionally by reaction with the appropriate acid or acid derivative.

The potencies and efficacies of the compounds of this invention for the S1P1 receptor can be determined by GTPγS assay performed on the human cloned receptor as described herein or by the yeast binding assay, also described herein Compounds of formula (I) have demonstrated agonist activity at the S1P1 receptor, using functional assays described herein.

Compounds of formula (I) and their pharmaceutically acceptable salts are therefore of use in the treatment of conditions or disorders which are mediated via the S1P1 receptor. In particular the compounds of formula (I) and their pharmaceutically acceptable salts are of use in the treatment of multiple sclerosis, autoimmune diseases, chronic inflammatory disorders, asthma, inflammatory neuropathies, arthritis, transplantation, Crohn's disease, ulcerative colitis, lupus erythematosis, psoriasis, ischemia-reperfusion injury, solid tumours, and tumour metastasis, diseases associated with angiogenesis, vascular diseases, pain conditions, acute viral diseases, inflammatory bowel conditions, insulin and non-insulin dependant diabetes (herein after referred to as the "Disorders of the Invention").

It is to be understood that "treatment" as used herein includes prophylaxis as well as alleviation of established symptoms.

Thus the invention also provides a compound of formula (I) or a pharmaceutically acceptable salt thereof, for use as a therapeutic substance, in particular in the treatment of the conditions or disorders mediated via the S1P1 receptor. In particular the invention provides a compound of formula (I) or a pharmaceutically acceptable salt thereof for use as a therapeutic substance in the treatment of multiple sclerosis, autoimmune diseases, chronic inflammatory disorders, asthma, inflammatory neuropathies, arthritis, transplantation, Crohn's disease, ulcerative colitis, lupus erythematosis, psoriasis, ischemia-reperfusion injury, solid tumours, and tumour metastasis, diseases associated with angiogenesis, vascular diseases, pain conditions, acute viral diseases, inflammatory bowel conditions, insulin and non-insulin dependant diabetes. The invention further provides a method of treatment of conditions or disorders in mammals including humans which can be mediated via the S1P1 receptor, which comprises administering to the sufferer a therapeutically safe and effective amount of a compound of formula (I) or a pharmaceutically acceptable salt thereof.

In another aspect, the invention provides for the use of a compound of formula (I) or a pharmaceutically acceptable salt thereof in the manufacture of a medicament for use in the treatment of the conditions or disorders mediated via the S1P1 receptor In order to use the compounds of formula (I) and pharmaceutically acceptable salts thereof in therapy, they will normally be formulated into a pharmaceutical composition in accordance with standard pharmaceutical practice. The present invention also provides a pharmaceutical composition, which comprises a compound of formula (I) or a pharmaceutically acceptable salt thereof, and a pharmaceutically acceptable carrier or excipient.

In a further aspect, the present invention provides a process for preparing a pharmaceutical composition, the process comprising mixing a compound of formula (I) or a pharmaceutically acceptable salt thereof and a pharmaceutically acceptable carrier or excipient.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents (e.g. pregelatinised maize starch, polyvinylpyrrolidone or hydroxypropyl methylcellulose); fillers (e.g. lactose, microcrystalline cellulose or calcium hydrogen phosphate); tabletting lubricants (e.g. magnesium stearate, talc or silica); disintegrants (e.g. potato starch or sodium starch glycollate); and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavourings or colorants, buffer salts and sweetening agents as appropriate. Preparations for oral administration may be suitably formulated to give controlled release of the active compound.

For parenteral administration, fluid unit dosage forms are prepared utilising a compound of the invention or pharmaceutically acceptable salts thereof and a sterile vehicle. Formulations for injection may be presented in unit dosage form e.g. in ampoules or in multi-dose, utilising a compound of the invention or pharmaceutically acceptable derivatives thereof and a sterile vehicle, optionally with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of formula (I) or pharmaceutically acceptable salts thereof may also be formulated in rectal compositions such as suppositories or retention enemas, e.g. containing conventional suppository bases such as cocoa butter or other glycerides.

The compounds of formula (I) or pharmaceutically acceptable salts thereof may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of formula (I) or pharmaceutically acceptable salts thereof, may be formulated as solutions for administration via a suitable metered or unitary dose device or alternatively as a powder mix with a suitable carrier for administration using a suitable delivery device. Thus compounds of formula (I) or pharmaceutically acceptable salts thereof may be formulated for oral, buccal, parenteral, topical (including ophthalmic and nasal), depot or rectal administration or in a form suitable for administration by inhalation or insufflation (either through the mouth or nose).

The compounds of formula (I) or pharmaceutically acceptable salts thereof may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

The composition may contain from 0.1% to 99% by weight, preferably from 10 to 60% by weight, of the active material, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, 1.0 to 500 mg or 1.0 to 200 mg and such unit doses may be administered more than once a day, for example two or three times a day.

Compounds of formula (I) or pharmaceutically acceptable salts thereof may be used in combination preparations. For example, the compounds of the invention may be used in combination with cyclosporin A, methotrexate, steriods, rapamycin, proinflammatory cytokine inhibitors, immunomodulators including biologicals or other therapeutically active compounds.

The subject invention also includes isotopically-labeled compounds, which are identical to those recited in formulas I and following, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3H$, $^{11}C$, $^{14}C$, $^{18}F$, $^{123}I$ and $^{125}I$.

Compounds of the present invention and pharmaceutically acceptable salts of said compounds that contain the aforementioned isotopes and/or other isotopes of other atoms are within the scope of the present invention. Isotopically-labeled compounds of the present invention, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^8F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of formula (I) and following of this invention can generally be prepared by carrying out the procedures disclosed in the Schemes and/or in the Examples below, by substituting a readily available isotopically labelled reagent for a non-isotopically labeled reagent.

All publications, including but not limited to patents and patent applications, cited in this specification are herein incorporated by reference as if each individual publication were specifically and individually indicated to be incorporated by reference herein as though fully set forth.

The following Descriptions and Examples illustrate the preparation of compounds of the invention.

Conditions, Hardware and Software for Analytical LCMS Systems

Hardware

Agilent 1100 Gradient Pump
Agilent 1100 Autosampler
Agilent 1100 DAD Dectector
Agilent 1100 Degasser
Agilent 1100 Oven
Agilent 1100 Controller
Waters Acquity Binary Solvent Manager
Waters Acquity Sample Manager
Waters Acquity PDA
Waters ZQ Mass Spectrometer
Sedere Sedex 55, Sedere Sedex 85, Sedere Sedex 75 or Polymer Labs PL-ELS-2100

Software

Waters MassLynx version 4.0 SP2 or version 4.1
For 5 Minute Method

Column

The column used is a Waters Atlantis, the dimensions of which are 4.6 mm×50 mm.

The stationary phase particle size is 3 μm.
Solvents
A: Aqueous solvent=Water+0.05% Formic Acid
B: Organic solvent=Acetonitrile+0.05% Formic Acid
Method
The generic method used has a 5 minute runtime.

| Time/min | % B |
|---|---|
| 0 | 3 |
| 0.1 | 3 |
| 4 | 97 |
| 4.8 | 97 |
| 4.9 | 3 |
| 5.0 | 3 |

Flow Rate
The above method has a flow rate of 3 ml/mins
For 2 Minute Method
Software
Waters MassLynx version 4.1
Column
The column used is a Waters Acquity BEH HPLC C18, the dimensions of which are 2.1 mm×50 mm. The stationary phase particle size is 1.7 μm.
Solvents
A: Aqueous solvent=Water+0.05% Formic Acid
B: Organic solvent=Acetonitrile+0.05% Formic Acid
Weak Wash=1:1 Methanol:Water
Strong Wash=Water
Method
The generic method used has a 2 minute runtime.

| Time/min | % B |
|---|---|
| 0 | 3 |
| 0.1 | 3 |
| 1.5 | 97 |
| 1.9 | 97 |
| 2.0 | 3 |

The above method has a flow rate of 1 ml/min.
The injection volume for the generic method is 0.5 ul
The column temperature is 40 deg
The UV detection range is from 220 to 330 nm
Open Access Mass Directed Auto Prep System (MDAP)
Hardware
Open Access Mass Directed Prep instruments consist of the following:
1 Waters 600 Gradient pump
1 Waters 2767 inject/collector
1 Waters Reagent manager
1 MicroMass ZQ Mass Spectrometer
1 Gilson Aspec—waste collector
1 Gilson 115 post-fraction UV detector
1 Computer System.
Software
MicroMass MassLynx v4.0
Column
The column used is typically a Supelco LCABZ++ column whose dimensions are 20 mm internal diameter by 100 mm in length. The stationary phase particle size is 5 μm.
Solvents
A: Aqueous solvent=Water+0.1% Formic Acid
B: Organic solvent=MeCN:Water 95:5+0.05% Formic Acid
Make up solvent=MeOH:Water 80:20+50 mMol Ammonium Acetate
Needle rinse solvent=MeOH:Water:DMSO 80:10:10
Methods
One of five methods may be used depending on the analytical retention time of the compound of interest.
All have a 15-minute runtime, which comprises of a 10-minute gradient followed by a 5-minute column flush and re-equilibration step.
MDP 1.5-2.2=0-30% B
MDP 2.0-2.8=5-30% B
MDP 2.5-3.0=15-55% B
MDP 2.8-4.0=30-80% B
MDP 3.8-5.5=50-90% B
Flow Rate
All of the above methods have a flow rate of 20 ml/min.
Alternative system:
Hardware
Waters 2525 Binary Gradient Module
Waters 515 Makeup Pump
Waters Pump Control Module
Waters 2767 Inject Collect
Waters Column Fluidics Manager
Waters 2996 Photodiode Array Detector
Waters ZQ Mass Spectrometer
Gilson 202 fraction collector
Gilson Aspec waste collector
Software
Waters MassLynx version 4 SP2
Column
The columns used are Waters Atlantis, the dimensions of which are 19 mm×100 mm (small scale) and 30 mm×100 mm (large scale). The stationary phase particle size is 5 mm.
Solvents
A: Aqueous solvent=Water+0.1% Formic Acid
B: Organic solvent=Acetonitrile+0.1% Formic Acid
Make up solvent=Methanol:Water 80:20
Needle rinse solvent=Methanol
Methods
There are five methods used depending on the analytical retention time of the compound of interest. They have a 13.5-minute runtime, which comprises of a 10-minute gradient followed by a 3.5 minute column flush and re-equilibration step.
Large/Small Scale 1.0-1.5=5-30% B
Large/Small Scale 1.5-2.2=15-55% B
Large/Small Scale 2.2-2.9=30-85% B
Large/Small Scale 2.9-3.6=50-99% B
Large/Small Scale 3.6-5.0=80-99% B (in 6 minutes followed by 7.5 minutes flush and re-equilibration)
Flow Rate
All of the above methods have a flow rate of either 20 mls/min (Small Scale) or 40 mls/min (Large Scale).
Shallow Gradients
Large 1.5 to 2.3 min=13-29% B
Large 1.9 to 2.3 min=25-41% B
Large 2.3 to 2.6 min=37-53% B
Large 2.6 to 3.1 min=49-65% B
Large 3.1 to 3.6 min=61-77% B
Conditions Used for NMR
Hardware
Bruker 400 MHz Ultrashield
Bruker B-ACS60 Autosampler
Bruker Advance 400 Console
Bruker DPX250
Bruker AVANCE 500
Bruker DRX600

Software

User interface—NMR Kiosk

Controlling software—XWin NMR version 3.0

Chromatography

Unless stated otherwise, all chromatography was carried out using silica columns Abbreviations:

g—grams mg—milligrams ml—milliliters ul—microliters

MeCN—acetonitrile

MeOH—methanol

EtOH—ethanol

Et$_2$O—diethyl ether

EtOAc—ethyl acetate

DCM—dichloromethane

DIAD—diisopropyl azodicarboxylate

DME—1,2-bis(methyloxy)ethane

DMF—N,N-dimethylformamide

DMSO—dimethylsulphoxide

EDAC—N-(3-Dimethylaminopropyl)-N'-ethylcarbodiimide hydrochloride

EDC—N-(3-Dimethylaminopropyl)-N'-ethylcarbodiimide hydrochloride

EDCI—N-(3-Dimethylaminopropyl)-N'-ethylcarbodiimide hydrochloride

HOBT/HOBt—Hydroxybenzotriazole

IPA—isopropylalcohol

NCS—N-chlorosuccinimide

PyBOP—Benzotriazol-1-yl-oxytripyrrolidinophosphonium hexafluorophosphate

THF—tetrahydrofuran dba—dibenzylidene acetone

RT—room temperature

° C.—degrees Celsius

M—Molar

H—proton s—singlet d—doublet t—triplet q—quartet

MHz—megahertz

MeOD—deuterated methanol

LCMS—Liquid Chromatography Mass Spectrometry

LC/MS—Liquid Chromatography Mass Spectrometry

MS—mass spectrometry

ES—Electrospray

MH$^+$—mass ion+H$^+$

MDAP—mass directed automated preparative liquid chromatography.

sat.—saturated

General Chemistry Section

The intermediates for the preparation of the examples may not necessarily have been prepared from the specific batch described.

Description for D1

N-Hydroxy-1H-indole-5-carboximidamide (D1)

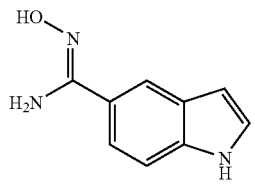

5-Cyanoindole (1.00 g), hydroxylamine.HCl (978 mg) and NaHCO$_3$ (2.95 g) were dissolved/suspended in MeOH (14 ml), heated to 50° C. and stirred overnight. LCMS analysis showed the reaction was incomplete after this time so a further portion of hydroxylamine.HCl (978 mg) was added and the reaction temperature raised to 80° C. The reaction was complete after 4 hours. The reaction mixture was cooled to RT and evaporated to dryness under reduced pressure. The residue was treated with 1M aqueous HCl (50 ml) and extracted with EtOAc (2×50 ml). This failed to extract the product from the aqueous solution so it was treated with 2M aqueous NaOH to adjust the pH to approximately 7 then re-extracted with EtOAc (3×50 ml). The combined organics were washed with brine (30 ml), dried over MgSO$_4$, filtered and evaporated to dryness to give the title compound (1.36 g) as a brown oil. δH (MeOD, 400 MHz) 6.50 (1H, s), 7.27 (1H, s), 7.36-7.45 (2H, m), 7.88 (1H, s). MS (ES): C$_9$H$_8$N$_3$O requires 175; found 176 (MH$^+$).

Description for D2

5-{5-[4-Phenyl-5-(trifluoromethyl)-2-thienyl]-1,2,4-oxadiazol-3-yl}-1H-indole (D2)

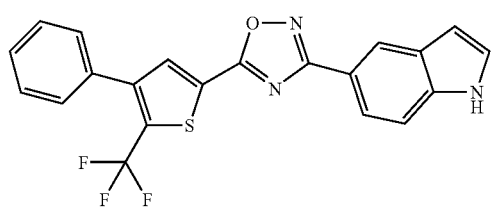

D1 (174 mg) and methyl 4-phenyl-5-(trifluoromethyl)-2-thiophenecarboxylate (286 mg) were combined, treated with sodium ethoxide (21% wt in EtOH, 411 ul) and heated to 120° C. in a microwave reactor for 30 minutes. LCMS analysis showed the reaction was incomplete so microwave heating was continued for a further two periods of 30 minutes. The reaction mixture was then cooled to RT, quenched with H$_2$O (2 ml) and evaporated to dryness under reduced pressure to give the crude product (411 mg) as a brown solid. The crude residue was purified on a 40+S Biotage cartridge, eluting with a 0 to 50% mixture of Et$_2$O in petroleum ether. This gave the title compound (122 mg) as an off-white solid. δH (CDCl$_3$, 400 MHz): 6.68 (1H, s), 7.30 (1H, t), 7.41-7.55 (6H, m), 7.92 (1H, s), 7.99 (1H, d), 8.36 (1H, br. s), 8.50 (1H, s). MS (ES): C$_{21}$H$_{12}$F$_3$N$_3$OS requires 411; found 410 (M−H$^+$).

Description for D3

Ethyl 3-(5-{5-[4-phenyl-5-(trifluoromethyl)-2-thienyl]-1,2,4-oxadiazol-3-yl}-1H-indol-1-yl)propanoate (D3)

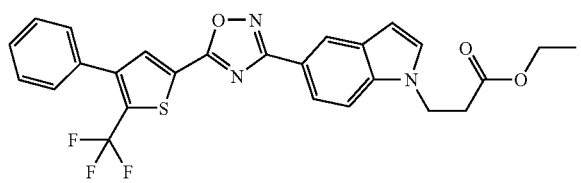

D2 (100 mg) was dissolved in DMF (1.2 ml), treated with $K_2CO_3$ (50 mg) then ethyl 3-bromopropionate (90 mg) and heated to 130° C. overnight. After this time LCMS showed the reaction to be incomplete so further ethyl 3-bromopropionate was added (45 mg) and stirring continued at 130° C. for 2 hours. LCMS showed no change so the reaction mixture was evaporated then partitioned between DCM and $H_2O$. The organic layer was removed and the aqueous solution extracted with DCM. The combined organics were dried over $MgSO_4$, filtered and evaporated to give the crude product (148 mg). This was purified on a silica cartridge (25+S), eluting with a 0 to 25% mixture of EtOAc in petroleum ether and then again on a 25+M cartridge with a 0 to 30% mixture of EtOAc in petroleum ether to give the title compound MF105672-144A3 (38 mg) as a white solid. δH (CDCl$_3$, 400 MHz): 1.21 (3H, t), 2.85 (2H, t), 4.12 (2H, q), 4.50 (2H, t), 6.60 (1H, d), 7.21 (1H, d), 7.42-7.52 (6H, m), 7.91 (1H, s), 8.00 (1H, d), 8.46 (1H, s). MS (ES$^+$): $C_{26}H_{20}F_3N_3O_3S$ requires 511; found 512 (MH$^+$).

Description for D3 Alternative Procedure

Ethyl 3-(5-{5-[4-phenyl-5-(trifluoromethyl)-2-thienyl]-1,2,4-oxadiazol-3-yl}-1H-indol-1-yl)propanoate (D3)

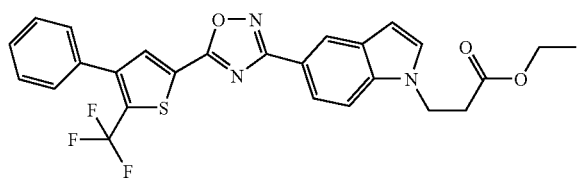

5-{5-[4-phenyl-5-(trifluoromethyl)-2-thienyl]-1,2,4-oxadiazol-3-yl}-1H-indole (D2) (600 mg), ethyl 3-bromopropanoate (374 µl), caesium carbonate (950 mg) and DMF were heated at 140° C. for 1 hour in a microwave reactor. A further 1 eq. of ethyl 3-bromopropanoate (187 µl) was added and the mixture heated for 30 minutes. The reaction mixture was then evaporated, dissolved in DCM and filtered to give the title compound (650 mg) as a brown solid. δH (CDCl$_3$, 400 MHz): 1.21 (3H, t), 2.85 (2H, t), 4.13 (2H, q), 4.50 (2H, t), 6.61 (1H, d), 7.22 (1H, d), 7.44-7.52 (6H, m), 7.89-7.92 (1H, m), 7.98-8.02 (1H, m), 8.45-8.46 (1H, m). MS (ES): $C_{26}H_{20}F_3N_3O_3S$ requires 511; found 512 (MH$^+$).

Description for D4 3-Chloro-4-[(1-methylethyl)oxy]benzoic acid (D4)

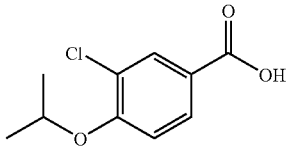

Propan-2-ol (2.45 ml) and PPh$_3$ (1.18 g) were dissolved in THF (30 ml), cooled to 0° C., treated with methyl 3-chloro-4-hydroxybenzoate (6.00 g) followed by the drop-wise addition of DIAD (9.44 ml) and stirred at RT overnight. The reaction mixture was then evaporated and purified on silica cartridges (4×100 g), eluting with a 0 to 40% mixture of EtOAc in pentane to give the crude product (7.00 g) as a colourless oil. This was dissolved in MeOH (30 ml) and 2 M aqueous NaOH (30 ml) and stirred at RT for a weekend. The reaction mixture was then evaporated and re-dissolved in $H_2O$. This solution was washed with $Et_2O$, acidified to pH=1 and extracted with $Et_2O$. These latter extracts were dried over $MgSO_4$, filtered and evaporated to give the title compound (4.16 g) as a white solid. δH (MeOD, 400 MHz): 1.37 (6H, d), 4.77 (1H, septet), 7.12 (1H, d), 7.90 (1H, d), 7.98 (1H, s). MS (ES): $C_{10}H_{11}ClO_3$ requires 214; found 215 (MH$^+$).

Alternative Synthesis

3-Chloro-4-[(1-methylethyl)oxy]benzoic acid (D4)

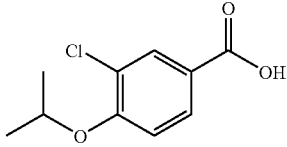

Methyl-4-hydroxy-3-chloro benzoate (13.4 g) was dissolved in DMF (150 ml), treated with $K_2CO_3$ (19.9 g) followed by isopropyl bromide (13.5 ml) and the resultant mixture heated to 70° C. and stirred overnight. The reaction mixture was then cooled to RT, evaporated to dryness, re-dissolved in EtOH, filtered and evaporated once more to give the intermediate ester (22.2 g) as a white solid. This compound was a mixture of ethyl and methyl esters and used crude in the next reaction.

The crude intermediate (22.2 g) was dissolved in MeOH (75 ml), treated with 2M aqueous NaOH (75 ml), heated to 60° C. and stirred for 2 hours. The reaction mixture was then cooled to RT, the MeOH evaporated and the remaining aqueous solution acidified with 5M aqueous HCl (30 ml). The precipitate was filtered off and dried to give the title compound (15.1 g) as a white solid. δH (CDCl$_3$, 400 MHz): 1.42 (6H, d), 4.70 (1H, septet), 6.97 (1H, d), 7.97 (1H, d), 8.12 (1H, s). MS (ES): $C_{10}H_{11}ClO_3$ requires 214; found 213 (MH$^+$).

Description for D5 MF105672-175A2

5-(5-{3-Chloro-4-[(1-methylethyl)oxy]phenyl}-1,2,4-oxadiazol-3-yl)-1H-indole (D5)

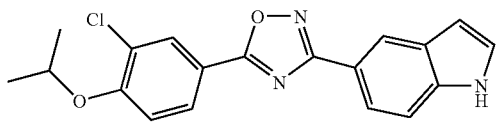

D1 (500 mg), D4 (611 mg) and PyBOP (1.66 g) were dissolved in DMF and stirred overnight. The reaction mixture was then evaporated and partitioned between EtOAc and H$_2$O. The organic layer was washed with H$_2$O (×2) then brine, dried over MgSO$_4$, filtered and evaporated to give the crude product. This was purified on a silica cartridge, eluting with a 0 to 50% mixture of Et$_2$O in hexane to give the title compound (120 mg) as a white solid. δH (CDCl$_3$, 400 MHz): 1.43 (6H, d), 4.69 (1H, septet), 6.92 (1H, s), 7.04 (1H, d), 7.25 (1H, s), 7.48 (1H, d), 8.00 (1H, d), 8.07 (1H, d), 8.25 (1H, s), 8.39 (1H, br. s), 8.50 (1H, s). MS (ES): C$_{19}$H$_{16}$ClN$_3$O$_2$ requires 353; found 354 (MH$^+$).

Description for D5 Alternative Procedure 5-(5-{3-Chloro-4-[(1-methylethyl)oxy]phenyl}-1,2,4-oxadiazol-3-yl)-1H-indole (D5)

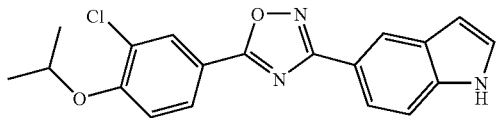

A mixture of 5-cyanoindole (5.00 g), NH$_2$OH.HCl (6.11 g) and NaHCO$_3$ (14.77 g) in EtOH (176 ml) was heated at 70° C. under an atmosphere of Ar overnight and then at 80° C. for 2.5 hours. The reaction mixture was then filtered and evaporated to give a yellow-orange solid (crude material D1).

D4 (7.55 g), HOBT (5.23 g) and EDCI (7.42 g) were dissolved in DMF (88 ml). This mixture was stirred for 10 minutes and then the yellow-orange solid from above (6.16 g) dissolved in DMF (88 ml) was added. The reaction mixture was heated to 80° C. overnight then evaporated and partitioned between EtOAc and H$_2$O. The phases were separated and the aqueous solution extracted with two further portions of EtOAc. The combined organic solutions were dried and evaporated. Part of the crude residue was purified on a 40+M Biotage cartridge, eluting with a 5-30% mixture of EtOAc in hexane. This gave the title compound (1.45 g) as an off-white solid. δH (CDCl$_3$, 400 MHz): 1.45 (6H, d), 4.72 (1H, septet), 6.66-6.69 (1H, m), 7.06 (1H, d), 7.29 (1H, apparent triplet or dd), 7.50 (1H, d), 8.01 (1H, dd), 8.08 (1H, dd), 8.27 (1H, d), 8.49-8.52 (1H, m). MS (ES): C$_{19}$H$_{16}$ClN$_3$O$_2$ requires 353; found 354 (MH$^+$). The remaining crude reside was triturated with cold MeOH to give the title compound (3.54 g) as an off white solid. MS data as above.

Description for D6

Ethyl 3-[5-(5-{3-chloro-4-[(1-methylethyl)oxy]phenyl}-1,2,4-oxadiazol-3-yl)-1H-indol-1-yl]propanoate (D6)

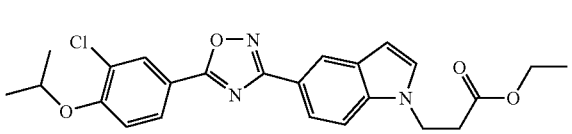

D5 (100 mg) was dissolved in DMF (1.5 ml). To this solution was added K$_2$CO$_3$ (58 mg) followed by ethyl 3-bromopropionate (72 ul) and the mixture stirred and heated to 100° C. After 1 hour only 5% conversion was observed by LCMS so further portions of K$_2$CO$_3$ (97 mg) and ethyl 3-bromopropionate (72 ul) were added. After 3 hours the reaction mixture was evaporated then partitioned between DCM and H$_2$O. The aqueous layer was extracted with DCM then the combined DCM solutions were washed with brine, dried over MgSO$_4$, filtered and evaporated to give the crude product. This was purified on a silica cartridge, eluting with a 0 to 50% mixture of Et$_2$O in petroleum ether. This gave the title compound (40 mg) as a white solid. δH (CDCl$_3$, 400 MHz): 1.21 (3H, t), 1.45 (6H, d), 2.85 (2H, t), 4.13 (2H, q), 4.51 (2H, t), 4.71 (1H, septet), 6.60 (1H, d), 7.07 (1H, d), 7.21 (1H, d), 7.45 (1H, d), 8.02 (1H, d), 8.08 (1H, d), 8.27 (1H, s), 8.47 (1H, s). MS (ES): C$_{24}$H$_{24}$ClN$_3$O$_4$ requires 453; found 454 (MH$^+$).

Description for D7

3-Chloro-5-(5-{3-chloro-4-[(1-methylethyl)oxy]phenyl}-1,2,4-oxadiazol-3-yl)-1H-indole (D7)

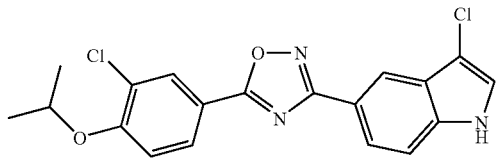

D5 (300 mg) and NCS (113 mg) were dissolved in DCM (4.2 ml) and stirred overnight at room temperature. The reaction mixture was then diluted with DCM and washed with H$_2$O. The aqueous solution was extracted with two further portions of DCM and the combined organic solutions were evaporated to dryness. The crude product was triturated with methanol to give the title compound (42 mg) as a brown solid. The methanol was then evaporated and the resultant brown solid triturated with DCM to give a second batch of the title compound (205 mg) as a brown solid. δH (d$_6$-DMSO, 400 MHz): 1.37 (6H, d), 4.89 (1H, septet), 7.45 (1H, d), 7.62 (1H, d), 7.70 (1H, s), 7.93 (1H, d), 8.15 (1H, d), 8.24 (1H, s), 8.25 (1H, s), 11.77 (1H, s). MS (ES): C$_{19}$H$_{15}$$^{35}$Cl$_2$N$_3$O$_2$ requires 387; found 388 (MH$^+$).

Description for D8

3-Chloro-5-{5-[4-phenyl-5-(trifluoromethyl)-2-thienyl]-1,2,4-oxadiazol-3-yl}-1H-indole (D8)

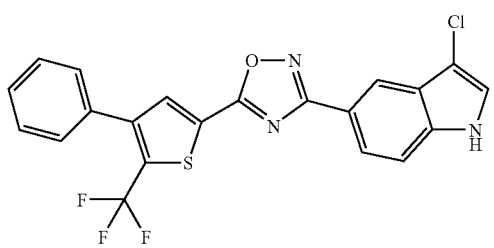

D2 (200 mg) and NCS (65 mg) were dissolved in DCM (5 ml) and stirred overnight at room temperature. The reaction mixture was then partitioned between DCM and H₂O. The DCM solution was evaporated to dryness and purified on a Biotage silica cartridge, eluting with a 25-75% mixture of diethyl ether in hexane. This gave the title compound (36 mg) as a brown solid. A second batch of the title compound was also obtained from this purification (86 mg) as a brown solid. δH (CDCl₃, 400 MHz): 7.28 (1H, m), 7.45-7.54 (6H, m), 7.93 (1H, s), 8.05 (1H, d), 8.28 (1H, br s), 8.49 (1H, s). MS (ES): $C_{21}H_{11}ClF_3N_3OS$ requires 445; found 444 (M–H⁺).

Description 9

N-Hydroxy-1H-indole-4-carboximidamide (D9)

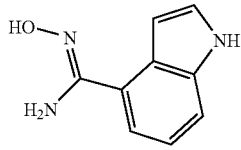

4-Cyanoindole (850 mg) was dissolved in EtOH (25 ml). To this solution was added NaHCO₃ (2.51 g) and NH₂OH.HCl (831 mg). The mixture was heated to 70° C. and stirred overnight. The reaction was incomplete so was heated at 80° C. for a further 4 hours. The reaction mixture was filtered and evaporated to give the title compound (980 mg) as a yellow semisolid. No purification attempted.

Description for D9 Alternative Procedure

N-Hydroxy-1H-indole-4-carboximidamide (D9)

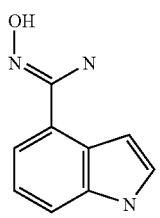

A mixture of 4-cyanoindole (5.0 g, 35.2 mmol), sodium hydrogen carbonate (8.9 g, 105.6 mmol) and hydroxylamine hydrochloride (4.9 g, 70.4 mmol) in ethanol (200 ml) was heated at 55° C. overnight. Sodium hydrogen carbonate (5.9 g, 70 mmol) and hydroxylamine hydrochloride (4.9 g, 70.4 mmol) was added. The mixture was heated for 4 days until only a small amount of starting material was present. The inorganics were filtered off, washing the solid well with ethanol and evaporated off the solvent. The residue was triturated with diethyl ether to give 5.8 g of off-white solid. δH (400 MHz, methanol-d₄) 6.76-6.78 (1H, m), 7.12 (1H, t), 7.24 (1H, dd), 7.29-7.33 (1H, m) 7.46 (1H, dd).

Description for D10

4-{5-[4-Phenyl-5-(trifluoromethyl)-2-thienyl]-1,2,4-oxadiazol-3-yl}-1H-indole (D10)

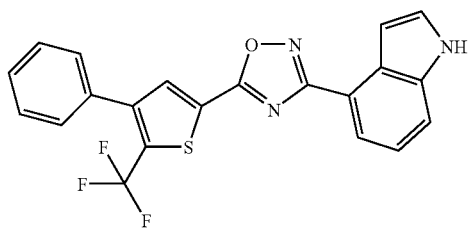

4-Phenyl-5-(trifluoromethyl)-2-thiophenecarboxylic acid (310 mg), HOBT (170 mg) and EDCI.HCl (242 mg) were dissolved in DMF (3 ml) and stirred at room temperature for 20 mins. D9 (200 mg) was dissolved in DMF (3 ml) and added to the above solution and stirring continued at room temperature for two hours. The reaction mixture was then heated to 90° C., cooled to RT, stood overnight, re-heated to 80° C. and stirred for 3 hours, cooled to room temperature and evaporated to dryness. The residue was re-dissolved in H₂O and extracted with EtOAc (×3) and the combined organic extracts evaporated to dryness. The residue was purified by flash silica chromatography, eluting with a 25-75% mixture of diethyl ether in hexane to give the title compound (265 mg) as a brown solid. A sample of this compound (100 mg) was purified by MDAP to give the title compound (62 mg) as an off white solid. δH (CDCl₃, 400 MHz): 7.33-7.36 (2H, m), 7.41-7.42 (1H, m), 7.46-7.52 (5H, m), 7.61 (1H, d), 7.94 (1H, s), 8.06 (1H, d), 8.46 (1H, br s). MS (ES): $C_{21}H_{12}F_3N_3OS$ requires 411; found 412 (MH⁺).

Description for D11

Ethyl 3-bromo-2,2-dimethylpropanoate (D11)

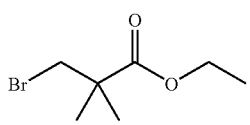

3-Bromo-2,2-dimethylpropanoic acid (200 mg) was dissolved in EtOH (5 ml) and treated with concentrated H₂SO₄ (0.4 ml). This mixture was heated at reflux overnight then evaporated. The residue was extracted from H₂O with EtOAc (×2) and the combined organic solutions dried and evaporated to give the title compound (316 mg) as a clear oil. δH (CDCl₃, 400 MHz) 1.20 (3H, t), 1.32 (6H, s), 3.51 (2H, s), 4.18 (2H, q).

Description for D12

3-Ethyl-4-(1-piperidinyl)benzonitrile (D12)

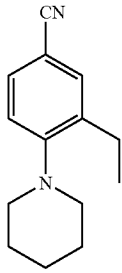

4-Amino-3-ethylbenzonitrile (3.0 g, 20.5 mmol), 1,5-dibromopentane (11.1 mL, 82.1 mmol), potassium carbonate (5.67 g, 41.0 mmol) and water (39.6 mL) were all split equally between ten microwave vials and each heated at 160° C. for 1 h. All reaction mixtures were combined and extracted twice with ethyl acetate (40 mL) and the combined organic fractions dried (phase separator) and concentrated in vacuo. Dichloromethane was added and then the mixture filtered before the filtrate was purified by silica chromatography, eluting 2-5% ethyl acetate in hexane to give the title compound as a colourless oil (823 mg, 3.85 mmol). Analysis indicated that the compound contained a small dibromopentane impurity. δH (methanol-$d_4$, 400 MHz) 7.52 (1H, dd), 7.47 (1H, dd), 7.13 (1H, d), 2.89 (4H, dd), 2.71 (2H, q), 1.76-1.71 (4H, m), 1.64-1.56 (2H, m), 1.25 (3H, t). MS (ES): $C_{14}H_{18}N_2$ requires 214; found 215 (MH$^+$).

Description for D13

3-Ethyl-4-(1-piperidinyl)benzoic acid (D13)

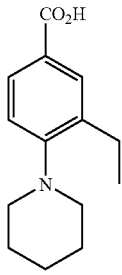

3-ethyl-4-(1-piperidinyl)benzonitrile (D12) (817 mg, 3.82 mmol) and potassium hydroxide (2.14 g, 38.2 mmol) in ethanol (35 mL) and water (8 mL) were heated to 90° C. (block temperature) for 9 h. Further potassium hydroxide (2.14 g, 38.2 mmol) and water (8 mL) were added and the reaction heated for a further 18 h. The reaction was allowed to cool and was neutralised with aqueous HCl. A white solid was collected by filtration and an attempt was made to purify the filtrate by SCX cartridge, but this failed. Both the solid and product of SCX were combined, methanol added and then the mixture acidified with acetic acid. The mixture was filtered to obtain the filtrate, which was then trapped on SCX cartridge, washed with methanol and eluted with 2M ammonia in methanol. On test scale this gave the title compound as a white solid (96 mg, 0.41 mmol) and on the remaining material gave a colourless oil (563 mg, 2.41 mmol). δH (methanol-$d_4$, 400 MHz): 7.85 (1H, d), 7.74 (1H, dd), 7.03 (1H, d), 2.85 (4H, dd), 2.73 (2H, q), 1.72 (4H, m), 1.61 (2H, m), 1.25 (3H, t) ppm. MS (ES): $C_{14}H_{19}NO_2$ requires 233; found 234 (MH$^+$).

Description for D14

Ethyl 5-chloro-6-(1-pyrrolidinyl)-3-pyridinecarboxylate (D14)

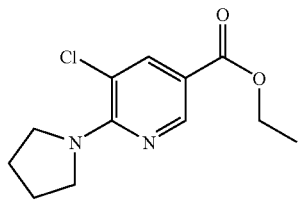

A mixture of 5,6-dichloronicotinic acid ethyl ester (1.00 g, 4.57 mmol), pyrrolidine (325 mg, 4.57 mmol), potassium carbonate (632 mg, 4.57 mmol) and copper powder (34 mg) in DMF (6.8 mL) was heated at 130° C. in the microwave for 20 min. Further pyrrolidine (163 mg, 2.29 mmol) was added and the reaction heated at 130° C. for 20 min. Water (7 mL) was added and the mixture extracted with ethyl acetate (2×14 mL). The combined organic extracts were washed with water (7 mL) and brine (7 mL) before being dried (phase separator) and concentrated in vacuo to give the title compound as an orange oil (1.06 g, 4.17 mmol). δH (methanol-$d_4$, 400 MHz): 8.45 (1H, d), 7.98 (1H, d), 4.31 (2H, q), 3.82-3.75 (4H, m), 2.0-1.93 (4H, m), 1.36 (3H, t) ppm. MS (ES): $C_{12}H_{15}ClN_2O_2$ requires 254, 256; found 255, 257 (MH$^+$).

Description for D15

5-Chloro-6-(1-pyrrolidinyl)-3-pyridinecarboxylic acid (D15)

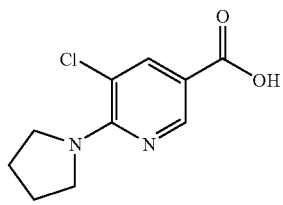

Ethyl 5-chloro-6-(1-pyrrolidinyl)-3-pyridinecarboxylate (D14) (1.06 g, 4.16 mmol) in ethanol (20 mL) and aqueous sodium hydroxide (2M, 2.08 mL, 4.16 mmol) was heated at 40° C. for 18 h. The reaction mixture was allowed to cool and was neutralised with 2M HCl (aq.). The title compound formed as a white solid and was filtered off and washed with methanol to give the title compound (243 mg, 1.08 mmol) SJ108923-113A3. The filtrate was trapped on an SCX column, eluting with 2M ammonia in methanol to give further title compound as an orange solid (467 mg, 2.07 mmol). δH (methanol-$d_4$, 400 MHz): 8.55 (1H, d), 8.03 (1H, d), 3.76-3.70 (4H, m), 1.96-1.90 (4H, m). MS (ES): $C_{10}H_{11}ClN_2O_2$ requires 226, 228; found 227, 229 (MH$^+$).

Description for D16

3-Ethyl-4-iodobenzonitrile (D16)

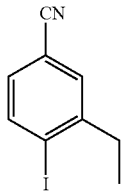

To 4-amino-3-ethylbenzonitrile (2.50 g, 17.1 mmol) stirred in water (14 mL) at 0° C. was added concentrated hydrochloric acid (7.80 mL, 257 mmol) dropwise followed by a solution of sodium nitrite (1.24 g, 18.0 mmol) in water (3.43 mL) dropwise. The resultant mixture was stirred for 15 minutes and then added over 15 minutes to a solution of potassium iodide (2.98 g, 18.0 mmol) in water (6.0 mL) at 0° C. The mixture was stirred at room temperature for 2 h. The mixture was extracted with ethyl acetate (3×100 mL) and the combined organic fractions washed with brine (100 mL), dried (phase separator) and concentrated in vacuo to give the title compound as a brown solid (4.21 g, 16.4 mmol). δH (methanol-$d_4$, 400 MHz): 8.02 (1H, d), 7.61 (1H, d), 7.24 (1H, dd), 2.80 (2H, q), 1.21 (3H, t). MS (ES): No mass ion observed.

Description for D17

4-(1-Cyclohexen-1-yl)-3-ethylbenzonitrile (D17)

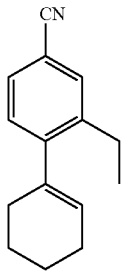

A mixture of 3-ethyl-4-iodobenzonitrile (D16) (1.23 g, 4.80 mmol), 1-cyclohexen-1-ylboronic acid (907 mg, 7.20 mmol), sodium methoxide (778 mg, 14.4 mmol) and bis(triphenylphosphine)palladium (II) chloride (337 mg, 0.48 mmol) in anhydrous methanol (12 mL) was heated at 80° C. for 10 minutes in the microwave. The reaction mixture was partitioned between ethyl acetate (40 mL) and water (40 mL) before the organic layer was further washed with water (40 mL), dried (phase separator) and concentrated in vacuo. The crude material was purified by silica chromatography, eluting 0-5% EtOAc in hexane over 30 minutes to give the title compound as a yellow oil (824 mg, 3.91 mmol). δH (methanol-$d_4$, 400 MHz) 7.56 (1H, d), 7.46 (1H, dd), 7.19 (1H, d), 5.61-5.56 (1H, m), 2.68 (2H, quart), 2.23-2.16 (4H, m), 1.85-1.68 (4H, m), 1.20 (3H, t). MS (ES): No mass ion observed.

Description for D18

4-(1-Cyclohexen-1-yl)-3-ethylbenzoic acid (D18)

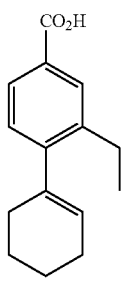

4-(1-cyclohexen-1-yl)-3-ethylbenzonitrile (D17) (824 mg, 3.91 mmol) and potassium hydroxide (2.19 g, 39.1 mmol) in ethanol (36 mL) and water (8 mL) were heated at 90° C. (block temperature) for 20 h. The reaction mixture was concentrated in vacuo and the residue partitioned between ethyl acetate (120 mL) and aqueous hydrochloric acid (2M, 50 mL) before the organic phase was washed with further hydrochloric acid (2M, 50 mL), dried (phase separator) and concentrated in vacuo to give the title compound as a yellow oil (808 mg, 3.51 mmol). δH (methanol-$d_4$, 400 MHz) 7.87 (1H d), 7.76 (1H dd), 7.11 (1H, d) 5.59-5.54 (1H, m), 2.68 (2H, q), 2.25-2.15 (4H, m), 1.84-1.67 (4H, m), 1.20 (3H, t). LCMS (ES): $C_{15}H_{18}O_2$ requires 230; found 229 (M–H$^+$).

Description for D19

4-Cyclohexyl-3-ethylbenzoic acid (D19)

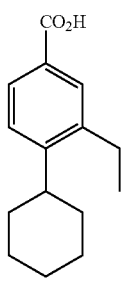

4-(1-cyclohexen-1-yl)-3-ethylbenzoic acid (D18) (803 mg, 3.49 mmol) was dissolved in methanol (70 mL) and hydrogenated on an H-Cube using a palladium on carbon cartridge. The product solution was concentrated in vacuo to give the title compound as a white solid (792 mg, 3.41 mmol). δH (methanol-$d_4$, 400 MHz): 7.82-7.68 (2H, m), 7.33 (1H, d), 2.83 (1H, m), 2.73 (2H, q), 1.87 (2H, m), 1.85-1.70 (3H, m), 1.58-1.30 (5H, m), 1.22 (3H, t). LCMS (ES): no mass ion observed.

Description for D20

1-Methylethyl 3-bromo-4-[(1-methylethyl)oxy]benzoate (D20)

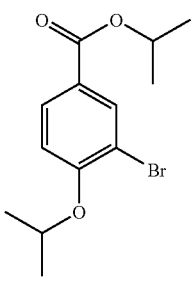

A mixture of 3-bromo-4-hydroxybenzoic acid (2.00 g, 9.22 mmol), 2-iodopropane (1.85 mL, 18.4 mmol) and potassium carbonate (2.55 g, 18.4 mmol) in DMF (175 mL) was heated to reflux for 5 h. The reaction was allowed to cool and was filtered. The filtrate was concentrated in vacuo and the residue partitioned between ethyl acetate (150 mL) and water (150 mL), which was basified with 2M NaOH. The organic phase was dried (phase separator) and concentrated in vacuo to give the title compound as a yellow oil (2.36 g, 7.84 mmol). $\delta$H (methanol-$d_4$, 400 MHz): 8.05 (1H, d), 7.90 (1H, dd), 7.25 (1H, d), 5.10 (1H, septet), 4.81 (1H, septet), 1.32 (6H, d), 1.31 (6H, d) ppm. MS (ES): no mass ion observed.

Description for D21

3-Bromo-4-[(1-methylethyl)oxy]benzoic acid (D21)

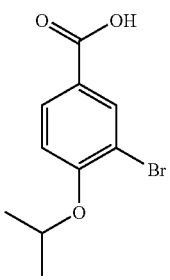

A solution of 1-methylethyl 3-bromo-4-[(1-methylethyl)oxy]benzoate (D20) (2.36 g, 7.84 mmol) in ethanol (100 mL) and aqueous sodium hydroxide (2M, 39 mL) was heated to reflux for 5 h. The reaction mixture was concentrated in vacuo and partitioned between ethyl acetate (125 mL) and water (125 mL), the latter acidified with 2M HCl (40 mL). The aqueous layer was extracted with further ethyl acetate (70 mL) and the combined organic extracts dried (phase separator) and concentrated in vacuo to give the title compound as an off-white solid (1.83 g, 7.06 mmol). $\delta$H (methanol-$d_4$, 400 MHz): 8.05 (1H, d), 7.89 (1H, dd), 7.23 (1H, d), 4.79 (1H, septet), 1.32 (6H, d). MS (ES): $C_{10}H_{11}BrO_3$ requires 258, 260; found 257, 259 (M−H$^+$).

Description for D22

Ethyl 4-bromo-3-chlorobenzoate (D22)

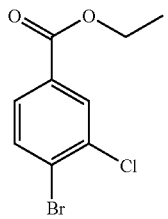

To a suspension of 4-bromo-3-chlorobenzoic acid (5.00 g, 21.2 mmol) in ethanol (50 mL) was added sulphuric acid (5 mL) and the resultant mixture heated to reflux for 60 h. The reaction was partitioned between ethyl acetate (50 mL) and water (50 mL). The aqueous layer was extracted with further ethyl acetate and the combined organic fractions dried (phase separator) and concentrated in vacuo to give the title compound as a brown oil/solid (5.09 g, 19.3 mmol). $\delta$H ($d_6$-DMSO, 400 MHz): 8.06 (1H, d), 7.96 (1H, d), 7.80 (1H, dd), 4.33 (2H, q), 1.33 (3H, t). MS (ES): no mass ion observed.

Description for D23

Ethyl 3-chloro-4-(2-methylpropyl)benzoate (D23)

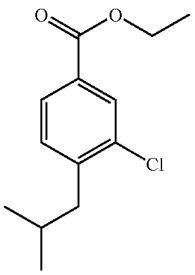

A solution of isobutylzinc bromide in THF (0.5 M, 30 mL, 15.0 mmol) was added under argon to ethyl 4-bromo-3-chlorobenzoate (D22) (2.00 g, 7.60 mmol) and then 1,1'-bis(diphenylphosphino)ferrocene-palladium(II) dichloride dichloromethane complex (930 mg, 1.14 mmol) was added. The reaction was heated to reflux for 4.5 h. The mixture concentrated in vacuo and the residue partitioned between ethyl acetate (125 mL) and water (125 mL). A solid formed, which was filtered off and discarded. The organic layer was washed with water (100 mL), dried (phase separator) and concentrated in vacuo. The crude product was purified by silica chromatography, eluting with 0-5% EtOAc in hexane over 30 minutes to give the title compound as a colourless oil (1.76 g, 7.33 mmol). $\delta$H ($d_6$-DMSO, 400 MHz): 7.91 (1H, d), 7.80 (1H, dd), 7.46 (1H, d), 4.30 (2H, q), 2.66 (2H, d), 1.88-2.01 (1H, m), 1.32 (3H, t), 0.89 (6H, d). MS (ES): no mass ion observed.

Description for D24

3-Chloro-4-(2-methylpropyl)benzoic acid (D24)

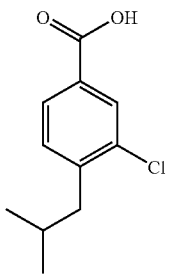

A solution of ethyl 3-chloro-4-(2-methylpropyl)benzoate (D23) (1.76 g, 7.33 mmol), and aqueous sodium hydroxide (2M, 3.70 mL, 7.4 mmol) in ethanol (30 mL) was heated at 40° C. for 3 h. The reaction mixture was concentrated in vacuo and the residue partitioned between ethyl acetate (100 mL) and water (100 mL), the latter acidified with 2M HCl (4 mL). The aqueous layer was extracted with ethyl acetate (100 mL) and the combined organic extracts dried (phase separator) and concentrated in vacuo to give the title compound as a white solid (1.35 g, 6.36 mmol). δH (d$_6$-DMSO, 400 MHz): 13.20 (1H, br. s), 7.89 (1H, d), 7.82 (1H, dd), 7.44 (1H, d), 2.64 (2H, d), 1.94 (1H, m), 0.89 (6H, d). MS (ES): $C_{11}H_{13}{}^{35}ClO_2$ requires 212; found 211 (M−H$^+$).

Description for D25

Methyl 3-cyano-4-{[(trifluoromethyl)sulfonyl]oxy}benzoate (D25)

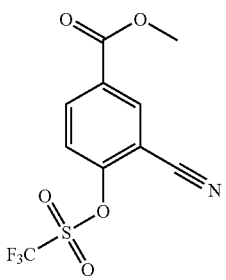

To a solution of methyl 3-cyano-4-hydroxybenzoate (3 g, 16.93 mmol) and triethylamine (3.54 ml, 25.4 mmol) in dry dichloromethane (60 ml) at 0° C. under a flush of argon was added trifluoromethanesulfonic anhydride (3.15 ml, 18.63 mmol) slowly dropwise. The reaction was allowed to warm to room temperature and stirred for 1 h. The reaction mixture was washed with 10% aqueous potassium carbonate (2×50 mL) and then aqueous HCl (2M, 2×50 mL) before the organic phase was dried (phase separator) and the solvent removed in vacuo to give the title compound as a dark brown oil, (5.165 g, 16.70 mmol). δH (CDCl$_3$, 400 MHz): 8.44 (1H, d), 8.38 (1H, dd), 7.60 (1H, d), 3.99 (3H, s). MS (ES): no mass ion observed.

Description for D26

Methyl 2-cyano-4-biphenylcarboxylate (D26)

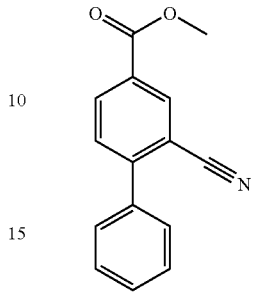

The following reaction was split into two batches with half the amounts: methyl 3-cyano-4-{[(trifluoromethyl)sulfonyl]oxy}benzoate (D25) (1.5 g, 4.85 mmol), phenylboronic acid (1.183 g, 9.70 mmol), potassium carbonate (2.011 g, 14.55 mmol) and palladium tetrakistriphenylphosphine(0) (0.561 g, 0.485 mmol) were taken up in DMF (24 ml) and the mixture heated in the microwave for 30 min at 150° C. The two reactions were combined and diluted with ethyl acetate (50 mL) and the mixture filtered through kieselguhr to remove palladium residues. The filtrate was concentrated in vacuo to reduce the amount of DMF and then the residue partitioned between saturated aqueous sodium bicarbonate (50 mL) and ethyl acetate (50 mL). The organic phase was washed with further sodium bicarbonate (50 mL) and then water (50 mL) before it was dried (MgSO$_4$), filtered and the solvent removed in vacuo. The brown solid was purified by silica chromatography, eluting 0-25% EtOAc in iso-hexane over 35 minutes to give the title compound as a white solid (935 mg, 3.94 mmol). δH (d$_6$-DMSO, 400 MHz): 8.42 (1H, d), 8.29 (1H, dd), 7.81 (1H, d), 7.65 (2H, m), 7.60-7.50 (3H, m), 3.92 (3H, s). MS (ES): no mass ion observed.

Description for D27

2-Cyano-4-biphenylcarboxylic acid (D27)

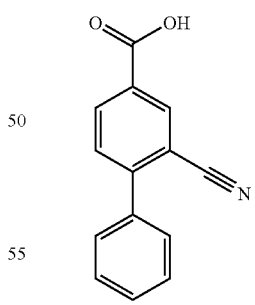

To methyl 2-cyano-4-biphenylcarboxylate (D26) (935 mg, 3.94 mmol) was added ethanol (18 ml) but dissolution did not occur so dichloromethane (10 ml) was added. Sodium hydroxide (2 ml, 4.00 mmol) was then added and the reaction stirred for 2 h. To the mixture was added dichloromethane (20 mL) and 2M aqueous HCl (10 mL). The layers were separated and the aqueous extracted with further dichloromethane (20 mL). The combined organic phase was dried (phase separator) and the solvent removed in vacuo to give a white solid, which was dissolved in methanol (30 mL) and aqueous sodium hydroxide was added (2M, 3 mL). The reaction was stirred at room temperature for 1 h before addition of water (20 mL). The reaction was stirred for a further 1 h. Dichloromethane (60 mL) was added and the mixture shaken and the layers separated. The aqueous phase was extracted with further dichloromethane (50 mL) before the combined organic phase was dried (phase separator) and the solvent removed in vacuo to give the title compound as a white solid, (849 mg, 3.80 mmol). δH (d$_6$-DMSO, 400 MHz): 13.60 (1H, br s), 8.38 (1H, d), 8.28 (1H, dd), 7.78 (1H, d), 7.63 (2H, m), 7.60-7.50 (3H, m). MS (ES): $C_{14}H_9NO_2$ requires 223; found 222 (M−H$^+$).

Description for D28

Ethyl 4-chloro-3-(trifluoromethyl)benzoate (D28)

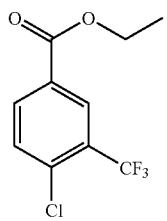

4-Chloro-3-(trifluoromethyl)benzoic acid (1 g, 4.45 mmol) was dissolved in ethanol (3 ml) and concentrated sulfuric acid (0.15 ml) was added. The mixture was heated in the microwave at 100° C. for 5 minutes and then 120° C. for 15 minutes. The solvent was removed in vacuo and the residue partitioned between saturated aq. sodium bicarbonate (50 ml) and ethyl acetate (50 ml). The aqueous layer was extracted with further EtOAc (50 ml) and the organic phases were combined, dried with a phase separator and concentrated in vacuo to give the title compound (1.026 g) (DN108121-148A3) as a colourless oil. δH (methanol-d$_4$, 400 MHz) 1.40 (3H, t), 4.41 (2H, q), 7.76 (1H, d), 8.21 (1H, dd), 8.33 (1H, d). MS (ES) no mass ion observed.

Description for D29

2-(Trifluoromethyl)-4-biphenylcarboxylic acid (D29)

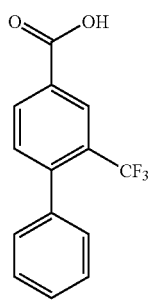

The reaction was split into 4, using a quarter of the reagents in each: to a mixture of 4-bromo-3-(trifluoromethyl)benzonitrile (4 g, 16.00 mmol), phenylboronic acid (3.90 g, 32.0 mmol) and potassium carbonate (6.63 g, 48.0 mmol) in N,N-dimethylformamide (DMF) (64 ml) was added palladium tetrakistriphenylphosphine(0) (1.849 g, 1.600 mmol). Each reaction was heated in the microwave at 150° C. for 30 min.

The combined reaction mixtures were filtered through celite, washed with ethyl acetate and the solvent removed in vacuo. The residue was partitioned between ethyl acetate (100 mL) and water (100 mL) and the organic phase washed with sodium bicarbonate solution (100 mL). The organic phase was dried (MgSO$_4$), filtered and the solvent removed in vacuo. The brown oil was triturated with dichloromethane and filtered to give a pale yellow solid, 2-(trifluoromethyl)-4-biphenylcarboxamide (2.47 g) which was used without further purification. To 2-(trifluoromethyl)-4-biphenylcarboxamide (2 g, 7.54 mmol) in ethanol (80 ml) was added potassium hydroxide (4.23 g, 75 mmol) and water and the mixture heated to 90° C. for 18 h. The reaction mixture was concentrated in vacuo and the residue partitioned between dichloromethane (100 mL) and 2M HCl (100 mL). The organic phase was isolated and dried (phase separator) and the solvent removed in vacuo to give the crude product. Purification using the Biotage Horizon, reverse phase cartridge, eluting 5-100% MeCN in water to give an off-white solid the title compound (960 mg) (N2123-46-A5). MS (ES): $C_{14}H_6F_3O_2$ requires 266; found 265 (M−H$^+$).

Description for D29 Alternative Procedure 2-(Trifluoromethyl)-4-biphenylcarboxylic acid (D29)

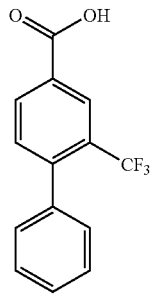

Batch A: A mixture of D98 (1.0 g, 3.96 mmol), phenyl boronic acid (724 mg, 5.94 mmol), palladium acetate (44 mg), (dicyclohexylphosphino)biphenyl (140.2 mg) and potassium fluoride (689 mg, 11.9 mmol) in THF (8 ml) was heated in the microwave at 120° C. for a total of 40 minutes.

Batch B: A mixture of D28 (500 mg, 1.98 mmol), phenyl boronic acid (290 mg, 2.38 mmol), palladium acetate (2.2 mg), (dicyclohexylphosphino)biphenyl (7 mg) and potassium fluoride (344 mg, 5.8 mmol) in THF (4 ml) was heated in the microwave at 120° C. for 20 minutes.

The reaction mixtures from batches A & B were combined, filtered and the filtrate concentrated in vacuo. The residue was purified by flash chromatography (0 to 5% EtOAc in hexane to give a mixture of starting material and coupled product. This material was dissolved in ethanol (10 ml) and 2M NaOH (aq) (5 ml) and then heated to reflux for 3 h. The solvent was removed in vacuo and the residue partitioned between DCM and 2M aq. HCl. The aq. was extracted with further DCM. The organic phases were combined and concentrated in vacuo. The crude material was purified by reversed phase chromatography on the Horizon eluting with 5 to 100% MeCN in water to afford the title compound as a white solid (367 mg). δH (d$_6$-DMSO, 400 MHz) 7.31-7.40 (2H, m), 7.44-7.52 (3H, m), 7.57 (1H, d), 8.24 (1H, dd), 8.29 (1H, d), 13.57 (1H, br. s). MS (ES): $C_{14}H_6F_3O_2$ requires 266; found 265 (M−H$^+$).

Description for D30

2'-Fluoro-2-(trifluoromethyl)-4-biphenylcarboxylic acid (D30)

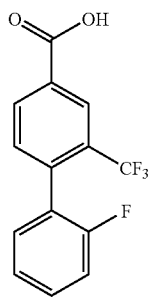

This material was prepared using a similar method to that described for D29 using (2-fluorophenyl)boronic acid and D98 except that only a single coupling reaction was performed, similar to batch A and the coupling reaction was heated for 20 minutes. MS (ES): $C_{14}H_8F_4O_2$ requires 284; found 283 (M–H$^+$).

Description for D31

Methyl 3-cyano-4-(2-methylpropyl)benzoate (D31)

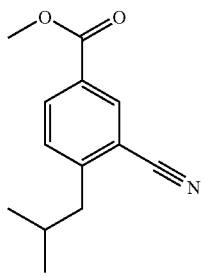

To methyl 3-cyano-4-{[(trifluoromethyl)sulfonyl]oxy}benzoate (D25) (1.5 g, 4.85 mmol) was added bromo(2-methylpropyl)zinc (48.5 ml, 24.25 mmol) in tetrahydrofuran (50 ml) under argon. To the solution was then added 1,1'-bis(diphenylphosphino)ferrocenedichloro palladium(II) dichloromethane complex (0.355 g, 0.485 mmol) and the reaction heated to reflux for 6 h. The mixture was quenched with water (2 mL) and then filtered through celite, washing with ethyl acetate. The solvent was removed in vacuo. The residue was partitioned between ethyl acetate (50 mL) and water (50 mL) and the organic phase dried (phase separator) and the solvent removed in vacuo. The residue was purified by silica chromatography, eluting 0-15% EtOAc in iso-hexane over 40 min. Two batches were collected, one of which was the title compound as a colourless oil (233 mg, 1.072 mmol). δH (CDCl$_3$, 400 MHz): 8.28 (1H, d), 8.15 (1H, dd), 7.38 (1H, d), 3.94, 3H, s), 2.78 (2H, d), 2.02 (1H, m), 0.96 (6H, d).

Description for D32

3-Cyano-4-(2-methylpropyl)benzoic acid (D32)

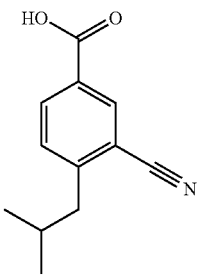

Methyl 3-cyano-4-(2-methylpropyl)benzoate (D31) (233 mg, 1.072 mmol) was dissolved in ethanol (4 ml) and 2M aqueous sodium hydroxide (1 ml, 2 mmol) was added. The reaction was stirred for 1 h. 2M aqueous HCl (10 mL) was added and the mixture extracted with dichloromethane (20 mL+10 mL). The organic phases were isolated and dried by phase separator and combined before the solvent was removed in vacuo to give the title compound as a white solid (203 mg, 0.999 mmol). δH (d$_6$-DMSO, 400 MHz) 13.43 (1H, br. s), 8.29 (1H, d), 8.14 (1H, dd), 7.59 (1H, d), 2.74 (2H, d), 1.96 (1H, m), 0.91 (6H, d). MS (ES): $C_{12}H_{13}NO_2$ requires 203; found 202 (M–H$^+$).

Description for D33

4-(2-Methylpropyl)-3-(trifluoromethyl)benzamide (D33)

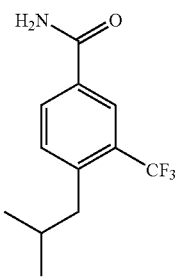

To a solution of 4-bromo-3-trifluoromethylbenzonitrile (1.25 g, 5.0 mmol) and isobutylzinc bromide (25 mmol) in THF (50 mL, 25 mmol) under argon was added 1,1'-bis(diphenylphosphino)ferrocenedichloro palladium(II) dichloromethane complex (612 mg, 0.75 mmol) and the reaction heated at reflux for 5 h. The mixture was concentrated in vacuo and the residue partitioned between ethyl acetate (80 mL) and water (80 mL). A solid formed and was filtered off and discarded. The organic layer was washed with water (80 mL) before it was dried (phase separator) and concentrated in vacuo to give the crude title compound as a black oil. This was used directly in the next step (1.35 g).

Description for D34

4-(2-Methylpropyl)-3-(trifluoromethyl)benzoic acid (D34)

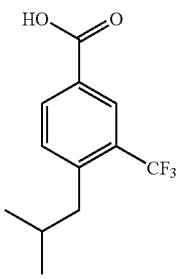

4-(2-methylpropyl)-3-(trifluoromethyl)benzamide (D33) (1.35 g, 5.50 mmol) was dissolved along with potassium hydroxide (3.09 g, 55.0 mmol) in ethanol (40 ml) and water (10.0 ml) and the solution heated to reflux for 18 h. The reaction mixture was concentrated in vacuo and the mixture separated between EtOAc (150 mL) and aqueous sodium hydroxide (2M, 150 mL). The layers were separated and the organic phase extracted with further sodium hydroxide solution (200 mL). LCMS of both phases showed product in both. Therefore the aqueous phase was acidified to pH1 with HCl (5M) and extracted back into EtOAc (2×150 mL) and these organic phases combined with the original organic phase. The solvent was removed in vacuo and the residue purified by reverse phase chromatography, eluting 5-100% MeCN in $H_2O$ over 2000 mL and the solvent removed in vacuo to give a brown solid (690 mg, 2.410 mmol). This solid was triturated with hexane to give the title compound as a buff solid (135 mg, 0.548 mmol) and the filtrate purified by MDAP to give further title compound as a white solid (102 mg, 0.414 mmol). δH ($d_6$-DMSO, 400 MHz): 13.39 (1H, br. s), 8.16 (1H, s), 8.13 (1H, d), 7.62 (1H, d), 2.69 (2H, d), 1.97 (1H, m), 0.90 (6H, d). MS (ES): $C_{12}H_{13}F_3O_2$ requires 246; found 245 ($M-H^+$).

Description for D35

5-Formyl-2-{[(1S)-1-methylpropyl]oxy}benzonitrile (D35)

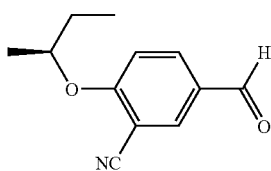

(2S)-2-Butanol (0.99 g, 0.013 mol) was dissolved in DMF (50 ml) and the solution cooled to 0° C. To this was added sodium hydride, (60% dispersion in mineral oil, 1.54 g, 0.036 mol) in a portion-wise manner, the mixture was stirred at 0° C. for 10 minutes after complete addition. 2-Fluoro-5-formyl-benzonitrile (2.0 g, 0.013 mol) was then added and the reaction mixture allowed to warm to room temperature (slowly within the ice bath) and the reaction mixture was stirred overnight at room temperature. The reaction mixture was then cooled to 0° C., quenched with brine and diluted with EtOAc (~25 ml). The mixture was partitioned and the organic fraction extracted with water (~30 ml), the combined organics were dried by passing through a phase separating cartridge and then evaporated to dryness under reduced pressure to give the crude product. The crude residue was purified on a 40+M Biotage cartridge, eluting with a 20 to 50% mixture of EtOAc in hexane. This gave the title compound (220 mg) as a white solid. δH ($d_6$-DMSO, 400 MHz): 9.88 (1H, s), 8.30 (1H, s), 8.15 (1H, d), 7.49 (1H, d), 4.73-4.81 (1H, m), 1.63-1.79 (2H, m), 1.33 (3H, d), 0.95 (3H, t). MS (ES): $C_{12}H_{13}NO_2$ requires 203; found 204 ($MH^+$).

Description for D36

3-Cyano-4-{[(1S)-1-methylpropyl]oxy}benzoic acid (D36)

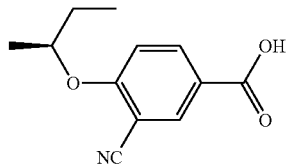

To a solution of 5-formyl-2-{[(1S)-1-methylpropyl]oxy}benzonitrile (D35) (220 mg, 1.08 mmol) in acetic acid (20 ml) was added sodium perborate tetrahydrate (334 mg, 2.17 mmol), the reaction mixture was heated at 50° C. over the weekend. The reaction mixture was concentrated in-vacuo. Water (~50 ml) was added, EtOAc (~30 ml) was added and the layers partitioned, the aq layer was extracted twice more with EtOAc (~30 ml) and the combined organics were evaporated to dryness under reduced pressure to give the title compound (245 mg) as an off white solid. δH ($d_6$-DMSO, 400 MHz): 8.17 (2H, apparent d), 7.39 (1H, s), 4.68-4.74 (1H, m), 1.55-1.76 (2H, m), 1.31 (3H, d), 0.95 (3H, t). MS (ES): $C_{12}H_{13}NO_2$ requires 219; found 220 ($MH^+$).

Description for D37

5-Formyl-2-{[(1R)-1-methylpropyl]oxy}benzonitrile (D37)

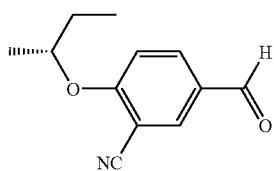

(2R)-2-Butanol (0.99 g, 0.013 mol) was dissolved in DMF (50 ml) and the solution cooled to 0° C. To this was added sodium hydride, 60% dispersion in mineral oil (1.54 g, 0.036 mol) in a portion-wise manner, the mixture was stirred at 0° C. for 10 minutes after complete addition. 2-Fluoro-5-formyl-benzonitrile (2.0 g, 0.013 mol) was then added and the reaction mixture allowed to warm to room temperature (slowly within the ice bath) and the reaction mixture was stirred overnight at room temperature. The reaction mixture was then cooled to 0° C., quenched with brine and diluted with EtOAc (~25 ml). The mixture was partitioned and the organic fraction extracted with water (~30 ml), the combined organics were dried by passing through a phase separating cartridge and evaporated to dryness under reduced pressure to give the crude product. The crude residue was purified on a 40+M Biotage cartridge, eluting with a 20 to 50% mixture of EtOAc in hexane. This gave the title compound (310 mg) as a yellow oil. δH (d$_6$-DMSO, 400 MHz): 9.88 (1H, s), 8.30 (1H, s), 8.15 (1H, d), 7.49 (1H, d), 4.73-4.81 (1H, m), 1.63-1.79 (2H, m), 1.33 (3H, d), 0.95 (3H, t) ppm.

Description for D38

3-Cyano-4-{[(1R)-1-methylpropyl]oxy}benzoic acid (D38)

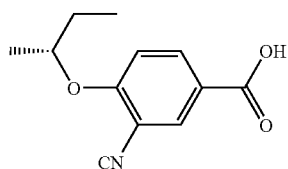

To a solution of 5-formyl-2-{[(1R)-1-methylpropyl]oxy}benzonitrile (D37) (310 mg, 1.53 mmol) in acetic acid (30 ml) was added sodium perborate tetrahydrate (471 mg, 3.05 mmol), the reaction mixture was heated at 50° C. over the weekend. The reaction mixture was concentrated in vacuo and water (~50 ml) added, EtOAc (~30 ml) was added and the layers partitioned, the aq layer was extracted twice more with EtOAc (~30 ml) and the combined organics evaporated to dryness under reduced pressure to give the title compound (315 mg) as an off-white solid. δH (d$_6$-DMSO, 400 MHz): 8.07-8.24 (2H, m), 7.38 (1H, d), 4.63-4.77 (1H, m), 1.55-1.83 (2H, m), 1.31 (3H, d), 0.95 (3H, t). MS (ES$^+$): C$_{12}$H$_{13}$NO$_2$ requires 219; found 220 (MH$^+$).

Description for D39

Methyl 6-(methyloxy)-3-biphenylcarboxylate (D39)

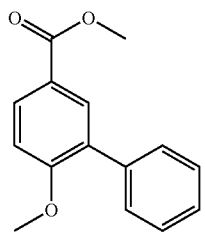

Methyl 3-bromo-4-(methyloxy)benzoate (245 mg, 1 mmol, commercially available) was dissolved in DME: 2N Na$_2$CO$_3$ (2:1, 18 ml) and then phenyl boronic acid (244 mg) and tetrakistriphenylphosphine palladium(0) (58 mg) were added. The reaction was heated to 80° C. and then left to cool over the weekend. Added EtOAc and water, the organics were separated, dried and evaporated to give a black gum. Purification by flash chromatography afforded the title compound (194 mg) as a gum. δH (d$_6$-DMSO, 400 MHz) 3.83 (3H, s), 3.85 (3H, s), 7.24 (1H, d), 7.33-7.50 (5H, m), 7.83 (1H, d), 7.97 (1H, dd). MS (ES): C$_{15}$H$_{14}$O$_3$ requires 242; found 243 (MH$^+$).

Description for D40

6-(Methyloxy)-3-biphenylcarboxylic acid (D40)

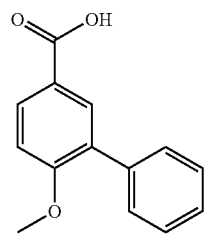

Methyl 6-(methyloxy)-3-biphenylcarboxylate (D39) (194 mg, 0.8 mmol) dissolved in 2N NaOH aq. (3 ml) and methanol (3 ml). Stirred at room temperature overnight and then the organic solvent was evaporated in vacuo. Added EtOAc/water separated and then acidified the aqueous and re-extracted. The organic extracts were dried and evaporated to afford 202 mg of the title compound as a white solid. δH (d$_6$-DMSO, 400 MHz) 3.84 (3H, s), 7.22 (1H, d), 7.33-7.49 (5H, m), 7.82 (1H, d), 7.95 (1H, dd), MS (ES$^+$): C$_{14}$H$_{12}$O$_3$ requires 228; found 229 (M+H$^+$).

Description for D41

3-Bromo-5-(5-{3-chloro-4-[(1-methylethyl)oxy]phenyl}-1,2,4-oxadiazol-3-yl)-1H-indole (D41)

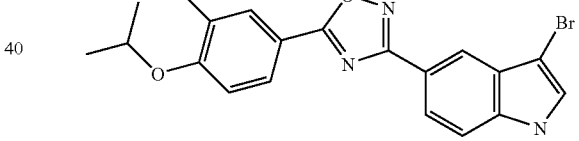

To 5-(5-{3-chloro-4-[(1-methylethyl)oxy]phenyl}-1,2,4-oxadiazol-3-yl)-1H-indole (D5) (450 mg, 1.27 mmol) dissolved in DMF (12 ml) was added bromine (213 mg, 1.35 mmol) dropwise. Stirred for 15 minutes, evaporated off the DMF, added diethyl ether (70 ml) and washed with water (2×70 ml). Dried over MgSO$_4$ and evaporated off the solvent. The residue was crystallised from diethyl ether/hexane to give 160 mg of the title compound as a white solid. δH (400 MHz, d$_6$-DMSO) 1.37 (6H, d), 4.88 (1H, sept), 7.44 (1H, d), 7.59 (1H, dd), 7.72 (1H, d), 7.91 (1H, dd), 8.13-8.32 (3H, m). MS (ES) C$_{19}$H$_{15}$$^{79}$BrClN$_3$O$_2$ requires 431; found 432 (MH$^+$).

The following esters were prepared in a similar fashion to the previously described examples (such as D6) using the appropriate indole and alkylating agent. The alkyl halides were commercially available apart from D11 used to prepare D48. Unless stated otherwise, the reactions were performed in DMF. On some occasions the reactions were worked up by an aqueous work-up procedure whilst on others the crude material was used directly in the hydrolysis step following evaporation of the reaction solvent.

| | Structure | Name | Precursor indole | Comments | MH+ |
|---|---|---|---|---|---|
| D42 | 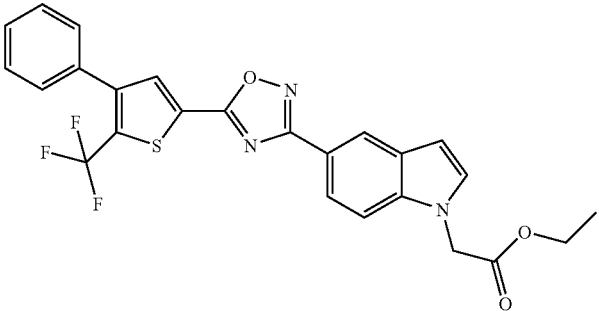 | ethyl (5-{5-[4-phenyl-5-(trifluoromethyl)-2-thienyl]-1,2,4-oxadiazol-3-yl}-1H-indol-1-yl)acetate | D2 | solvent DMPU rather than DMF. Reaction at 100-120° C. in microwave. | — |
| D43 | 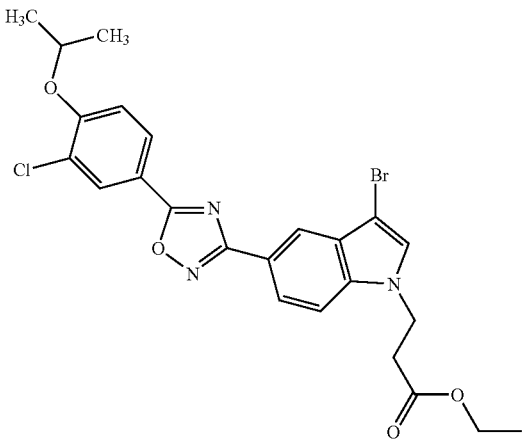 | ethyl 3-[3-bromo-5-(5-{3-chloro-4-[(1-methylethyl)oxy]phenyl}-1,2,4-oxadiazol-3-yl)-1H-indol-1-yl]propanoate | D41 | Reaction conventially heated to 80° C. | 534 for $^{81}$Br $^{35}$Cl |
| D44 | 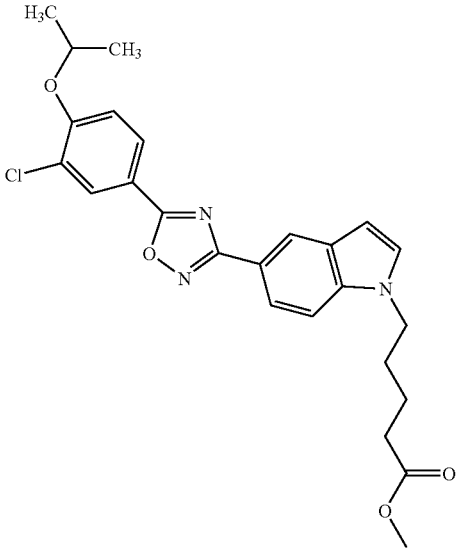 | methyl 5-[5-(5-{3-chloro-4-[(1-methylethyl)oxy]phenyl}-1,2,4-oxadiazol-3-yl)-1H-indol-1-yl]pentanoate | D5 | Reaction conventiallly heated to 80° C. | 468 |
| D45 | 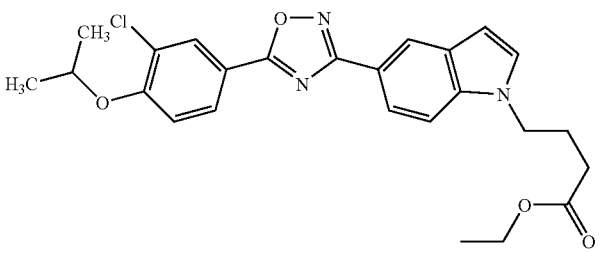 | ethyl 4-[5-(5-{3-chloro-4-[(1-methylethyl)oxy]phenyl}-1,2,4-oxadiazol-3-yl)-1H-indol-1-yl]butanoate | D5 | Reaction heated in the microwave at 130° C. Crude material used in next step following evaporation. | — |

-continued

| Structure | Name | Precursor indole | Comments | MH+ |
|---|---|---|---|---|
| D46 | methyl (2R)-3-[5-(5-{3-chloro-4-[(1-methylethyl)oxy]phenyl}-1,2,4-oxadiazol-3-yl)-1H-indol-1-yl]-2-methylpropanoate | D5 | Reaction heated in the microwave at 140° C. Crude material used in next step following evaporation. | — |
| D47 | ethyl (2S)-3-[5-(5-{3-chloro-4-[(1-methylethyl)oxy]phenyl}-1,2,4-oxadiazol-3-yl)-1H-indol-1-yl]-2-methylpropanoate | D5 | Reaction heated in the microwave at 130° C. Crude material used in next step following evaporation. | — |
| D48 | ethyl 2,2-dimethyl-3-(5-{5-[4-phenyl-5-(trifluoromethyl)-2-thienyl]-1,2,4-oxadiazol-3-yl}-1H-indol-1-yl)propanoate | D2 | Reaction heated in the microwave at 131-150° C. Crude material used in next step following evaporation. | 540 |

Description for D49

5-[3-(1H-indol-4-yl)-1,2,4-oxadiazol-5-yl]-2-[(1-methylethyl)oxy]benzonitrile (D49)

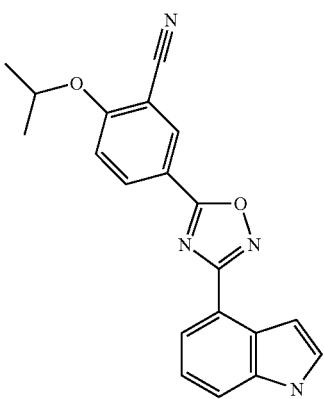

To 3-cyano-4-[(1-methylethyl)oxy]benzoic acid (can be prepared as described in WO2005/58848) (500 mg, 2.44 mmol) in DMF (15 ml) was added EDAC (514 mg, 2.67 mmol) and HOBt (367 mg, 2.67 mmol) and the solution left standing for 30 minutes. Added N-hydroxy-1H-indole-4-carboximidamide (D9) (427 mg, 2.44 mmol) and left standing for 1 hour. To the solution were added EDAC (117 mg, 0.61 mmol) and HOBt (84 mg, 0.61 mmol) and left standing for 2 hours. To the solution were added EDAC (234.9 mg, 1.22 mmol) and HOBt (167.7 mg, 1.22 mmol) and left standing overnight. Heated at 80° C. overnight, cooled and added EtOAc (30 ml). Washed with water (30 ml), sat. sodium hydrogen carbonate (30 ml) and water (30 ml). Dried over $MgSO_4$ and evaporated off the solvent. The residue was triturated with diethyl ether to give 353 mg of the title compound as a pale brown solid. $\delta$H (400 MHz, $d_6$-DMSO) 1.39 (6H, d), 4.94-5.03 (1H, m), 7.09-7.10 (1H, m), 7.30 (1H, t), 7.56-7.59 (2H, m), 7.67 (1H, d), 7.92 (1H, dd), 8.45 (1H, dd), 8.55 (1H, d), 11.52 (1H, broad s). MS (ES) $C_{20}H_{16}N_4O_2$ requires 344; found 345 (MH+).

Description for D50

Ethyl 4-[4-(5-{3-cyano-4-[(1-methylethyl)oxy]phenyl}-1,2,4-oxadiazol-3-yl)-1H-indol-1-yl]butanoate (D50)

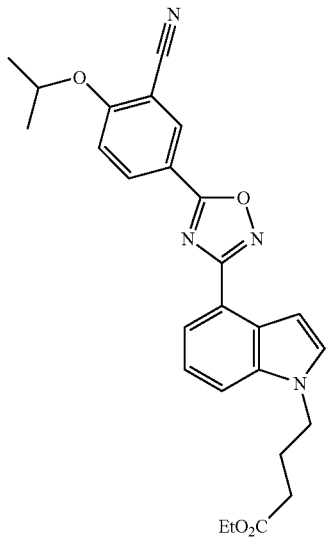

A mixture of 5-[3-(1H-indol-4-yl)-1,2,4-oxadiazol-5-yl]-2-[(1-methylethyl)oxy]benzonitrile (D49) (100 mg, 0.29 mmol), ethyl 4-bromobutyrate (85 mg, 0.44 mmol) and cesium carbonate (189 mg, 0.58 mmol) in DMF (2 ml) was heated at 80° C. for 1 hour. Added ethyl 4-bromobutyrate (85 mg, 0.44 mmol) and heated overnight at 80° C. Added ethyl 4-bromobutyrate (85 mg, 0.44 mmol) and cesium carbonate (189 mg, 0.58 mmol) and heated for 24 hours. Added ethyl 4-bromobutyrate (85 mg, 0.44 mmol) and heated for 24 hours. Added ethyl 4-bromobutyrate (85 mg, 0.44 mmol) and heated for 6 hours. Added EtOAc (20 ml) and washed with water (20 ml). Dried over MgSO$_4$ and evaporated off the solvent. The residue was crystallised from ethanol to give the title compound (55 mg) as a white solid. MS (ES) C$_{26}$H$_{26}$N$_4$O$_4$ requires 458; found 459 (MH$^+$).

Description 51

Ethyl 3-(5-cyano-1H-indol-1-yl)propanoate (D51)

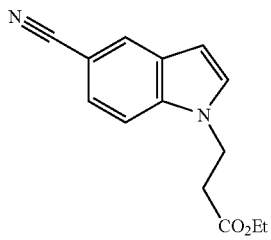

A mixture of 1H-indole-5-carbonitrile (1.42 g, 10 mmol), ethyl 3-bromopropanoate (1.92 ml, 15 mmol) and cesium carbonate (6.5 g, 20 mmol) in DMF (50 ml) was heated at 80° C. for 4 hours. Cooled the solution, added diethyl ether (300 ml) and washed with water (3×300 ml). Dried over MgSO$_4$ and evaporated off the solvent to yield 2.4 g of pale orange oil. This crude product was used in the next stage (preparation of D52).

Description for D52

Ethyl 3-{5-[(hydroxyamino)(imino)methyl]-1H-indol-1-yl}propanoate

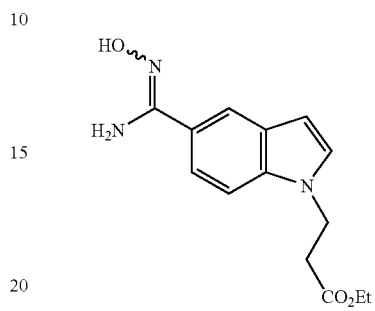

Ethyl 3-(5-cyano-1H-indol-1-yl)propanoate (D51) (1.7 g, 7.2 mmol), hydroxylamine hydrochloride (1.0 g, 14.4 mmol) and sodium hydrogen carbonate (2.42 g, 28.9 mmol) were suspended in ethanol (100 ml) and stirred at 50° C. for 3 days. A single product formed but 15% starting material remained. Cooled, filtered off the inorganic material and evaporated off the solvent. The product was crystallised from a mixture of EtOAc, diethyl ether and hexane to yield 1.9 g of the title compound as a white solid. MS (ES) C$_{14}$H$_{17}$N$_3$O$_3$ requires 275; found 276. (MH$^+$).

Description for D53

Ethyl 3-[5-(5-{3-cyano-4-[(1-methylethyl)oxy]phenyl}-1,2,4-oxadiazol-3-yl)-1H-indol-1-yl]propanoate (D53)

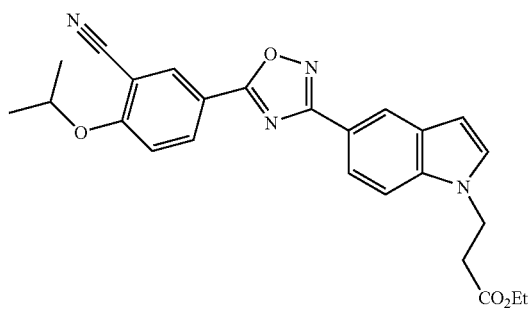

3-Cyano-4-[(1-methylethyl)oxy]benzoic acid (can be prepared as described in WO2005/58848) (215 mg, 1.05 mmol), EDAC (219 mg, 1.14 mmol) and HOBt (156 mg, 1.14 mmol) in dry DMF (10 ml) were stirred at RT for 10 minutes. Added ethyl 3-{5-[(hydroxyamino)(imino)methyl]-1H-indol-1-yl}propanoate (D52) (288 mg, 1.05 mmol) and stirred for 1 hour at RT. Heated at 80° C. for 7 hours. The solution was cooled and EtOAc (50 ml) added. Washed with water (50 ml), sat. sodium hydrogen carbonate (50 ml) and water (50 ml). Dried over MgSO$_4$ and evaporated off the solvent. The residue was crystallised from ether to yield 200 mg of the title compound as a very pale pink solid. MS (ES) C$_{25}$H$_{24}$N$_4$O$_4$ requires 444; found 445 (MH$^+$)

Description for D54

Ethyl 3-(4-cyano-1H-indol-1-yl)propanoate (D54)

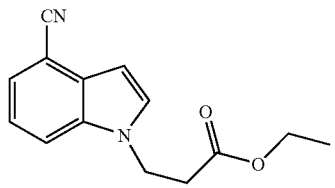

4-Cyanoindole (2.5 g) was dissolved in DMF (7.5 ml). $Cs_2CO_3$ (11.46 g) was added followed by ethyl 3-bromopropionate (3.38 ml). This mixture was heated to 80° C. for 40 minutes. A further portion of DMF (5 ml) was added and heating at 80° C. continued for 1 hour. The reaction mixture was evaporated then dissolved in $H_2O$ (200 ml) and extracted with EtOAc (200 ml). This was evaporated to give a yellow oil (3.5 g) which was purified on a 40+M Biotage cartridge, eluting with a 25-75% mixture of $Et_2O$ in hexane. This gave the title compound (3.44 g) as a pale yellow oil. δH ($CDCl_3$, 400 MHz): 1.19 (3H, t), 2.82 (2H, t), 4.12 (2H, q), 4.50 (2H, t), 6.71 (1H, d), 7.23-7.28 (1H, m), 7.33 (1H, d), 7.47 (1H, d), 7.60 (1H, dd). MS (ES): $C_{14}H_{14}N_2O_2$ requires 242; found 243 ($MH^+$).

The following example was prepared by a similar method to those described above. The reaction was not complete after the work-up and so the material was resubmitted to the reaction conditions with an extra 0.2 equivalents of base and alkylating agent and the product was purified by trituration with ether.

| Number | Structure | Name | $MH^+$ |
| --- | --- | --- | --- |
| D55 | 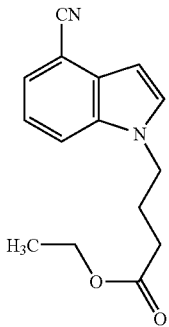 | ethyl (4-cyano-1H-indol-1-yl)acetate | 229 |

Description for D56

Ethyl 4-(4-cyano-1H-indol-1-yl)butanoate (D56)

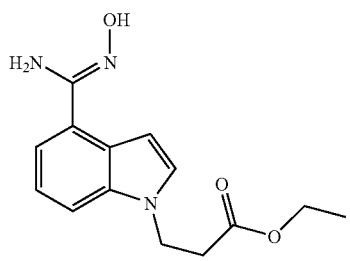

Combined 4-cyanoindole (5 g, 35.2 mmol), ethyl-4-bromobutanoate (10.29 g, 52.8 mmol) and cesium carbonate (22.92 g, 70.3 mmol) and heated to 80° C. under argon for 1 hour. The reaction was allowed to cool and then 150 ml diethyl ether was added and the organic solution was washed with 3×150 ml $H_2O$. Dried the organic solution over $MgSO_4$ and evaporated the solvent. Dried on high vacuum over the weekend to afford the title compound (8.25 g) as an orange oil. δH (400 MHz, $d_6$-DMSO). 1.13 (3H, t), 1.96-2.05 (2H, m), 2.26 (2H, t), 3.99 (2H, q), 4.29 (2H, t), 6.60 (1H, dd), 7.29 (1H, apparent t), 7.55 (1H, dd), 7.68 (1H, d), 7.90 (1H, d). MS (ES): $C_{15}H_{16}N_2O_2$ requires 256; found 257 ($MH^+$).

Description for D57

Ethyl 3-{4-[(hydroxyamino)(imino)methyl]-1H-indol-1-yl}propanoate (D57)

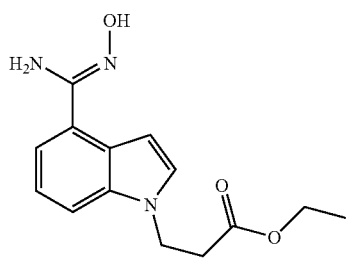

Ethyl 3-(4-cyano-1H-indol-1-yl)propanoate (D54) (3.44 g), $NH_2OH.HCl$ (1.97 g) and $Na_2CO_3$ (5.96 g) were dissolved in EtOH (75 ml). This mixture was heated at 50° C. overnight. A further portion of $NH_2OH.HCl$ (985 mg) was added and the mixture stirred at 70° C. overnight. The reaction mixture was then filtered and evaporated to give the title compound (4.06 g). MS (ES): $C_{14}H_{17}N_3O_3$ requires 275; found 276 ($MH^+$)

Description for D57 Alternative Procedure

Ethyl 3-{4-[(hydroxyamino)(imino)methyl]-1H-indol-1-yl}propanoate (D57)

A mixture of 1H-indole-4-carbonitrile (3.4 g, 23.92 mmol), ethyl 3-bromopropanoate (4.57 ml, 35.9 mmol) and cesium carbonate (15.59 g, 47.8 mmol) was heated at 80° C. for 2 hours and left standing overnight. Ether (400 ml) was added and the resulting mixture was washed with water (3×400 ml), dried over $MgSO_4$ and evaporated to yield 6.6 g of pale yellow clear oil The oil N4111-30-A2 (6.6 g, 27.2 mmol), hydroxylamine hydrochloride (3.79 g, 54.5 mmol) and sodium bicarbonate (9.15 g, 109 mmol) in ethanol were stirred at 50° C. overnight. Added further hydroxylamine hydrochloride (2.3 g) and heated at 50° C. for 24 hours. The reaction was filtered and residue washed with DCM (50 ml). The solvent was removed by evaporation and the residue triturated with hexane to obtain the title compound (4.2 g) as a white solid. Further title compound (1.0 g) as a white solid was obtained from trituration of residues. Mass spectral data consistent with previous synthesis.

The following was made in a similar fashion to the first D57 procedure listed, sodium bicarbonate was the base used and the reaction was carried out at 55° C.

| Number | Structure | precursor number | Name | MH+ |
|---|---|---|---|---|
| D58 | 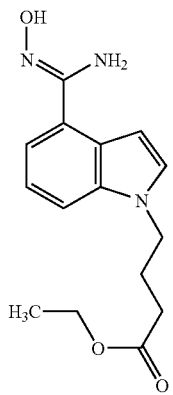 | D55 | ethyl {4-[(hydroxyamino)(imino)methyl]-1H-indol-1-yl}acetate | 262 |

Description for D59

Ethyl 4-{4-[(hydroxyamino)(imino)methyl]-1H-indol-1-yl}butanoate (D59)

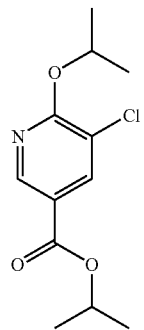

Ethyl 4-(4-cyano-1H-indol-1-yl)butanoate (D56) (8.25 g, 32.2 mmol) was dissolved in EtOH and treated with NH$_2$OH.HCl (4.47 g, 64.4 mmol) and NaHCO$_3$ (8.11 g, 97 mmol) and heated to 55° C. for 1 day and two nights. Further NH$_2$OH.HCl (500 mg) and NaHCO$_3$ (500 mg) were added and the reaction was heated for another 3 hours and then separated the inorganics by filtration, washing well with EtOH. The solvent was evaporated and the residue dried under high vacuum. Trituration with ether and dcm afforded two batches of the title compound N2668-20-A8 (5.14 g) and N2668-20-A9 (976 mg). δH (400 MHz, d$_6$-DMSO) 1.15 (3H, t), 1.98 (2H, apparent quin), 2.25 (2H, t), 4.03 (2H, q), 4.21 (2H, t), 5.73 (2H, br s), 6.82 (1H, dd), 7.15 (1H, apparent t), 7.27 (1H, dd), 7.35 (1H, d), 7.51 (1H, d), 9.58 (1H, br s). MS (ES): C$_{15}$H$_{19}$N$_3$O$_3$ requires 289; found 290 (MH+).

Description for D60

1-Methylethyl 5-chloro-6-[(1-methylethyl)oxy]-3-pyridinecarboxylate (D60)

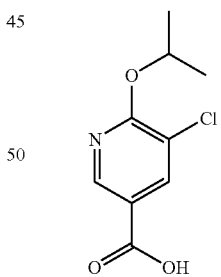

The 5-chloro-6-hydroxy-3-pyridinecarboxylic acid (1 g, 5.76 mmol) was suspended in toluene (200 ml) and treated with silver carbonate (3.97 g, 14.40 mmol) and 2-iodopropane (3.46 ml, 34.6 mmol) and stirred at RT in the dark for 3 days. LC/MS showed 2/3 product. Added 2-iodopropane (3 ml) and stirred for 24 hours. LC/MS showed 80% product. Added EtOAc (200 ml) and washed with water (200 ml)+sat. NaHCO$_3$ (50 ml) followed by water (200 ml). Dried over MgSO$_4$ and evaporated off the solvent to yield 1.0 g of the title compound as a clear, colourless oil. MS (ES+) C$_{12}$H$_{16}$$^{35}$ClNO$_3$ requires 257; found 257.

Description for D61

5-Chloro-6-[(1-methylethyl)oxy]-3-pyridinecarboxylic acid (D61)

1-methylethyl 5-chloro-6-[(1-methylethyl)oxy]-3-pyridinecarboxylate (D60) (1.6 g, 6.21 mmol) in isopropanol (70 ml) and water (35.0 ml) was treated with 2N sodium hydroxide (6.21 ml, 12.42 mmol) and stirred for 3 hours to give a single product. Evaporated off the IPA, acidified with glacial acetic acid and extracted product into EtOAc (100 ml). Dried over MgSO$_4$ and evaporated off the solvent to yield 1.30 g of the title compound as a white solid. MS (ES) C$_9$H$_{10}$$^{35}$ClNO$_3$ requires 215; found 214 (M−H+).

Description for D62

Ethyl 3-[4-(5-{5-chloro-6-[(1-methylethyl)oxy]-3-pyridinyl}-1,2,4-oxadiazol-3-yl)-1H-indol-1-yl]propanoate (D62)

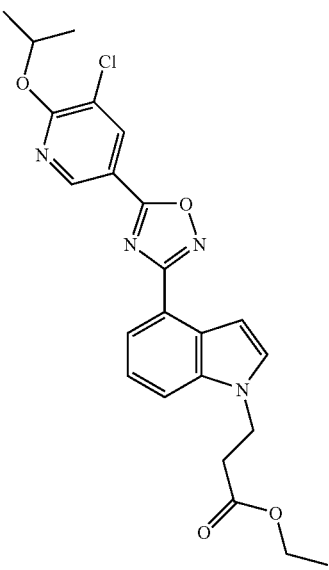

To 5-chloro-6-[(1-methylethyl)oxy]-3-pyridinecarboxylic acid (D61) (1.504 g, 6.97 mmol) in dry DMF (30 ml) was added EDC (1.604 g, 8.37 mmol) and HOBT (1.282 g, 8.37 mmol). Stirred solution at RT for 10 minutes then added ethyl 3-{4-[(hydroxyamino)(imino)methyl]-1H-indol-1-yl}propanoate (N4111-31-A4) (D57) (1.92 g, 6.97 mmol). The mixture was stirred for 30 minutes. LC/MS showed one product (intermediate). The solution was heated at 80° C. for 2 hours. Left standing overnight at RT then heated 80° C. for further 2 hours to give complete reaction. Cooled and added EtOAc (250 ml). The EtOAc was washed with sat. $NaHCO_3$ (150 ml) followed by water (2×200 ml). Dried over $MgSO_4$ and evaporated off the solvent. The residue was subjected to chromatography on the biotage (EtOAc/hexane 1:2). On evaporation of most of the solvent from clean fractions and addition of hexane a white precipitate was formed. The solid was filtered off to obtain 1.1 g of the title product. MS (ES) $C_{23}H_{23}{}^{35}ClN_4O_4$ requires 454; found 455 (MH+).

Description for D63

Ethyl 3-[4-(5-{3-cyano-4-[(1-methylethyl)oxy]phenyl}-1,2,4-oxadiazol-3-yl)-1H-indol-1-yl]propanoate (D63)

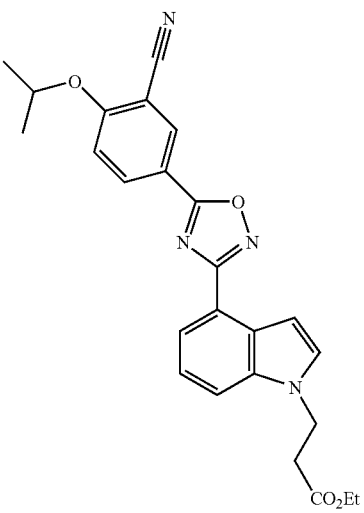

The 3-cyano-4-[(1-methylethyl)oxy]benzoic acid (can be prepared as described in WO2005/58848) (113 mg, 0.55 mmol), EDAC (115 mg, 0.60 mmol) and HOBt (82 mg, 0.60 mmol) were dissolved in DMF (5 ml) and left standing for 15 minutes. Added ethyl 3-{4-[(hydroxyamino)(imino)methyl]-1H-indol-1-yl}propanoate (D57) (150 mg, 0.55 mmol) and stood overnight at RT. Heated solution at 80° C. for 2 hours. LC/MS showed mostly product. After heating for a few more hours there was no change. Added EtOAc (20 ml) and washed with water (30 ml). Washed with saturated sodium hydrogen carbonate (30 ml) and water (2×30 ml). Dried over $MgSO_4$ and evaporated off the solvent to obtain 81 mg of the title compound as a pale brown solid. MS (ES) $C_{25}H_{44}N_4O_4$ requires 444; found 445 (MH+).

Description for D64

Ethyl 3-(4-{5-[2-(trifluoromethyl)-4-biphenylyl]-1,2,4-oxadiazol-3-yl}-1H-indol-1-yl)propanoate (D64)

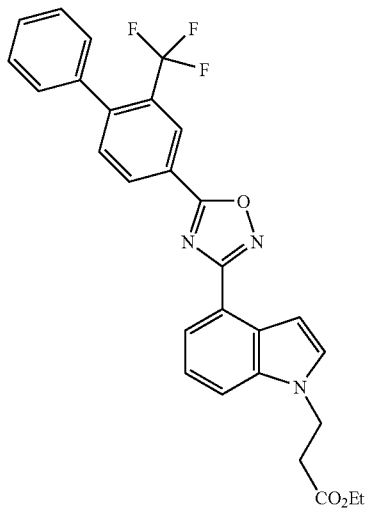

To 2-(trifluoromethyl)-4-biphenylcarboxylic acid (D29) (146 mg, 0.55 mmol) in DMF (5 ml) was added EDC (115 mg, 0.60 mmol) and HOBt (82 mg, 0.60 mmol) and the solution left standing for 15 minutes. Added ethyl 3-{4-[hydroxyamino)(imino)methyl]-1H-indol-1-yl}propanoate (D57) (150 mg, 0.55 mmol) and stirred at RT for 1 hour. Heated at 80° C. for 1 hour then heated overnight. Cooled then added EtOAc (20 ml). Washed with water (20 ml), sat aqueous sodium hydrogen carbonate (20 ml) and water (20 ml). Dried over MgSO$_4$ then evaporated of the solvent. The residue was triturated with ethanol to give 157 mg of the title compound as a white solid. δH (400 MHz, d$_6$-DMSO) 1.11 (3H, t), 2.90 (2H, t), 4.02 (2H, q), 4.55 (2H, t), 7.10 (1H, d), 7.32-7.48 (3H, m), 7.49-7.61 (3H, m), 7.61 (1H, d), 7.73-7.84 (2H, m), 8.00 (1H, d), 8.53-8.56 (2H, m). MS (ES) C$_{28}$H$_{22}$F$_3$N$_3$O$_3$ requires 505; found 506 (MH$^+$).

Description for D65 Alternative to Description for D50

Ethyl 4-[4-(5-{3-cyano-4-[(1-methylethyl)oxy]phenyl}-1,2,4-oxadiazol-3-yl)-1H-indol-1-yl]butanoate (D65)

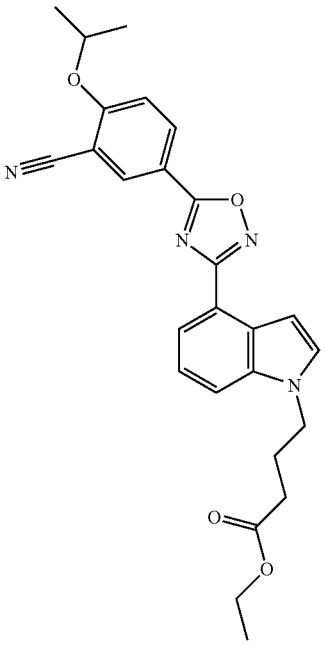

A mixture of 3-cyano-4-[(1-methylethyl)oxy]benzoic acid (can be prepared as described in WO2005/58848) (1.21 g, 5.88 mmol), EDC (1.35 g, 7.05 mmol) and HOBt (1.08 g, 7.05 mmol) in dry DMF (85 ml) was stirred for 20 minutes at RT. Added ethyl 4-{4-[(hydroxyamino)(imino)methyl]-1H-indol-1-yl}butanoate (D59) (1.70 g, 5.88 mmol) and stirred at RT for 1 hour. Heated mixture at 80° C. for 5 hours and left overnight at RT. Heated at 80° C. for 6 hours then evaporated off the DMF. Added EtOAc (200 ml) and washed with sat. NaHCO$_3$ (200 ml) and water (200 ml). Dried over MgSO$_4$ and evaporated off the solvent. Subjected the residue to chromatography using the biotage (EtOAc/hexane 1:2) and evaporated the cleanest fractions to yield 1.42 g the title compound as a white solid. δH (400 MHz, d$_6$-DMSO) 1.15 (3H, t), 1.39 (6H, d), 2.04 (2H, apparent quintet), 2.24 (2H, t), 4.00 (2H, q), 4.31 (2H, t), 4.94-5.04 (1H, m), 7.10 (1H, dd), 7.31 (1H, t), 7.56-7.60 (2H, m), 7.77 (1H, d), 7.95 (1H, d), 8.45 (1H, dd), 8.56 (1H, d). MS (ES) C$_{26}$H$_{26}$N$_4$O$_4$ requires 458; found 459 (MH$^+$).

Description for D66

4-(1-Cyclohexen-1-yl)-3-(trifluoromethyl)benzamide (D66)

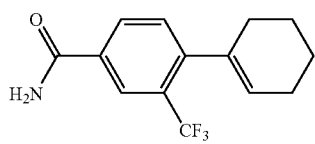

4-bromo-3-(trifluoromethyl)benzonitrile (commercial) (1.2 g, 4.80 mmol), 1-cyclohexen-1-ylboronic acid (0.907 g, 7.20 mmol), sodium methoxide (0.778 g, 14.40 mmol) and bis(triphenylphosphine)palladium(II) chloride (0.337 g, 0.480 mmol) were added to dry methanol (12 mL) and the mixture heated in the microwave at 80° C. for 10 minutes. The reaction mixture was partitioned between ethyl acetate (40 mL) and water (40 mL) and then the organic phase washed with further water (40 mL). The organic phase was dried (MgSO$_4$), filtered and the solvent removed in vacuo. The crude product was purified by flash silica chromatography, eluting with 0-75% ethyl acetate in hexane to give the title compound as a white solid (1.02 g). δH (CDCl$_3$, 400 MHz): 8.09 (1H, m), 7.90 (1H, dd), 7.32 (1H, d), 6.3-5.8 (2H, m) 5.61 (1H, s), 2.25-2.13 (4H, m), 1.80-1.60 (4H, m). MS (ES): C$_{14}$H$_{14}$F$_3$NO requires 269; found 270 (MH$^+$).
Description for D67

GSK1929583A, N2123-11-A2

4-Cyclohexyl-3-(trifluoromethyl)benzamide (D67)

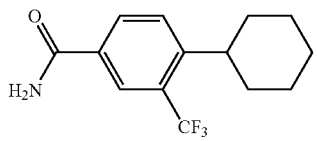

4-(1-Cyclohexen-1-yl)-3-(trifluoromethyl)benzamide (D66) (850 mg, 3.16 mmol) was dissolved in methanol (63 ml) and hydrogenated using an H-Cube, using palladium on carbon at 40° C. with a flow rate of 2 mL/min. The solvent was removed in vacuo to give the title compound as a white solid (822 mg). δH (CDCl$_3$, 400 MHz): 8.08 (1H, d), 7.94 (1H, dd), 7.52 (1H, d), 6.54 (2H, brs), 2.97 (1H, m), 1.90-1.75 (5H, m), 1.50-1.22 (5H, m). MS (ES): C$_{14}$H$_{16}$F$_3$NO requires 271; found 272 (MH$^+$).
Description for D68

4-Cyclohexyl-3-(trifluoromethyl)benzoic acid (D68)

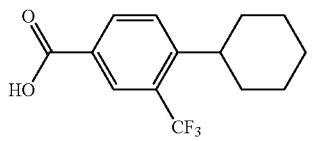

To a solution of 4-cyclohexyl-3-(trifluoromethyl)benzamide (D67) (822 mg, 3.03 mmol) in ethanol (40 ml) was added potassium hydroxide (1.700 g, 30.3 mmol) and water (5 ml) and the reaction heated to 90° C. block temperature for 3 h and stirred at room temperature for 16 h. Further potassium hydroxide (1.700 g, 30.3 mmol) was added and the reaction heated at reflux for 27 h. A further 5 mL of water was added and the reaction heated for 66 hours (weekend). The reaction mixture was concentrated in vacuo and the residue partitioned between ethyl acetate (25 mL) and aqueous hydrochloric acid (2M, 25 mL). The aqueous layer was further extracted with ethyl acetate (25 mL) and the combined organic phases dried (MgSO$_4$), filtered and the solvent removed in vacuo to give the title compound as a white solid (737 mg). δH (methanol-d$_4$, 400 MHz): 8.24 (1H, d), 8.18 (1H, dd), 7.68 (1H, d), 2.98 (1H, t), 1.72-1.95 (5H, m), 1.30-1.58 (5H, m). MS (ES): C$_{14}$H$_{15}$F$_3$O$_2$ requires 272; found 271 (M−H$^+$).

Description for D69

Ethyl 3-(4-{5-[4-cyclohexyl-3-(trifluoromethyl)phenyl]-1,2,4-oxadiazol-3-yl}-1H-indol-1-yl)propanoate (D69)

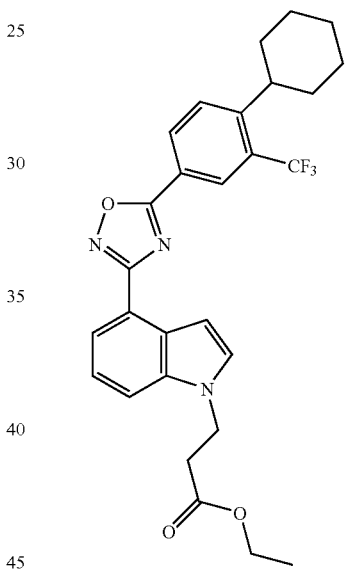

A solution of 4-cyclohexyl-3-(trifluoromethyl)benzoic acid (D68) (148 mg, 0.545 mmol), EDC (115 mg, 0.599 mmol) and HOBt (92 mg, 0.599 mmol) in DMF (5 ml) was stirred for 10 min before addition of ethyl 3-{4-[((hydroxyamino)(imino)methyl]-1H-indol-1-yl}propanoate (D57) (150 mg, 0.545 mmol). The reaction was stirred for 30 min at room temperature followed by 16 h at 80° C. The reaction mixture was partitioned between ethyl acetate (25 mL) and water (25 mL) and the organic phase washed with aqueous sodium bicarbonate (25 mL) and then water (25 mL). The organic phase was dried (phase separator) and the solvent removed in vacuo. The crude product was purified by MDAP. Some of the mixture submitted for MDAP had precipitated and was triturated with ethanol and filtered. The white solids were combined to give the title compound (63 mg). MS (ES): C$_{28}$H$_{28}$F$_3$N$_3$O$_3$ requires 511; found 512 (MH$^+$).

Description for D70

1-Methylethyl 4-[(1-methylethyl)oxy]-3-(trifluoromethyl)benzoate (D70)

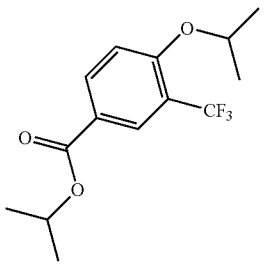

A mixture of 4-hydroxy-3-(trifluoromethyl)benzoic acid (commercial) (450 mg, 2.18 mmol), 2-iodopropane (435 µL, 4.36 mmol) and potassium carbonate (603 mg, 4.36 mmol) in N,N'-dimethylformamide (40 mL) was heated at 70° C. for 4 h before further 2-iodopropane (218 µL, 2.18 mmol) was added and the heating continued for 18 h. The inorganic solid was filtered off and rinsed with ethyl acetate. The filtrate was concentrated in vacuo and partitioned between ethyl acetate (150 mL) and water (150 mL) containing some aqueous sodium hydroxide. The organic layer was dried (phase separator) and concentrated in vacuo to give the crude title compound (704 mg) as a yellow oil. MS (ES): $C_{14}H_{17}F_3O_3$ requires 290; found 291 ($MH^+$).

Description for D71

4-[(1-Methylethyl)oxy]-3-(trifluoromethyl)benzoic acid (D71)

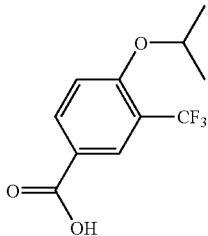

To a mixture of 1-methylethyl 4-[(1-methylethyl)oxy]-3-(trifluoromethyl)benzoate (D70) (704 mg, 2.43 mmol) in ethanol (110 mL) was added aqueous sodium hydroxide (2M, 12.2 mL, 24.3 mmol) and the reaction heated to reflux for 1 h. The mixture was concentrated in vacuo and the residue partitioned between ethyl acetate (100 mL) and water (100 mL) and acidified with aqueous hydrochloric acid (2M, 13 mL). The aqueous layer was extracted further with ethyl acetate (100 mL) and the combined organic layers dried and concentrated in vacuo to give the title compound as a yellow solid (563 mg). δH (methanol-$d_4$, 400 MHz): 8.21-8.17 (2H, m), 7.26 (1H, d), 4.84 (1H, septet), 1.38 (6H, d). MS (ES): $C_{11}H_{11}F_3O_3$ requires 248; found 247 ($M-H^+$).

Description for D72

Ethyl 3-(4-{5-[4-[(1-methylethyl)oxy]-3-(trifluoromethyl)phenyl]-1,2,4-oxadiazol-3-yl}-1H-indol-1-yl) propanoate (D72)

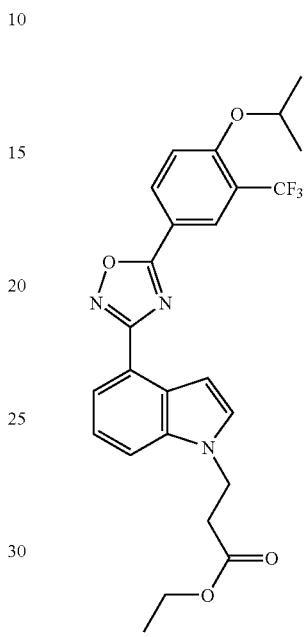

4-[(1-Methylethyl)oxy]-3-(trifluoromethyl)benzoic acid (D71) (136 mg, 0.55 mmol), EDC (116 mg, 0.61 mmol) and HOBt (82 mg, 0.61 mmol) were stirred in N,N-dimethylformamide (5 mL) for 20 min. Ethyl 3-{-4-[(hydroxyamino)(imino)methyl]-1H-indol-1-yl}propanoate (D57) (150 mg, 0.55 mmol) was added and the reaction stirred at room temperature for 3 h and then 80° C. for 18 h. The reaction mixture was partitioned between ethyl acetate (25 mL) and water (25 mL). The organic layer was washed with aqueous sodium bicarbonate (25 mL) and water (25 mL) before it was dried (phase separator), filtered and concentrated in vacuo. The residue was triturated with ethanol to give the title compound (85 mg). δH ($d_6$-DMSO, 400 MHz): 8.44 (1H, dd), 8.35 (1H, d), 7.95 (1H, d), 7.81 (1H, d), 7.62-7.58 (2H, m), 7.36 (1H, app. t), 7.07 (1H, d), 4.99 (1H, septet), 4.54 (2H, t), 4.02 (2H, q), 2.89 (2H, t), 1.36 (6H, d), 1.11 (3H, t). MS ($ES^+$): $C_{26}H_{24}F_3N_3O_4$ requires 487; found 488 ($MH^+$).

The following examples were prepared in a similar fashion to those described above. On occasion additional EDAC was required (up to 2.6 equiv) and in the case of D80 it was necessary to elevate the temperature to 120° C. Workup was either aqueous or alternatively the solvent was removed in vacuo. In the case of D92 ethanol was added to the reaction mixture and the resultant precipitate was filtered. The compounds were purified either by trituration, MDAP, normal or reversed phase chromatography.

| | Structure | Precursors | Name | MH⁺ |
|---|---|---|---|---|
| D73 | 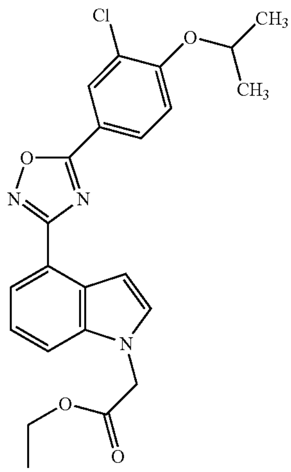 | D58 & D4 | ethyl [4-(5-{3-chloro-4-[(1-methylethyl)oxy]phenyl}-1,2,4-oxadiazol-3-yl)-1H-indol-1-yl]acetate | 440/442 |
| D74 | 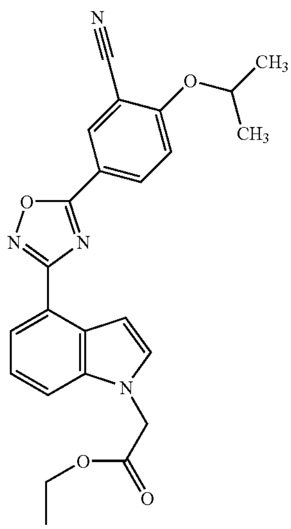 | D58 | ethyl [4-(5-{3-cyano-4-[(1-methylethyl)oxy]phenyl}-1,2,4-oxadiazol-3-yl)-1H-indol-1-yl]acetate | 431 |
| D75 | 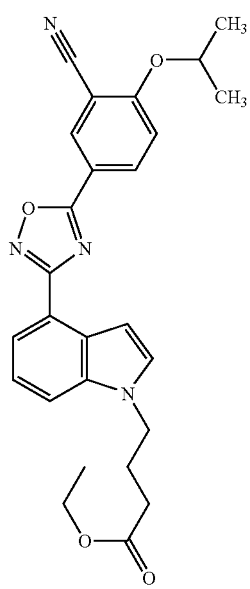 | D59 | ethyl 4-[4-(5-{3-cyano-4-[(1-methylethyl)oxy]phenyl}-1,2,4-oxadiazol-3-yl)-1H-indol-1-yl]butanoate | 459 |

-continued
| | Structure | Precursors | Name | MH+ |
|---|---|---|---|---|
| D76 | 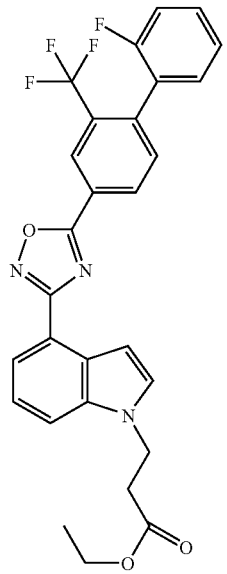 | D57 & D30 | ethyl 3-(4-{5-[2'-fluoro-2-(trifluoromethyl)-4-biphenylyl]-1,2,4-oxadiazol-3-yl}-1H-indol-1-yl)propanoate | 524 |
| D77 | 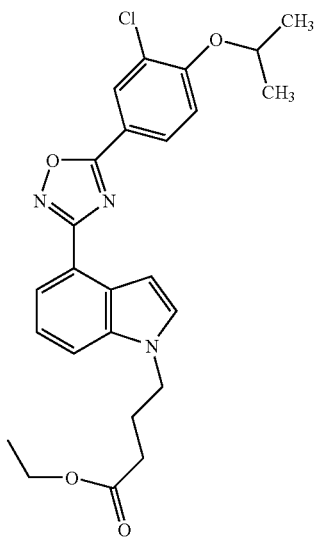 | D59 & D4 | ethyl 4-[4-(5-{3-chloro-4-[(1-methylethyl)oxy]phenyl}-1,2,4-oxadiazol-3-yl)-1H-indol-1-yl]butanoate | 468 |

-continued
| | Structure | Precursors | Name | MH+ |
|---|---|---|---|---|
| D78 | 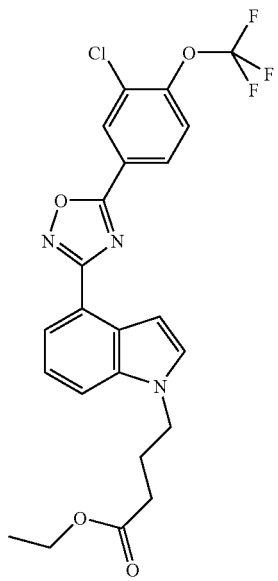 | D59 | ethyl 4-[4-(5-{3-chloro-4-[(trifluoromethyl)oxy]phenyl}-1,2,4-oxadiazol-3-yl)-1H-indol-1-yl]butanoate | 494 |
| D79 | 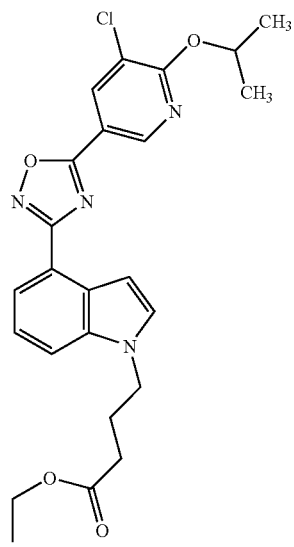 | D59 & D61 | ethyl 4-[4-(5-{5-chloro-6-[(1-methylethyl)oxy]-3-pyridinyl}-1,2,4-oxadiazol-3-yl)-1H-indol-1-yl]butanoate | 469 |

-continued
| | Structure | Precursors | Name | MH+ |
|---|---|---|---|---|
| D80 | 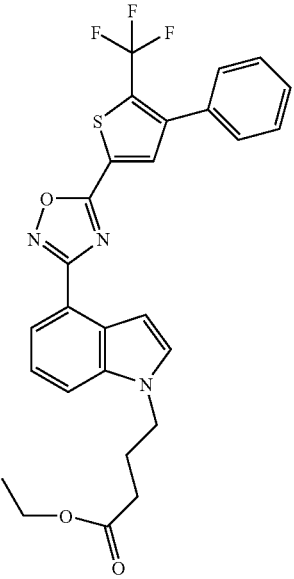 | D59 | ethyl 4-(4-{5-[4-phenyl-5-(trifluoromethyl)-2-thienyl]-1,2,4-oxadiazol-3-yl}-1H-indol-1-yl)butanoate | 526 |
| D81 | 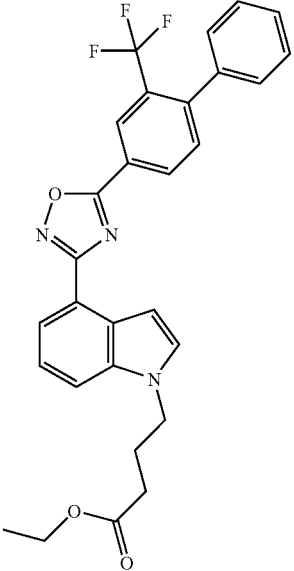 | D59 & D29 | ethyl 4-(4-{5-[2-(trifluoromethyl)-4-biphenylyl]-1,2,4-oxadiazol-3-yl}-1H-indol-1-yl)butanoate | 520 |
| D82 | 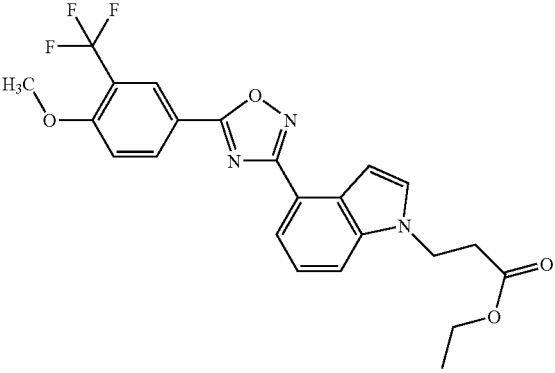 | D57 | ethyl 3-(4-{5-[4-(methyloxy)-3-(trifluoromethyl)phenyl]-1,2,4-oxadiazol-3-yl}-1H-indol-1-yl)propanoate | 460 |

-continued
| | Structure | Precursors | Name | MH+ |
|---|---|---|---|---|
| D83 | 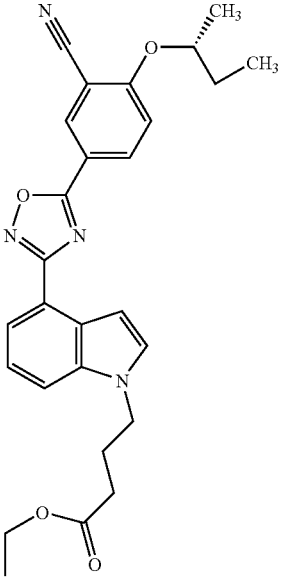 | D59 & D38 | ethyl 4-{4-[5-(3-cyano-4-{[(1R)-1-methylpropyl]oxy}phenyl)-1,2,4-oxadiazol-3-yl]-1H-indol-1-yl}butanoate | 473 |
| D84 | 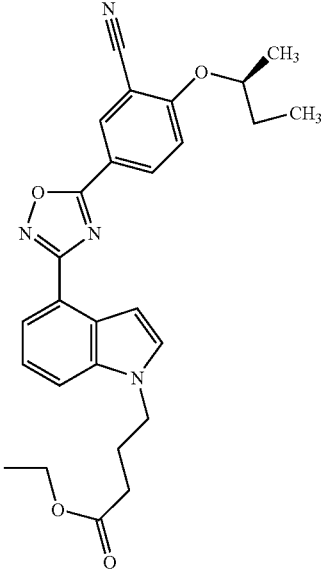 | D59 & D36 | ethyl 4-{4-[5-(3-cyano-4-{[(1S)-1-methylpropyl]oxy}phenyl)-1,2,4-oxadiazol-3-yl]-1H-indol-1-yl}butanoate | 473 |
| D85 | 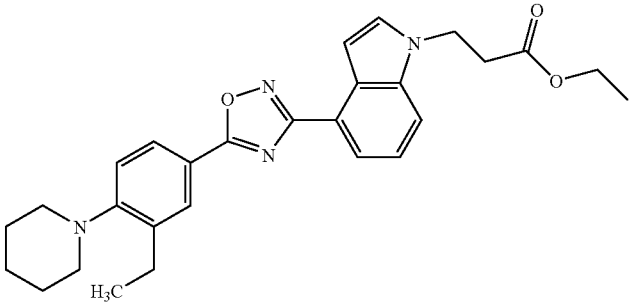 | D57 & D13 | ethyl 3-(4-{5-[3-ethyl-4-(1-piperidinyl)phenyl]-1,2,4-oxadiazol-3-yl}-1H-indol-1-yl)propanoate | 473 |

-continued

| | Structure | Precursors | Name | MH+ |
|---|---|---|---|---|
| D86 | 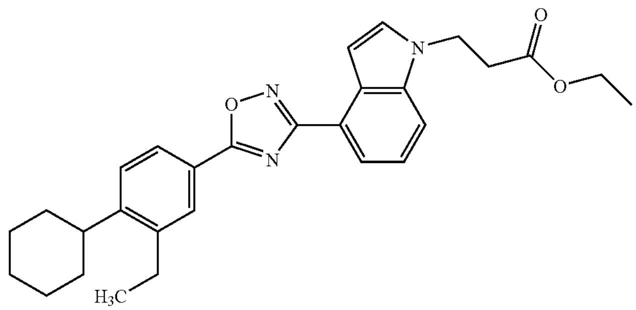 | D57 & D19 | ethyl 3-{4-[5-(4-cyclohexyl-3-ethylphenyl)-1,2,4-oxadiazol-3-yl]-1H-indol-1-yl}propanoate | 472 |
| D87 | 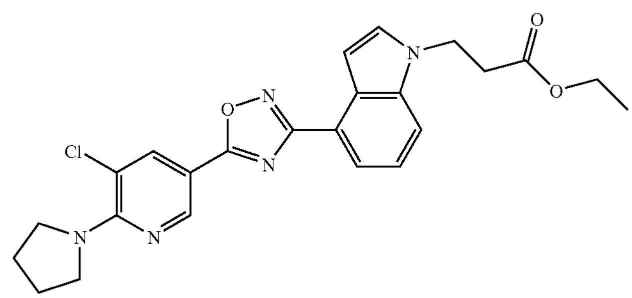 | D57 & D15 | ethyl 3-(4-{5-[5-chloro-6-(1-pyrrolidinyl)-3-pyridinyl]-1,2,4-oxadiazol-3-yl}-1H-indol-1-yl)propanoate | 466 |
| D88 | 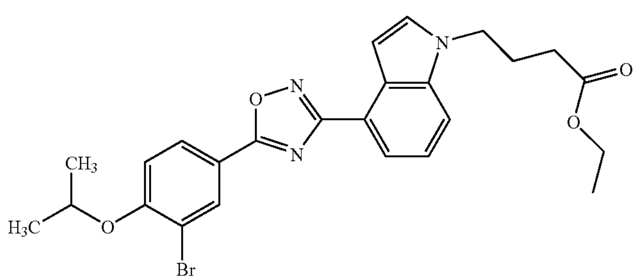 | D59 & D21 | ethyl 4-[4-(5-{3-bromo-4-[(1-methylethyl)oxy]phenyl}-1,2,4-oxadiazol-3-yl)-1H-indol-1-yl]butanoate | 512 |
| D89 | 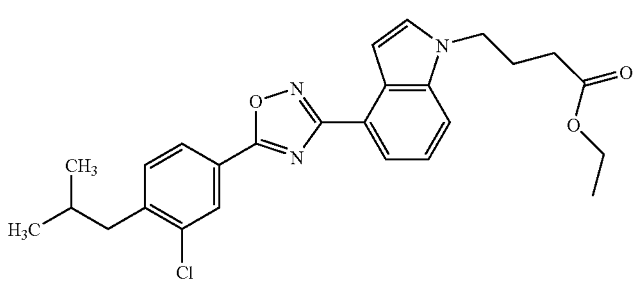 | D59 & D24 | ethyl 4-(4-{5-[3-chloro-4-(2-methylpropyl)phenyl]-1,2,4-oxadiazol-3-yl}-1H-indol-1-yl)butanoate | 466 |

-continued
| | Structure | Precursors | Name | MH+ |
|---|---|---|---|---|
| D90 | 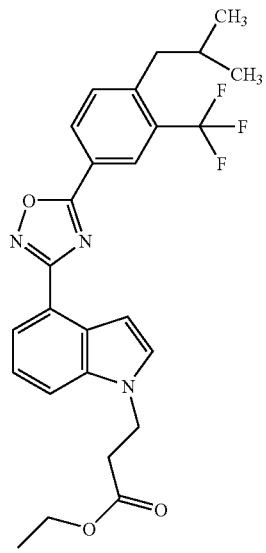 | D57 & D34 | ethyl 3-(4-{5-[4-(2-methylpropyl)-3-(trifluoromethyl)phenyl]-1,2,4-oxadiazol-3-yl}-1H-indol-1-yl)propanoate | 486 |
| D91 | 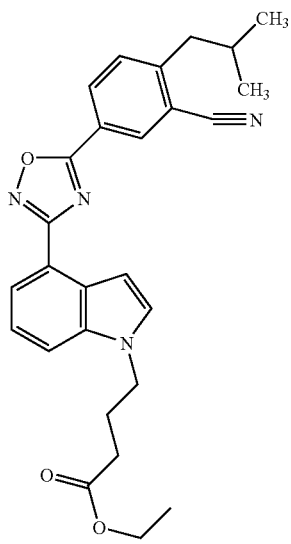 | D59 & D32 | ethyl 4-(4-{5-[3-cyano-4-(2-methylpropyl)phenyl]-1,2,4-oxadiazol-3-yl}-1H-indol-1-yl)butanoate | 457 |

| Structure | Precursors | Name | MH+ |
|---|---|---|---|
| D92 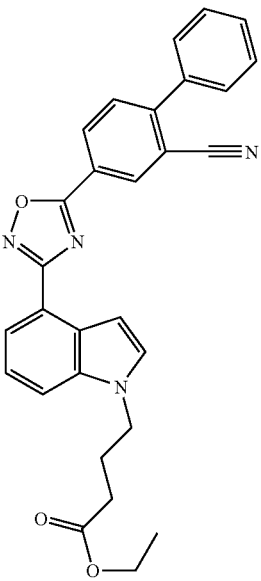 | D59 & D27 | ethyl 4-{4-[5-(2-cyano-4-biphenylyl)-1,2,4-oxadiazol-3-yl]-1H-indol-1-yl}butanoate | 477 |

Description for D93

3-Chloro-4-{5-[4-phenyl-5-(trifluoromethyl)-2-thienyl]-1,2,4-oxadiazol-3-yl}-1H-indole (D93)

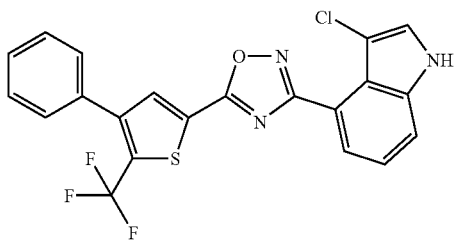

This material was prepared in a similar fashion to D7 (CQ107723-108A2) from D10 except that the reaction was stirred for four hours rather than overnight. MS (ES): $C_{21}H_{11}ClF_3N_3OS$ requires 445; found 446 (MH+).

Description for D94

3-Chloro-1H-indole-5-carbonitrile (D94)

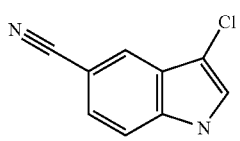

To a solution of 5-cyanoindole (3.0 g, 21 mmol) in dry DMF (50 ml) was added N-chlorosuccinimide (2.94 g, 22 mmol) and the solution stirred at room temperature for 1 hour. The solution was left standing over the weekend. LC/MS showed a single product. Added ethyl acetate (150 ml) and diethyl ether (50 ml) and washed with water (3×300 ml). Dried over MgSO₄ and evaporated off the solvent to yield 3.9 g of the title compound as a pale yellow solid. δH (400 MHz, d₆-DMSO) 7.54 (1H, dd), 7.61 (1H, dd), 7.78 (1H, d), 8.01-8.02 (1H, m), 12.2 (1H, broad s). MS (from LCMS of reaction mixture) (ES):$C_9H_5ClN_2$ requires 176; found 177 (MH+).

Description for D95

Ethyl 3-(3-chloro-5-cyano-1H-indol-1-yl)propanoate (D95)

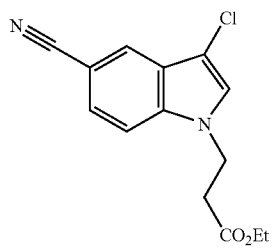

A mixture of 3-chloro-1H-indole-5-carbonitrile (D94) (1.8 g, 10 mmol), ethyl-3-bromopropionate (1.92 ml, 15 mmol), cesium carbonate (6.5 g, 20 mmol) and DMF (50 ml) was heated at 80° C. for 4 hours to give complete reaction. After allowing mixture to cool to room temperature diethyl ether (300 ml) was added and the solution washed with water (3×300 ml). Dried over MgSO₄ and evaporated off the solvent to give a brown solid. The solid was triturated with a mixture of diethyl ether and hexane to obtain 2.5 g of the title compound as a tan solid. Crude product used in the next stage (synthesis of D96).

Description for D96

Ethyl 3-{3-chloro-5-(hydroxyamino)(imino)methyl]-1H-indol-1-yl}propanoate (D96)

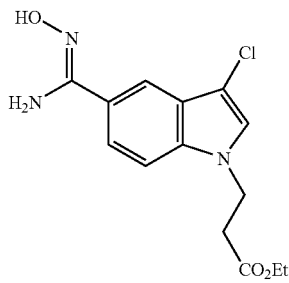

A mixture of ethyl 3-(3-chloro-5-cyano-1H-indol-1-yl)propanoate (D95) (2.0 g, 7.2 mmol), hydroxylamine hydrochloride (1.0 g, 14.4 mmol), sodium hydrogen carbonate (2.42 g, 28.9 mmol) and ethanol (100 ml) was heated at 50° C. over the weekend. Still 25% starting material present by LC/MS. Added hydroxylamine hydrochloride (0.5 g, 7.2 mmol) and sodium hydrogen carbonate (1.2 g, 14.3 mmol) and heated at 50° C. for 24 hours. There was only a small amount of starting material present so it was decided to work up the reaction. The inorganic material was filtered off. The solvent was evaporated and the residue triturated using ethyl acetate and diethyl ether to yield 1.9 g of the title compound as a pale yellow solid. MS (ES) $C_{14}H_{16}ClN_3O_3$ requires 309; found 310 (MH$^+$).

Description for D97

Ethyl 3-[3-chloro-5-(5-{3-chloro-4-[(trifluoromethyl)oxy]phenyl}-1,2,4-oxadiazol-3-yl)-1H-indol-1-yl]propanoate (D97)

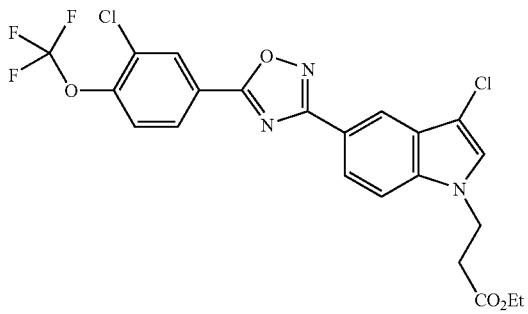

3-Chloro-4-[(trifluoromethyl)oxy]benzoic acid (commercial: ABCR) (168 mg, 0.70 mmol) stirring in DMF (6 ml) was treated with EDC (146 mg, 0.76 mmol) followed by HOBt (104 mg, 0.76 mmol). The resultant solution was stirred for 15 minutes. Added ethyl 3-{3-chloro-5-[(hydroxyamino)(imino)methyl]-1H-indol-1-yl}propanoate (D96) (216 mg, 0.70 mmol) and stirred at RT for 45 minutes. The solution was heated at 80° C. for 6 hours then left standing at room temperature overnight. Single product formed by LC/MS. Added EtOAc (50 ml) and washed with water (50 ml), saturated aqueous sodium hydrogen carbonate (50 ml) and water (50 ml). Dried over MgSO$_4$ and evaporated off the solvent. The residue was crystallised from ethanol to yield 200 mg of white solid. δH (400 MHz, d$_6$-DMSO) 1.11 (3H, t), 2.92 (2H, t), 4.00 (2H, q), 4.49 (2H, t), 7.75 (1H, s), 7.80 (1H, d), 7.85 (1H, dd), 7.95 (1H, dd) 8.23 (1H, d) 8.30 (1H, dd), 8.47 (1H, d). MS (ES) $C_{22}H_{16}{}^{35}Cl^{37}ClF_3N_3O_4$ requires 515; found 516 (MH$^+$).

Description for D98 Alternative to Description for D28

Ethyl 4-chloro-3-(trifluoromethyl)benzoate (D98)

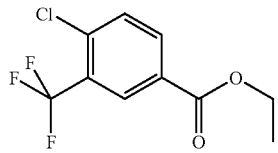

A solution of 4-chloro-3-trifluoromethyl benzoic acid (10 g, 44.5 mmol) in ethanol (10 ml) was split equally between two microwave vials. Concentrated sulfuric acid (0.75 ml) was added to each vial (1.5 ml in total). The reactions were heated in the microwave at 120° C. for 30 minutes in total. The reaction mixtures were combined and concentrated in vacuo. The residue was partitioned between EtOAc (100 ml) and aq. sodium bicarbonate (100 ml), the organic phase was separated, washed with aq. sodium bicarbonate (100 ml) and water (2×100 ml) and then dried (phase separator) and the solvent removed in vacuo to give the title compound (4.126 g) as a colourless oil. δH (400 MHz, methanol-d$_4$) 1.40 (3H, t), 4.41 (2H, quart), 7.76 (1H, d), 8.22 (1H, dd), 8.34 (1H, d).

Description for D99

Methyl 3-chloro-4-(propyloxy)benzoate (D99)

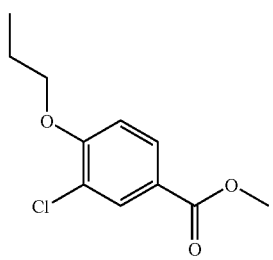

Methyl 4-hydroxy-3-chlorobenzoate (10 g, 53.6 mmol) was dissolved in DMF (110 ml) and then potassium carbonate (14.8 g, 107.2 mmol) was added followed by n-propyliodide (10.4 ml, 107.2 mmol). The reaction was heated to 70° C.

overnight, filtered and then the filtrate was partitioned between EtOAc and water. The organic layer was separated, dried and evaporated to give the title compound as a yellow oil (12.37 g). δH (400 MHz, d$_6$-DMSO) 1.00 (3H, t), 1.72-1.92 (2H, m), 3.82 (3H, s), 4.10 (2H, t), 7.24 (1H, d), 7.85-8.10 (2H, m). MS (ES) C$_{11}$H$_{13}$$^{35}$ClO$_3$ requires 228; found 229 (MH$^+$).

Description for D100

3-Chloro-4-(propyloxy)benzoic acid (D100)

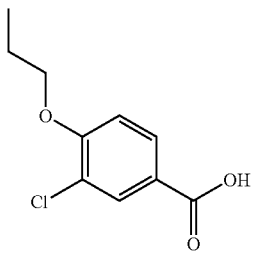

A solution of methyl 3-chloro-4-(propyloxy)benzoate (D99) (12.22 g, 0.053 mol) in ethanol (40 ml) and 2M NaOH aq. (40 ml) was heated at 60° C. for 3 hours. The reaction was allowed to cool and then left at room temperature over the weekend. The reaction mixture was poured into a mixture of dilute aq. HCl and EtOAc. The organic layer was separated, dried and evaporated to give a solid which was triturated with ether to give the title compound as a white solid (7.7 g). δH (400 MHz, d$_6$-DMSO) 1.00 (3H, t), 1.67-1.87 (2H, m) 4.10 (2H, t), 7.24 (1H, d), 7.84-8.06 (2H, m), 12.97 (1H, br s). MS (ES) C$_{10}$H$_{11}$$^{35}$ClO$_3$ requires 214; found 213 (M−H$^+$).

Description for D101

Ethyl 3-(3-chloro-5-{5-[3-chloro-4-(propyloxy)phenyl]-1,2,4-oxadiazol-3-yl}-1H-indol-1-yl)propanoate (D101)

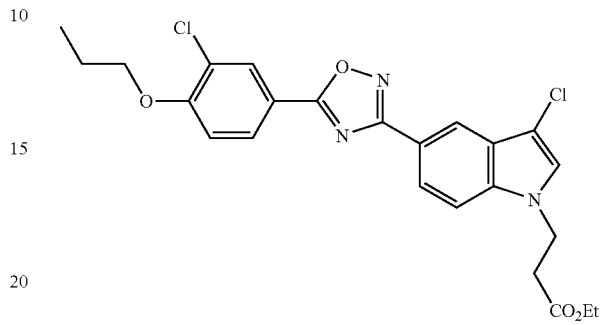

3-Chloro-4-(propyloxy)benzoic acid (D100) (150 mg, 0.70 mmol) stirring in DMF was treated with EDC (146 mg, 0.76 mmol) followed by HOBt (104 mg, 0.76 mmol). The resultant solution was stirred and ethyl 3-{3-chloro-5-[(hydroxyamino)(imino)methyl]-1H-indol-1-yl}propanoate (D96) (216 mg, 0.70 mmol) added. Heated mixture at 80° C. until reaction was complete. Work up obtained the title compound as 160 mg of pale cream solid. δH (400 MHz, d$_6$-DMSO) 1.03 (3H, t), 1.10 (3H, t), 1.77-1.86 (2H, m), 2.90 (2H, t), 4.05 (2H, q), 4.18 (2H, t), 4.49 (2H, t), 7.40 (1H, d), 7.74 (1H, s), 7.81 (1H, d), 7.91 (1H, dd), 8.15 (1H, dd), 8.22-8.23 (2H, m). MS (ES) C$_{24}$H$_{23}$$^{35}$Cl$_2$N$_3$O$_4$ requires 487; found 488 (MH$^+$).

The following compounds were prepared by similar methods to those described above. The reactions were worked up by partitioning the crude material between ethyl acetate and aq. sodium bicarbonate, separating the organic layer, drying it and evaporating to dryness. The compounds were purified by trituration or normal phase chromatography.

| | Structure | precursor | Name | MH$^+$ |
|---|---|---|---|---|
| D102 | 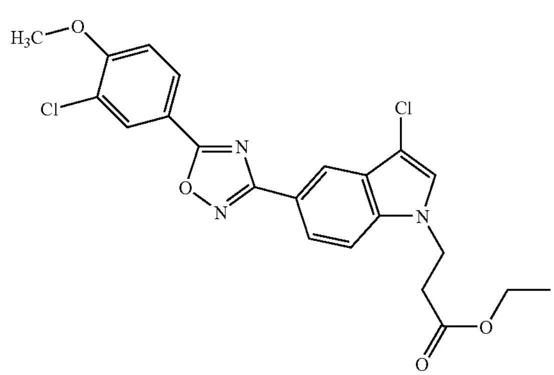 | D96 | ethyl 3-(3-chloro-5-{5-[3-chloro-4-(methyloxy)phenyl]-1,2,4-oxadiazol-3-yl}-1H-indol-1-yl)propanoate | 460 |

| | Structure | precursor | Name | MH+ |
|---|---|---|---|---|
| D103 | 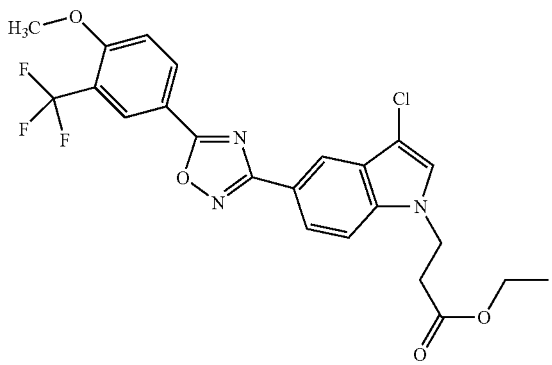 | D96 | ethyl 3-(3-chloro-5-{5-[4-(methyloxy)-3-(trifluoromethyl)phenyl]-1,2,4-oxadiazol-3-yl}-1H-indol-1-yl)propanoate | 494 |
| D104 | 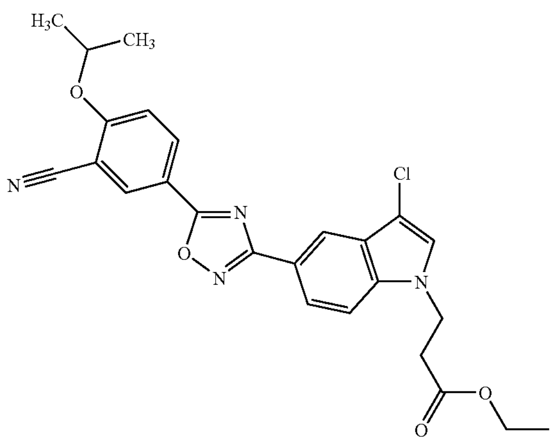 | D96 | ethyl 3-[3-chloro-5-(5-{3-cyano-4-[(1-methylethyl)oxy]phenyl}-1,2,4-oxadiazol-3-yl)-1H-indol-1-yl]propanoate | 479 |
| D105 | 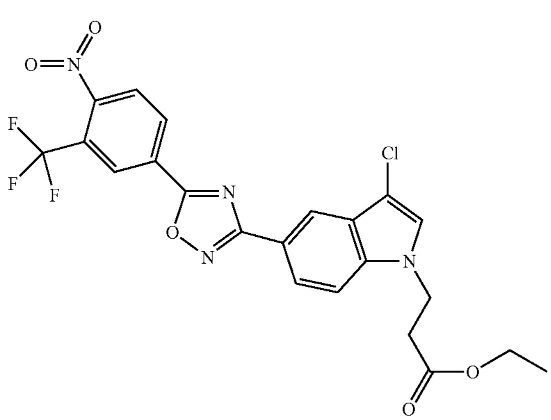 | D96 | ethyl 3-(3-chloro-5-{5-[4-nitro-3-(trifluoromethyl)phenyl]-1,2,4-oxadiazol-3-yl}-1H-indol-1-yl)propanoate | — |

Description for D106

Ethyl 3-(5-{5-[3-bromo-4-(methyloxy)phenyl]-1,2,4-oxadiazol-3-yl}-3-chloro-1H-indol-1-yl)propanoate (D106)

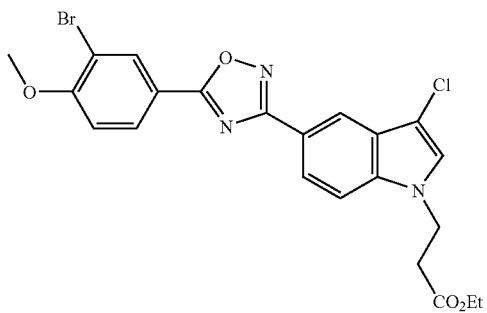

The 3-bromo-4-(methyloxy)benzoic acid (commercial: ICN) (243 mg, 1.05 mmol) stirring in DMF (10 ml) was treated with EDC (219 mg, 0.1.14 mmol) followed by HOBt (156 mg, 0.1.14 mmol). The resultant solution was stirred for 10 minutes. Added ethyl 3-{3-chloro-5-[(hydroxyamino)(imino)methyl]-1H-indol-1-yl}propanoate (D96) (324 mg, 1.05 mmol) and stirred at RT for 45 minutes. The solution was heated at 80° C. for 4 hours then left standing overnight. The solution was heated at 80° C. for a further 4 hours to give one major product. Evaporated off the DMF, added EtOAc (50 ml) and washed with water (50 ml). The EtOAc was washed with sat. aqueous sodium hydrogen carbonate (50 ml) and water (50 ml) then dried over $MgSO_4$. Evaporated off the solvent and crystallised from ethanol to yield the title compound as 280 mg of cream solid. δH (400 MHz, $d_6$-DMSO) 1.10 (3H, t), 2.90 (2H, t), 3.99-4.05 (5H, m), 4.49 (2H, t), 7.38 (1H, d), 7.74 (1H, s), 7.80 (1H, d), 7.97 (1H, d), 8.21-8.23 (2H, m), 8.36 (1H, d). MS (ES) $C_{22}H_{19}{}^{81}Br{}^{35}ClN_3O_4$ requires 505; found 506 (MH$^+$).

Description for D107

Ethyl 3-(3-chloro-5-{5-[6-(methyloxy)-3-biphenylyl]-1,2,4-oxadiazol-3-yl}-1H-indol-1-yl)propanoate (D107)

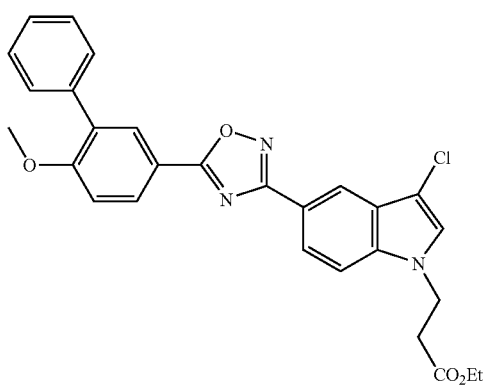

Ethyl 3-(5-{5-[3-bromo-4-(methyloxy)phenyl]-1,2,4-oxadiazol-3-yl}-3-chloro-1H-indol-1-yl)propanoate (D106) (212 mg, 0.42 mmol), phenyl boronic acid (104 mg, 0.84 mmol), Pd(PPh$_3$)$_4$ (20 mg) and 2N aq. sodium carbonate solution (3 ml, 6 mmol) were suspended in DME (6 ml) and heated at 90° C. for 2 hours. Added phenyl boronic acid (30 mg, 0.24 mmol) and Pd(PPh$_3$)$_4$ (20 mg) and heated at 90° C. for a further 2 hours. Added EtOAc (70 ml) and washed with water (100 ml). Dried over MgSO$_4$ and evaporated off the solvent. The residue was crystallised from ethanol to yield the title compound as 90 mg of light tan solid. MS (ES) $C_{28}H_{24}{}^{35}ClN_3O_4$ requires 501; found 502 (MH$^+$).

Description for D108

Ethyl 3-{3-chloro-5-[5-(3-chloro-4-hydroxyphenyl)-1,2,4-oxadiazol-3-yl]-1H-indol-1-yl}propanoate (D108)

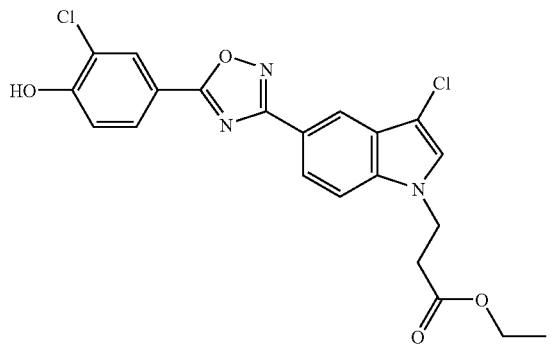

3-Chloro-4-hydroxybenzoic acid (commercial) (240 mg, 1.40 mmol) in dry DMF (8 ml) was treated with EDC (292 mg, 1.52 mmol) and HOBt (208 mg, 1.52 mmol) and stirred for 5 minutes. Added ethyl 3-{3-chloro-5-[(hydroxyamino)(imino)methyl]-1H-indol-1-yl}propanoate (D96) (432 mg, 1.40 mmol) and stirred at RT for 30 minutes. The reaction mixture was heated at 80° C. for 7 hours. Added EtOAc (70 ml) and washed with water (70 ml), sat. aq, sodium hydrogen carbonate (70 ml) and water (70 ml). Dried over MgSO$_4$ and evaporated off the solvent. The residue was subjected to chromatography using a biotage (EtOAc/hexane 1:2) to obtain the title compound as 200 mg of white solid. δH (400 MHz, $d_6$-DMSO) 1.10 (3H, t), 2.91 (2H, t), 4.04 (2H, q), 4.50 (2H, t), 7.67-7.70 (2H, m), 7.75 (1H, s), 7.80-7.81 (2H, m), 7.94 (1H, dd), 8.22-8.25 (1H, m), 10.95 (1H, broad s). MS (ES) $C_{21}H_{17}{}^{35}Cl_2N_3O_4$ requires 445; found 446 (MH$^+$).

Description for D109

Ethyl 3-(3-chloro-5-{5-[3-chloro-4-(ethyloxy)phenyl]-1,2,4-oxadiazol-3-yl}-1H-indol-1-yl)propanoate (D109)

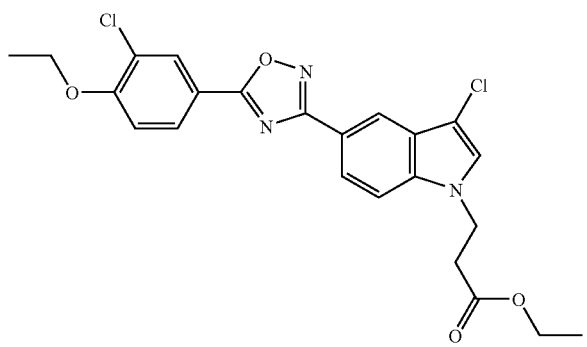

To ethyl 3-{3-chloro-5-[5-(3-chloro-4-hydroxyphenyl)-1,2,4-oxadiazol-3-yl]-1H-indol-1-yl}propanoate (D108) (180 mg, 0.40 mmol) and $K_2CO_3$ (138 mg, 1.0 mmol) in dry DMF (3 ml) was added ethyl iodide (78 mg, 0.50 mmol) and the mixture heated at 80° C. with stirring for 30 minutes. Cooled mixture and added EtOAc (50 ml). Washed with water (3×40 ml) and dried over $MgSO_4$. Evaporated off the solvent and crystallised from ethanol to yield the title compound as 110 mg of white solid. $\delta H$ (400 MHz, $d_6$-DMSO) 1.10 (3H, t), 1.42 (3H, t), 2.90 (2H, t), 4.02 (2H, q), 4.27 (2H, q), 4.49 (2H, t), 7.40 (1H, d), 7.74 (1H, s), 7.80 (1H, d), 7.95 (1H, dd), 8.16 (1H, dd), 8.21-8.22 (2H, m). MS (ES) $C_{23}H_{21}{}^{35}Cl_2N_3O_4$ requires 473; found 474 ($MH^+$).

Description for D110

Ethyl 3-[3-chloro-5-(5-{3-chloro-4-[(1-methylethyl)oxy]phenyl}-1,2,4-oxadiazol-3-yl)-1H-indol-1-yl]propanoate (D110)

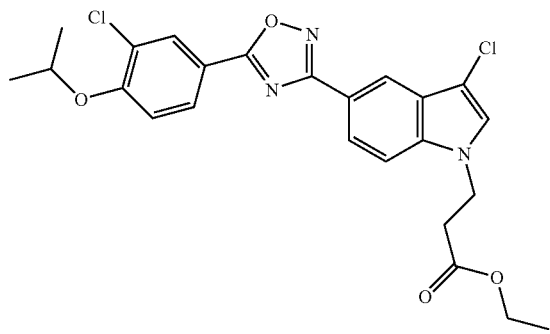

To ethyl 3-{3-chloro-5-[5-(3-chloro-4-hydroxyphenyl)-1,2,4-oxadiazol-3-yl]-1H-indol-1-yl}propanoate (D108) (180 mg, 0.40 mmol) and $K_2CO_3$ (138 mg, 1.0 mmol) in dry DMF (5 ml) was added isopropyl iodide (85 mg, 0.50 mmol) and the mixture stirred at 80° C. for 30 minutes. Cooled mixture and added EtOAc (50 ml). Washed with water (2×50 ml) and dried over $MgSO_4$. Evaporated off the solvent and crystallised from ethanol to yield the title compound as 120 mg of white solid. $\delta H$ (400 MHz, $d_6$-DMSO) 1.12 (3H, t), 1.37 (6H, d), 2.91 (2H, t), 4.02 (2H, q), 4.50 (2H, t), 4.89-4.98 (1H, m), 7.72-7.85 (5H, m), 7.95-8.00 (1H, m), 8.24 (1H, d). MS (ES) $C_{24}H_{23}{}^{35}Cl_2N_3O_4$ requires 487; found 488 ($MH^+$).

Description for D111

3-Iodo-4-(trifluoromethyl)benzoic acid (D111)

3-Amino-4-(trifluoromethyl)benzoic acid (commercially available) (6.5 g, 31.7 mmol) and triiodomethane (37.4 g, 95.1 mmol) were dissolved in THF (300 ml). The reaction mixture was heated to 80° C. and then butyl nitrite (5.56 ml, 47.6 mmol) was added slowly at this temperature. Heating was continued at this temperature for 4 hours and then the reaction was concentrated in vacuo to give the crude product. Purification by column chromatography (hexane to 30% EtOAc in hexane). This material was combined with another batch from a similar reaction performed on 2 g of 3-amino-4-(trifluoromethyl)benzoic acid. The combined material was purified by preparative HPLC to give the title compound (6.1 g). MS $C_8H_4F_3IO_2$ requires 316; found 315 ($M-H^+$).

Description for D112

Ethyl 3-(5-{5-[3-iodo-4-(trifluoromethyl)phenyl]-1,2,4-oxadiazol-3-yl}-1H-indol-1-yl)propanoate (D112)

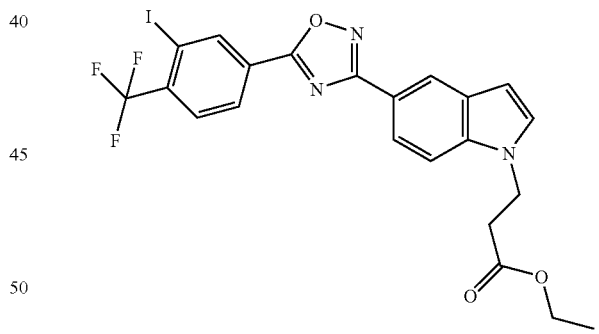

D111 (1.0 g, 3.16 mmol) was dissolved in DMF (25 ml) under nitrogen. EDC (0.7 g, 3.7 mmol) and HOBt (0.5 g) were added. The reaction was stirred at room temperature for 15 minutes and then triethylamine (0.87 ml, 6.32 mmol) was added and the reaction was stirred for a further 5 minutes. D52 (0.87 g, 3.16 mmol) was added and the reaction was stirred at room temperature overnight. The reaction was concentrated in vacuo and the resultant oil diluted with ethyl acetate (100 ml). The organic layer was washed with water (2×30 ml), dried ($Na_2SO_4$) and concentrated in vacuo to give the crude product which was purified by column chromatography. The product was eluted in 7% EtOAc in hexane and evaporation afforded the title compound (0.45 g). MS $C_{22}H_{17}F_3N_3O_3$ requires 555; found 556 ($MH^+$).

Description for D113

Ethyl 3-(5-{5-[6-(trifluoromethyl)-3-biphenylyl]-1,2,4-oxadiazol-3-yl}-1H-indol-1-yl)propanoate (D113)

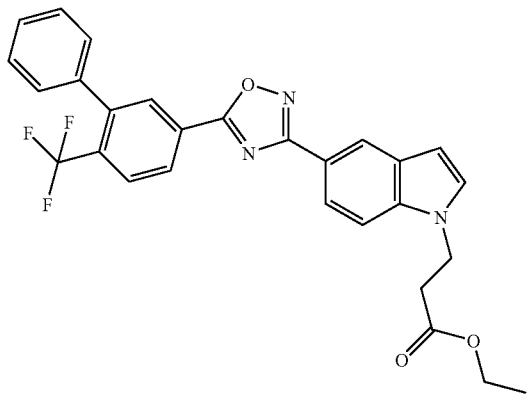

This material was prepared by a similar method to that used for D107 from D112. MS (ES) $C_{28}H_{22}F_3N_3O_2$ requires 505; found 506 (MH$^+$).

EXAMPLES

Example 1

3-(5-{5-[4-phenyl-5-(trifluoromethyl)-2-thienyl]-1,2,4-oxadiazol-3-yl}-1H-indol-1-yl)propanoic acid (E1)

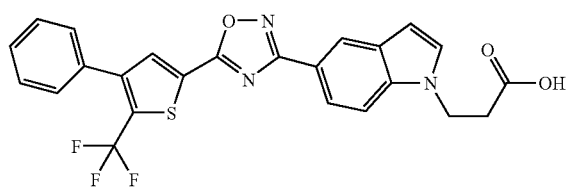

D3 (38 mg) was dissolved in 2M aqueous NaOH (0.5 ml) and MeOH (0.5 ml) then stirred at RT overnight. LCMS analysis showed 41% product so the reaction mixture was heated to 50° C. and stirred over the weekend. LCMS showed the reaction to be complete. The reaction mixture was evaporated then partitioned between H$_2$O and DCM. The organic layer was extracted with H$_2$O. The combined aqueous extracts were acidified to pH=1 and extracted with DCM. These DCM extracts were dried over MgSO$_4$, filtered and evaporated to give the crude product MF105672-149A1 (30 mg). The crude product was purified on a silica cartridge (12+S), eluting with a 0 to 10% mixture of MeOH in DCM to give the purified product. This was dissolved in CHCl$_3$ and evaporated to give the title compound (3 mg) as a white solid. δH (CDCl$_3$, 400 MHz): 2.92 (2H, t), 4.50 (2H, t), 6.51 (1H, d), 7.24 (1H, d), 7.40-7.53 (6H, m), 7.90 (1H, s), 8.00 (1H, d), 8.45 (1H, s). MS (ES$^+$): $C_{24}H_{16}F_3N_3O_3S$ requires 483; found 484 (MH$^+$).

Example 1 Alternative Procedure 3-(5-{5-[4-phenyl-5-(trifluoromethyl)-2-thienyl]-1,2,4-oxadiazol-3-yl}-1H-indol-1-yl)propanoic acid (E1)

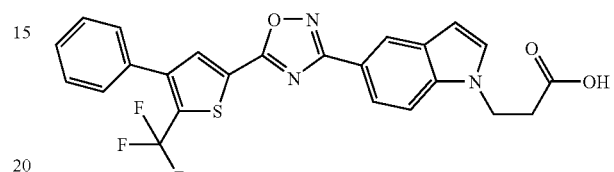

D3 (600 mg) was treated with 2 M aq. NaOH (25 ml) and MeOH (25 ml). This mixture was stirred overnight then heated to 50° C. for 6 hours. The MeOH was then evaporated and the remaining solution acidified and extracted with EtOAc (×3). The combined organic solutions were washed with brine and evaporated to give the crude residue C(302 mg) as an off-white solid. This was triturated with cold MeOH to give the title compound (162 mg) as a grey solid. δH (d$_6$-DMSO, 400 MHz): 2.80 (2H, t), 4.46 (2H, t), 6.64 (1H, d), 7.49-7.59 (6H, m), 7.72 (1H, d), 7.85 (1H, dd), 8.22-8.25 (1H, m), 8.31-8.34 (1H, m). MS (ES): $C_{24}H_{16}F_3N_3O_3S$ requires 483; found 484 (MH$^+$).

Example 2

Sodium 3-(5-{5-[4-phenyl-5-(trifluoromethyl)-2-thienyl]-1,2,4-oxadiazol-3-yl}-1H-indol-1-yl)propionate (E2)

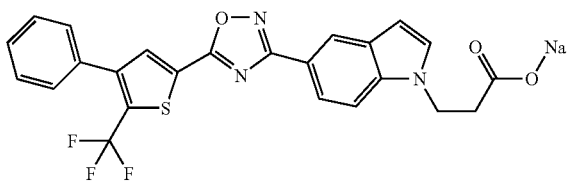

E1 (30 mg) was dissolved in EtOAc (1 ml), treated with 2M aqueous NaOH (40 ul), diluted with H$_2$O (1 ml) and extracted with EtOAc (3×5 ml), using a small volume of brine during the third extraction to aid phase separation. The combined organics were evaporated to give the title compound (37 mg) as a green solid. δH (methanol-d$_4$, 400 MHz): 2.68 (2H, t), 4.48 (2H, t), 6.55 (1H, d), 7.49 (1H, d), 7.45-7.56 (5H, m), 7.62 (1H, d), 7.92 (1H, d), 8.03 (1H, s), 8.35 (1H, s). MS (ES$^+$): $C_{24}H_{16}F_3N_3O_3S$ requires 483; found 484 (MH$^+$).

Example 3

3-[5-(5-{3-Chloro-4-[(1-methylethyl)oxy]phenyl}-1,2,4-oxadiazol-3-yl)-1H-indol-1-yl]propanoic acid (E3)

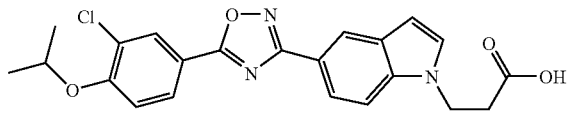

D6 MF105672-178A2 (38 mg) was dissolved in EtOH, treated with 12.5 M aqueous NaOH (2 ml) and stirred at RT for 4 hours. The reaction mixture was evaporated, re-dissolved in $H_2O$ and washed with diethyl ether. The aqueous solution was acidified then extracted with DCM. The DCM solutions were combined, dried over $MgSO_4$, filtered and evaporated to give the title compound MF105672-181A1 (5 mg) as a pale yellow solid. δH ($CDCl_3$, 400 MHz): 1.44 (6H, d), 2.94 (2H, t), 4.51 (2H, t), 4.73 (1H, septet), 6.61 (1H, d), 7.07 (1H, d), 7.22 (1H, d), 7.45 (1H, d), 7.94 (1H, d), 8.07 (1H, d), 8.27 (1H, s), 8.47 (1H, s). MS (ES): $C_{22}H_{20}ClN_3O_4$ requires 425; found 426 ($MH^+$).

Example 4

Sodium 3-[3-Chloro-5-(5-{3-chloro-4-[(1-methylethyl)oxy]phenyl}-1,2,4-oxadiazol-3-yl)-1H-indol-1-yl]propanoate (E4)

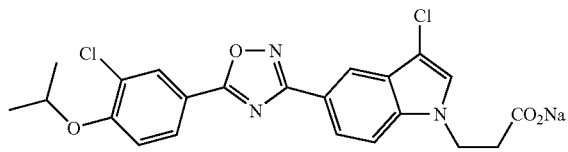

D7 (200 mg) and $Cs_2O_3$ (336 mg) were placed in a microwave vial, treated with DMF (2.8 ml) and ethyl 3-bromopropionate (99 ul) and sonicated for 10 minutes. The mixture was then heated to 120° C. in a microwave reactor for 25 mins. The reaction mixture was then evaporated, re-dissolved in MeOH (10 ml) and treated with 2 M aq. NaOH (10 ml). This mixture was sonicated briefly and then heated to 50° C. overnight. The reaction mixture was then evaporated, diluted with $H_2O$ (70 ml) and extracted with EtOAc, adding NaCl and acetone to improve the extraction. The organic extracts were evaporated to give the crude product which was acidified with HCl to give the free-acid. This was insufficiently soluble for purification by chromatography and so was triturated with MeOH, treated with 2M aq. NaOH (1.5 eq.), evaporated, dissolved in EtOAc, filtered and evaporated to give the title compound (56 mg) as a brown solid. δH (methanol-$d_4$, 400 MHz): 1.42 (6H, d), 2.66 (2H, t), 4.47 (2H, t), 4.82 (1H, m), 7.29 (1H, d), 7.44 (1H, s), 7.65 (1H, d), 7.98 (1H, d), 8.12 (1H, d), 8.20 (1H, s), 8.30 (1H, s). MS (ES): $C_{22}H_{19}{}^{35}Cl_2N_3O_4$ requires 459; found 460 ($MH^+$).

Example 5

3-(3-Chloro-5-{5-[4-phenyl-5-(trifluoromethyl)-2-thienyl]-1,2,4-oxadiazol-3-yl}-1H-indol-1-yl)propanoic acid (E5)

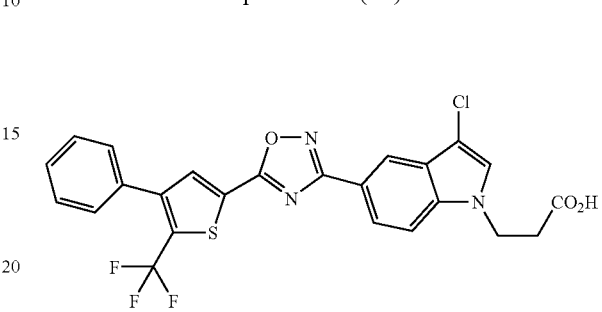

D8 (86 mg), 3-bromopropionate (52 mg), $Cs_2CO_3$ (126 mg) and DMF (1 ml) were placed in a microwave vial and stirred at 131° C. in the microwave reactor for 1.5 hours. The reaction mixture was then evaporated to dryness and treated with 2M aq. NaOH and EtOH (20 ml). This solution was stirred at 50° C. for 4 hours and then neutralised with HCl and evaporated to remove the EtOH. The aqueous solution was then extracted twice with EtOAc and the combined extracts evaporated. The residue was dissolved in DMSO, filtered, treated with MeCN causing precipitation of the product which was filtered and washed with MeCN to give the title compound (23 mg) as an off-white solid. δH ($d_6$-DMSO, 400 MHz): 2.47-2.57 (solvent+2H) 4.37 (2H, t), 7.51-7.59 (5H, m), 7.72 (1H, s), 7.76 (1H, d), 7.89 (1H, d), 8.17 (1H, s), 8.25 (1H, s). MS (ES): $C_{24}H_{16}ClF_3N_3O_2S$ requires 517; found 516 ($M-H^+$).

Example 6

3-(4-{5-[4-Phenyl-5-(trifluoromethyl)-2-thienyl]-1,2,4-oxadiazol-3-yl}-1H-indol-1-yl)propanoic acid (E6)

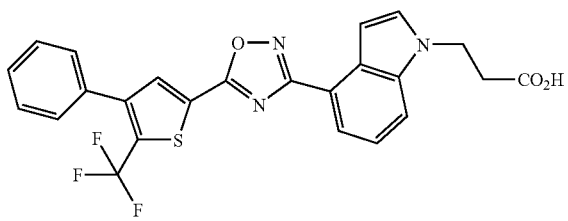

D10 (85 mg, 0.207 mmol) was placed in a microwave vial with $Cs_2CO_3$ (135 mg) and DMF (1 ml). This was stirred briefly and ethyl bromopropionate (40 ul) was added. The mixture was heated at 130° C. for 1.5 hours in the microwave reactor. The reaction mixture was transferred to a flask containing 2 M aqueous NaOH (5 ml) and EtOH (5 ml), then stirred at room temperature overnight. The mixture was then evaporated and the residue acidified to pH=2.5 with 2 M aqueous HCl. This solution was extracted with EtOAc twice and the combined extracts evaporated to give a yellow residue which was purified by MDAP to give the title compound (50 mg) as a white solid. δH (CDCl₃, 400 MHz): 2.93 (2H, t), 4.50 (2H, t), 7.26 (1H, s), 7.33 (1H, d), 7.37 (1H, ap t), 7.45-7.52 (5H, m), 7.55 (1H, d), 7.93 (1H, s), 8.04 (1H, d). MS (ES): $C_{24}H_{16}F_3N_3O_3S$ requires 483; found 482 (M–H⁺).

Example 7

3-[4-(5-{3-Chloro-4-[(trifluoromethyl)oxy]phenyl}-1,2,4-oxadiazol-3-yl)-1H-indol-1-yl]propanoic acid (E7)

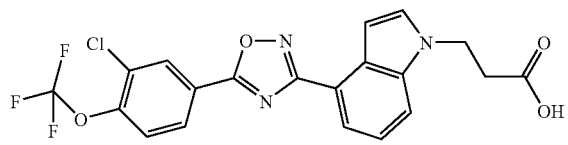

3-Chloro-4-[(trifluoromethyl)oxy]benzoic acid (commercial source) (131 mg), EDCI (114 mg) and HOBT (81 mg) were dissolved in DMF (2.5 ml) and stirred at RT for 10 minutes. Ethyl 3-{5-[(hydroxyamino)(imino)methyl]-1H-indol-1-yl}propanoate (D57) (150 mg) in DMF (2.5 ml) was added and stirring continued at RT for 2 hours. The mixture was then heated at 80° C. overnight. The reaction mixture was evaporated to dryness then extracted with EtOAc (2×25 ml) from H₂O (25 ml). The combined organic solutions were evaporated to dryness and the residue treated with EtOH and 2 M aq. NaOH (1:1 mixture, 20 ml). This mixture was stirred at 50° C. for 2 hours then evaporated to remove the EtOH. The resultant precipitate was filtered off and washed with a mixture of H₂O and EtOH then 2 M HCl. The residue was recrystallised from hot EtOH to give the title compound (62 mg) as a white solid. δH (d₆-DMSO, 400 MHz): 2.81 (2H, t), 4.50 (2H, t), 7.08 (1H, d), 7.36 (1H, apparent t), 7.61 (1H, d), 7.83 (1H, d), 7.89 (1H, d), 7.96 (1H, d), 8.32 (1H, dd), 8.50 (1H, d). MS (ES⁻): $C_{20}H_{13}{}^{35}ClF_3N_3O_4$ requires 451; found 450 (M–H⁺).

Example 8

3-[4-(5-{3-Chloro-4-[(1-methylethyl)oxy]phenyl}-1,2,4-oxadiazol-3-yl)-1H-indol-1-yl]propanoic acid (E8)

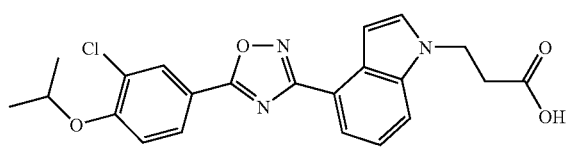

3-chloro-4-[(1-methylethyl)oxy]benzoic acid (D4) (117 mg) was added to EDCI (114 mg) and HOBT (81 mg) dissolved in DMF (2.5 ml). This was stirred at RT for 10 minutes and then ethyl 3-{4-[(hydroxyamino)(imino)methyl]-1H-indol-1-yl}propanoate (D57) (150 mg) in DMF (2.5 ml) was added and stirring continued at RT for 2 hours then at 80° C. overnight. The reaction mixture was evaporated to dryness and extracted from H₂O (25 ml) with EtOAc (2×25 ml). The combined organics were evaporated and treated with 2 M aq. NaOH (10 ml) and EtOH (10 ml), stirred at 50° C. for 2 hours then evaporated to remove the EtOH. The remaining solution was acidified, filtered and the precipitate washed with EtO/H₂O then recrystallised from hot EtOH/H₂O then from DMSO. Washing with Et₂O and MeOH gave the title compound (46 mg) as a white solid. δH (d₆-DMSO, 400 MHz): 1.37 (6H, d), 2.81 (2H, t), 4.50 (2H, t), 4.89 (1H, septet), 7.08 (1H, d), 7.35 (1H, apparent t), 7.46 (1H, d), 7.60 (1H, d), 7.81 (1H, d), 7.94 (1H, d), 8.15 (1H, dd), 8.23 (1H, d). MS (ES⁻): $C_{22}H_{20}{}^{35}ClN_3O_4$ requires 425; found 424 (M–H⁺).

Example 9

3-[4-(5-{5-Chloro-6-[(1-methylethyl)oxy]-3-pyridinyl}-1,2,4-oxadiazol-3-yl)-1H-indol-1-yl]propanoic acid (E9)

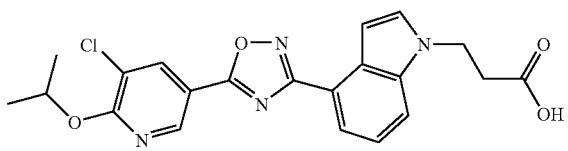

Ethyl 3-{4-[(hydroxyamino)(imino)methyl]-1H-indol-1-yl}propanoate (D57) (150 mg) in DMF (2.5 ml) was added to a solution of 5-chloro-6-[(1-methylethyl)oxy]-3-pyridinecarboxylic acid (D61) (118 mg), HOBT (81 mg) and EDCI (114 mg) which had been stirring at RT for 10 minutes in DMF (2.5 ml). The resultant mixture was stirred at RT for 2 hours then heated at 80° C. for three days. The reaction mixture was evaporated to dryness and extracted from H₂O (25 ml) with EtOAc (2×25 ml). The combined organics were evaporated and the residue stirred in EtOH/2 M aq. NaOH (1:1 mixture, 20 ml) at 50° C. for 2 hours. The EtOH was evaporated and the precipitate removed by filtration. This was acidified then purified by MDAP to give the title compound (48 mg) as an off white solid. δH (d₆-DMSO, 400 MHz): 1.40 (6H, d), 2.80 (2H, t), 4.50 (2H, t), 5.46 (1H, septet), 7.08 (1H, d), 7.36 (1H, apparent t), 7.60 (1H, d), 7.82 (1H, d), 7.95 (1H, d), 8.60 (1H, d), 8.97 (1H, d). MS (ES⁻): $C_{21}H_{19}{}^{35}ClN_4O_4$ requires 426; found 425 (M–H⁺).

Example 9

Alternative Procedure

3-[4-(5-{5-Chloro-6-[(1-methylethyl)oxy]-3-pyridinyl}-1,2,4-oxadiazol-3-yl)-1H-indol-1-yl]propanoic acid (E9)

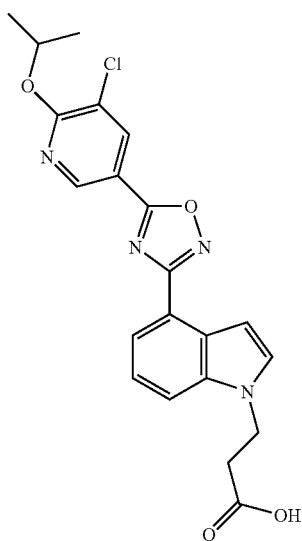

Ethyl 3-[4-(5-{5-chloro-6-[(1-methylethyl)oxy]-3-pyridinyl}-1,2,4-oxadiazol-3-yl)-1H-indol-1-yl]propanoate (D62) (1.1 g, 2.418 mmol) was dissolved in a mixture of 1,4-dioxane (100 ml) and ethanol (100 ml). Water (50.0 ml) was added followed by 2N sodium hydroxide (2.418 ml, 4.84 mmol). The mixture was stirred at RT for one and a half hours to give a single product. Evaporated off most of the solvent, acidified with glacial acetic acid, added water (50 ml) and extracted product into EtOAc (200 ml). Washed with water (30 ml) and dried over MgSO₄. The solvent was evaporated off until a white precipitate was formed. The solid was filtered off and washed with ether. Mass of title compound obtained was 780 mg. δH (400 MHz, d₆-DMSO) 1.38 (6H, d), 2.81 (2H, t), 4.50 (2H, t), 5.41-5.51 (1H, m), 7.07 (1H, dd), 7.36 (1H, t), 7.59 (1H, d), 7.81 (1H, d), 7.94 (1H, dd), 8.58 (1H, d), 8.96 (1H, d), 12.40 (1H, broad s). MS (ES) $C_{21}H_{19}{}^{35}ClN_4O_4$ requires 426; found 427 (MH⁺).

Example 10

Sodium 3-[5-(5-{3-chloro-4-[(1-methylethyl)oxy]phenyl}-1,2,4-oxadiazol-3-yl)-1H-indol-1-yl]propanoate (E10)

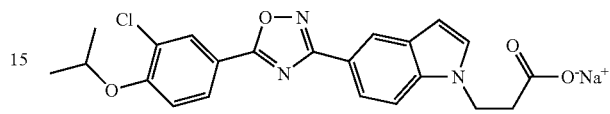

(D5) (200 mg) was dissolved in DMF (4 ml), treated with Cs₂CO₃ (368 mg) and then ethylbromopropionate (109 μl). The resultant mixture was heated to 120° C. in a microwave reactor for 2 hours. The reaction mixture was decanted from the insoluble residue and evaporated to dryness to give a pale orange oil This oil was dissolved in EtOH (2 ml) and treated with 2 M aqueous NaOH (2 ml). This produced a white precipitate so a further portion of EtOH (2 ml) was added to produce a homogeneous solution. The resultant mixture was heated to 60° C. for 1 hour then stood at RT overnight. The reaction mixture was evaporated to dryness, re-dissolved in H₂O (10 ml), treated with brine (2 ml) and extracted with a mixture of EtOAc and MeCN (2×20 ml). Evaporation gave the crude product (313 mg) as a pale green solid. This was dissolved in MeOH (5 ml), filtered and evaporated then triturated with Et₂O to give the title compound (247 mg) as a pale green solid. δH (methanol-d₄, 400 MHz): 1.42 (6H, d), 2.68 (2H, t), 4.48 (2H, t), 4.83 (1H, septet), 6.55 (1H, dd), 7.30 (1H, d), 7.38 (1H, d), 7.61 (1H, d), 7.91 (1H, dd), 8.12 (1H, dd), 8.21 (1H, d), 8.34 (1H, dd). MS (ES⁻): $C_{22}H_{20}ClN_3O_4$ requires 425 found 424 (M–H⁺).

The following compounds were prepared in an similar manner to example 1. The solvent for the hydrolysis step was either methanol or ethanol and the reaction temperature between room temperature and 60° C. In some cases the reactions were worked up by extracting the product or acidified product into an organic solvent and in other cases the final compound precipitated from the aqueous layer and was isolated by filtration. Purification was by MDAP, trituration or recrystallisation.

| Example | Structure | Name | Comments | MS |
|---|---|---|---|---|
| E11 | 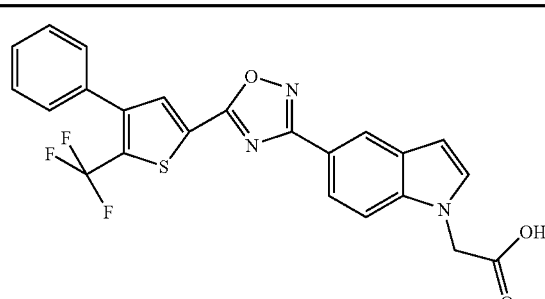 | (5-{5-[4-phenyl-5-(trifluoromethyl)-2-thienyl]-1,2,4-oxadiazol-3-yl}-1H-indol-1-yl)acetic acid | Hydrolysis of D42 | 470 (MH⁺) |

| Example | Structure | Name | Comments | MS |
|---|---|---|---|---|
| E12 | 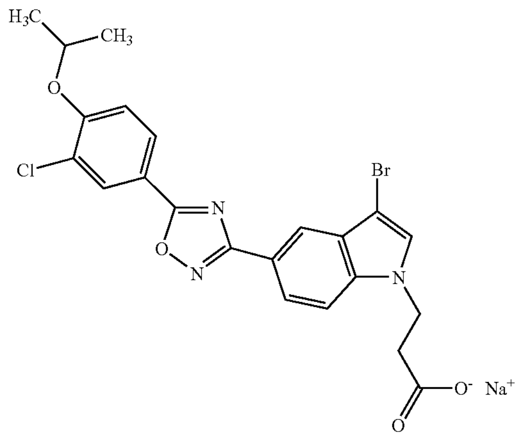 | sodium 3-[3-bromo-5-(5-{3-chloro-4-[(1-methylethyl)oxy]phenyl}-1,2,4-oxadiazol-3-yl)-1H-indol-1-yl]propanoate | Hydrolysis of D43 | 504 (M − H$^+$ for $^{35}$Cl & $^{81}$Br) |
| E13 | 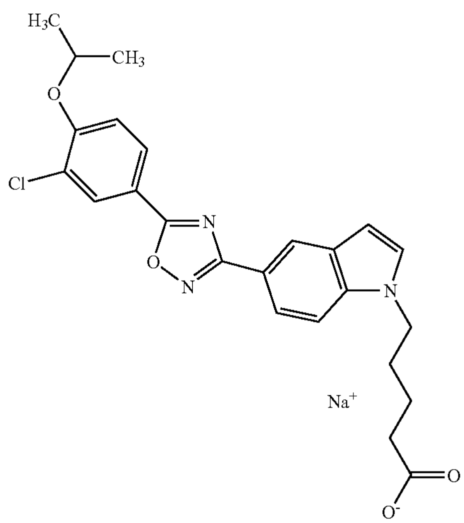 | sodium 5-[5-(5-{3-chloro-4-[(1-methylethyl)oxy]phenyl}-1,2,4-oxadiazol-3-yl)-1H-indol-1-yl]pentan'oate | Hydrolysis of D44 | 454 (MH$^+$ for $^{35}$Cl) |
| E14 | 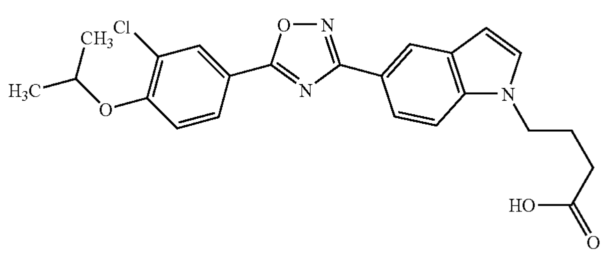 | 4-[5-(5-{3-chloro-4-[(1-methylethyl)oxy]phenyl}-1,2,4-oxadiazol-3-yl)-1H-indol-1-yl]butanoic acid | Hydrolysis of D45 | 440 (MH$^+$ for $^{35}$Cl) |
| E15 | 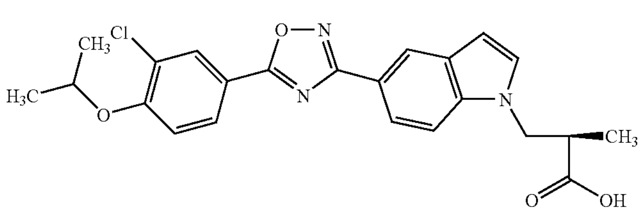 | (2R)-3-[5-(5-{3-chloro-4-[(1-methylethyl)oxy]phenyl}-1,2,4-oxadiazol-3-yl)-1H-indol-1-yl]-2-methylpropanoic acid | Hydrolysis of D46 | 440 (MH$^+$ for $^{35}$Cl |

-continued

| Example | Structure | Name | Comments | MS |
|---|---|---|---|---|
| E16 | 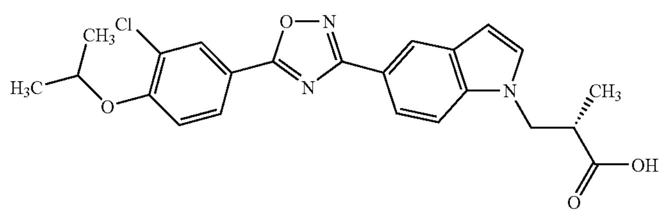 | (2S)-3-[5-(5-{3-chloro-4-[(1-methylethyl)oxy]phenyl}-1,2,4-oxadiazol-3-yl)-1H-indol-1-yl]-2-methylpropanoic acid | Hydrolysis of D47 | 440 (MH+ for 35Cl) |
| E17 | 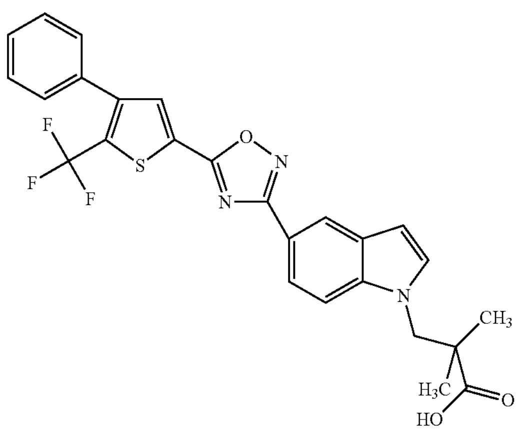 | 2,2-dimethyl-3-(5-{5-[4-phenyl-5-(trifluoromethyl)-2-thienyl]-1,2,4-oxadiazol-3-yl}-1H-indol-1-yl)propanoic acid | Hydrolysis of D48. | 512 (MH+) |

Example 18

3-[5-(5-{3-Chloro-4-[(1-methylethyl)oxy]phenyl}-1,2,4-oxadiazol-3-yl)-1H-indol-1-yl]-2,2,3-trifluoropropanoic acid (E18)

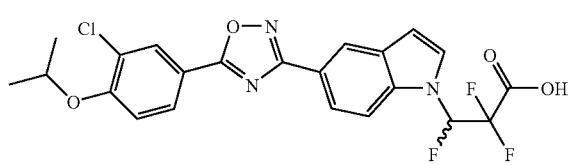

D5 (200 mg), Cs$_2$CO$_3$ (552 mg) and DMF (2.8 ml) were stirred at RT and treated with 3-bromo-2,2,3-trifluoropropanoic acid (175 mg). This mixture was heated at 140° C. for 1 hour in a microwave reactor. 2 further equivalents of Cs$_2$CO$_3$ (368 mg) were added and heating continued at 140° C. for 10 hours. The reaction mixture was then evaporated, treated with H$_2$O, shaken and filtered to give a brown solid residue. This was purified by MDAP to give the title compound (12 mg) as a white solid. δH (methanol-d$_4$, 400 MHz): 1.42 (6H, d), 4.83 (1H, septet), 6.87 (1H, d), 7.29 (1H, d), 7.45 (1H, d), 7.54 (1H, d), 7.61 (1H, d), 7.80 (1H, d), 8.06 (1H, d), 8.11 (1H, d), 8.19-8.22 (1H, m), 8.44 (1H, s).

Example 19

Sodium 4-[4-(5-{3-cyano-4-[(1-methylethyl)oxy]phenyl}-1,2,4-oxadiazol-3-yl)-1H-indol-1-yl]butanoate (E19)

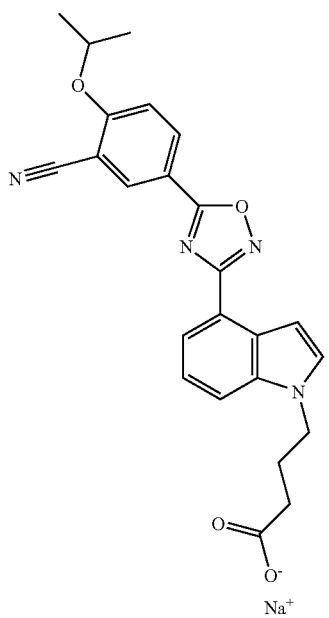

To a solution of ethyl 4-[4-(5-{3-cyano-4-[(1-methylethyl)oxy]phenyl}-1,2,4-oxadiazol-3-yl)-1H-indol-1-yl]butanoate (D65) (1.42 g, 3.09 mmol) in a mixture of dioxan (70 ml) and ethanol (70 ml) was treated with 2N sodium hydroxide (1.86 ml, 3.71 mmol) followed by water (35 ml). The solution was stirred at RT for 4 hours. Evaporated off most of the solvent and filtered off the white solid from the remaining solvent. Washed the solid with water followed by ether and dried to give 580 mg of the title compound. δH (400 MHz, methanol-$d_4$) 1.45 (6H, d), 2.09-2.22 (4H, m), 4.30 (2H, t), 4.92-4.98 (1H, m), 7.15 (1H, d), 7.31 (1H, t), 7.38-7.43 (2H, m), 7.69 (1H, d), 7.95 (1H, d), 8.43-8.46 (2H, m). MS (ES) $C_{24}H_{22}N_4O_4$ requires 430; found 431 (MH$^+$).

Example 20

Sodium 3-[5-(5-{3-cyano-4-[(1-methylethyl)oxy]phenyl}-1,2,4-oxadiazol-3-yl)-1H-indol-1-yl]propanoate

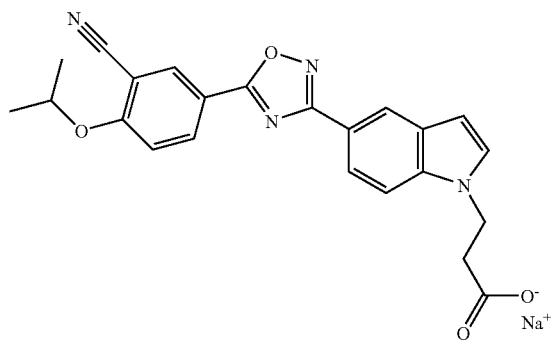

Ethyl 3-[5-(5-{3-cyano-4-[(1-methylethyl)oxy]phenyl}-1,2,4-oxadiazol-3-yl)-1H-indol-1-yl]propanoate (D53) (150 mg, 0.38 mmol) was dissolved in ethanol (25 ml) by warming to 60° C. Allowed solution to cool to RT then added 2N sodium hydroxide (3 ml, 6 mmol). The solution was stirred at RT for 30 minutes. LC/MS showed a single product. Evaporated off the ethanol and filtered off the solid which precipitated out of solution. Mass of title compound as a light tan solid obtained on drying was 50 mg. δH (400 MHz, $d_6$-DMSO) 1.45 (6H, d), 2.67 (2H, t), 4.48 (2H, t), 4.92-4.98 (1H, m), 6.54-6.55 (1H, m), 7.34 (1H, d), 7.38 (1H, d), 7.60 (1H, d), 7.91 (1H, dd), 8.35 (1H, d), 8.41-8.46 (2H, m). MS (ES) $C_{23}H_{20}N_4O_4$ requires 416; found 417 (MH$^+$).

Example 21

Sodium 3-[4-(5-{3-cyano-4-[(1-methylethyl)oxy]phenyl}-1,2,4-oxadiazol-3-yl)-1H-indol-1-yl]propanoate (E21)

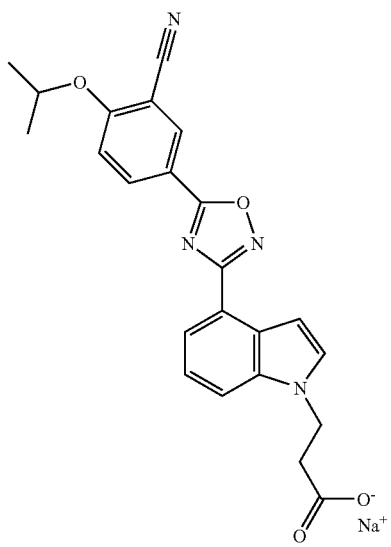

Ethyl 3-[4-(5-{3-cyano-4-[(1-methylethyl)oxy]phenyl}-1,2,4-oxadiazol-3-yl)-1H-indol-1-yl]propanoate (D63) (81 mg, 0.18 mmol) was dissolved in ethanol by warming to 50° C. Added 2N sodium hydroxide (0.25 ml, 0.5 mmol) followed by water (2 ml), warmed to 50° C. to give a clear solution then left standing at RT for 30 minutes. LC/MS showed a single product. The ethanol was evaporated off to obtain a precipitate which was filtered off and dried. Mass of title compound as a pale brown solid obtained was 60 mg δH (400 MHz, $d_6$-DMSO) 1.39 (6H, d), 2.32 (2H, t), 4.39 (2H, t), 4.96-5.00 (1H, m), 7.01 (1H, d), 7.31 (1H, t), 7.56-7.61 (2H, m), 7.74 (1H, d), 7.91 (1H, d), 8.45 (1H, dd), 8.55 (1H, d). MS (ES) $C_{23}H_{20}N_4O_4$ requires 416; found 417 (MH$^+$).

Example 22

Sodium 3-(4-{5-[2-(trifluoromethyl)-4-biphenylyl]-1,2,4-oxadiazol-3-yl}-1H-indol-1-yl)propanoate (E22)

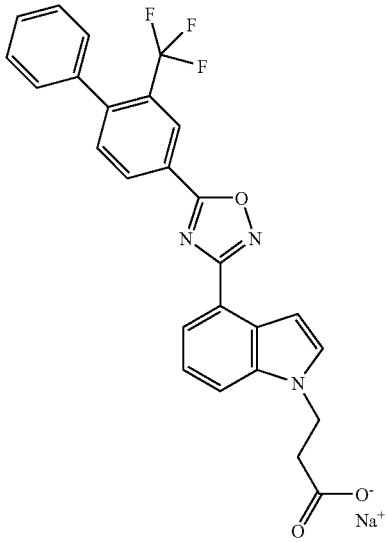

Ethyl 3-(4-{5-[2-(trifluoromethyl)-4-biphenylyl]-1,2,4-oxadiazol-3-yl}-1H-indol-1-yl)propanoate (D64) (15 mg, 0.31 mmol) was dissolved in ethanol (50 ml) by warming to 40° C. for 10 minutes then 2N sodium hydroxide (4 ml, 8 mmol) was added followed by water (8 ml). The solution was left standing for 1 hour. Evaporated off the ethanol and filtered off the off-white solid. Mass of title compound as a beige obtained on drying was 42 mg. δH (400 MHz, methanol-$d_4$) 2.69 (2H, t), 4.53 (2H, t), 7.17-7.18 (1H, m), 7.32-7.40 (3H, m), 7.46-4.49 (4H, m), 7.66 (1H, d), 7.75 (1H, d), 8.02 (1H, d), 8.53 (1H, dd), 8.63 (1H, d). MS (ES) $C_{26}H_{18}F_3N_3O_3$ requires 477; found 478 (MH$^+$).

Example 23

Sodium 3-(4-{5-[4-cyclohexyl-3-(trifluoromethyl)phenyl]-1,2,4-oxadiazol-3-yl}-1H-indol-1-yl)propanoate (E23)

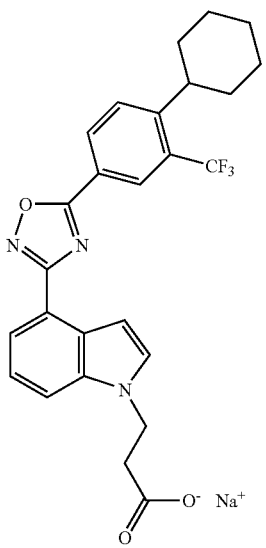

Ethyl 3-(4-{5-[4-cyclohexyl-3-(trifluoromethyl)phenyl]-1,2,4-oxadiazol-3-yl}-1H-indol-1-yl)propanoate (D69) (63 mg, 0.123 mmol) was dissolved in ethanol (8 ml) and sodium hydroxide (2M, 0.5 ml, 1.000 mmol) was added. The reaction was heated at 40° C. for 18 h. LCMS showed complete conversion to product. The reaction mixture was concentrated in vacuo and the white solid filtered off and washed with water. On filtration, much compound redissolved and passed through, so solid and filtrate were combined and separated between dichloromethane (10 mL) and 2M HCl (3 mL). The aqueous phase was extracted with further dichloromethane (10 mL). The organic phases were isolated by phase separator, combined and the solvent removed in vacuo. The solid was then dissolved in acetonitrile and water with addition of an equimolar amount of sodium hydroxide (2M, 53 μL) before the solution was freeze-dried to give the title compound (42 mg) as a white solid. δH (methanol-$d_4$, 400 MHz): 8.48 (1H, d), 8.43 (1H, dd), 7.98 (1H, dd), 7.86 (1H, d), 7.73 (1H, d), 7.46 (1H, d), 7.32 (1H, app. t), 7.15 (1H, dd), 4.52 (2H, t), 3.04 (1H, t), 2.69 (2H, t), 2.0-1.8 (5H, m), 1.63 (2H, dd), 1.53-1.37 (3H, m). MS (ES) $C_{26}H_{24}F_3N_3O_3$ requires 483; found 482 (M–H$^+$).

Example 24

Sodium 3-(4-{5-[4-[(1-methylethyl)oxy]-3-(trifluoromethyl)phenyl]-1,2,4-oxadiazol-3-yl}-1H-indol-1-yl)propanoate (E24)

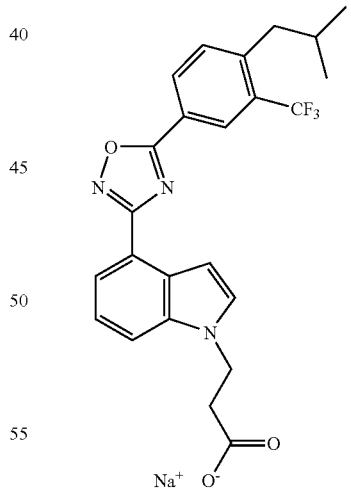

To a suspension of ethyl 3-(4-{5-[4-[(1-methylethyl)oxy]-3-(trifluoromethyl)phenyl]-1,2,4-oxadiazol-3-yl}-1H-indol-1-yl)propanoate (D72) (81 mg, 0.17 mmol) in ethanol (8 mL) was added aqueous sodium hydroxide (2M, 0.8 mL, 1.6 mmol) and the reaction heated to 50° C. to dissolve the reagents before heating at 40° C. for 1 h. The solvent was removed in vacuo and the residue partitioned between ethyl acetate (20 mL) and water (20 mL) and acidified with aqueous hydrochloric acid (2M). The aqueous phase was extracted with further ethyl acetate (2×20 mL) and the combined organic extracts dried (phase separator) and concentrated in vacuo. The solid was then dissolved in acetonitrile and water with addition of an equimolar amount of sodium hydroxide (2M) before the solution was freeze-dried to give the title compound (57 mg). δH (d$_6$-DMSO, 400 MHz): 8.44 (1H, dd), 8.35 (1H, d), 7.93 (1H, dd), 7.74 (1H, d), 7.65-7.54 (2H, m), 7.31 (1H, app. t), 7.00 (1H, dd) 4.99 (1H, septet), 4.38 (2H, t), 2.34 (2H, t), 1.36 (6H, d). MS (ES): $C_{23}H_{20}F_3N_3O_4$ requires 459; found 460 (MH$^+$).

The following examples were prepared by similar hydrolysis reactions to those described above. At least two equivalents of sodium hydroxide were used. The solvent was either ethanol or methanol. In some cases a cosolvent (dichloromethane or dioxane) was used to aid dissolution of the starting material. The reactions were carried out at a temperature between room temperature and 50° C. In some cases the some or all of the solvent was removed after the reaction was complete. The reactions were either worked up by partitioning between an organic and an aqueous layer or by filtering the solid product from the aqeuous solvent. In some cases the crude products were purified by trituration. Products were either isolated as the acid or the sodium salt.

| | Structure | precursor | Name | MS |
|---|---|---|---|---|
| E25 | 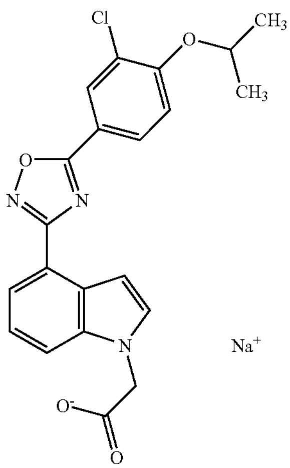 | D73 | sodium [4-(5-{3-chloro-4-[(1-methylethyl)oxy]phenyl}-1,2,4-oxadiazol-3-yl)-1H-indol-1-yl]acetate | 412 (MH$^+$ for $^{35}$Cl) |
| E26 | 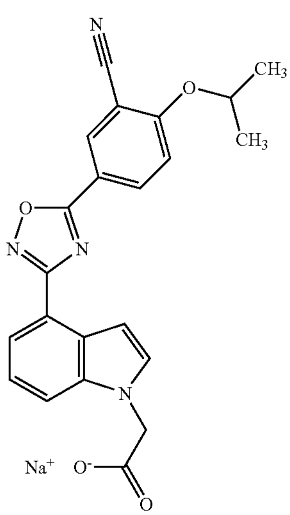 | D74 | sodium [4-(5-{3-cyano-4-[(1-methylethyl)oxy]phenyl}-1,2,4-oxadiazol-3-yl)-1H-indol-1-yl]acetate | 403 (MH$^+$) |

-continued

| | Structure | precursor | Name | MS |
|---|---|---|---|---|
| E27 | 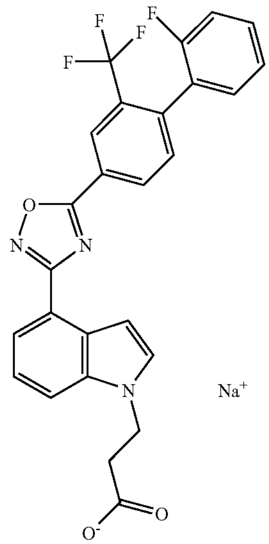 | D76 | sodium 3-(4-{5-[2'-fluoro-2-(trifluoromethyl)-4-biphenylyl]-1,2,4-oxadiazol-3-yl}-1H-indol-1-yl)propanoate | 496 (MH$^+$) |
| E28 | 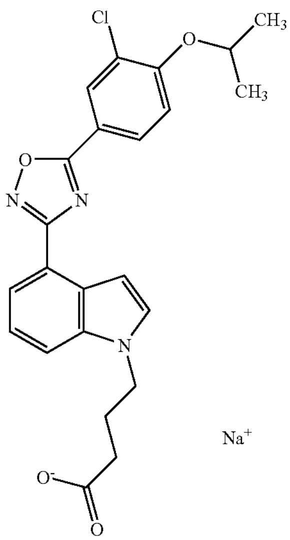 | D77 | sodium 4-[4-(5-{3-chloro-4-[(1-methylethyl)oxy]phenyl}-1,2,4-oxadiazol-3-yl)-1H-indol-1-yl]butanoate | 440 (MH$^+$ for $^{35}$Cl) |
| E29 | 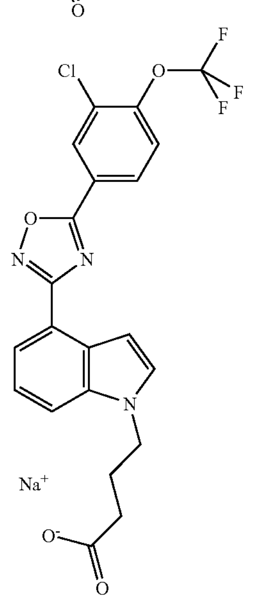 | D78 | sodium 4-[4-(5-{3-chloro-4-[(trifluoromethyl)oxy]phenyl}-1,2,4-oxadiazol-3-yl)-1H-indol-1-yl]butanoate | 466 (MH$^+$ for $^{35}$Cl) |

| | Structure | precursor | Name | MS |
|---|---|---|---|---|
| E30 | 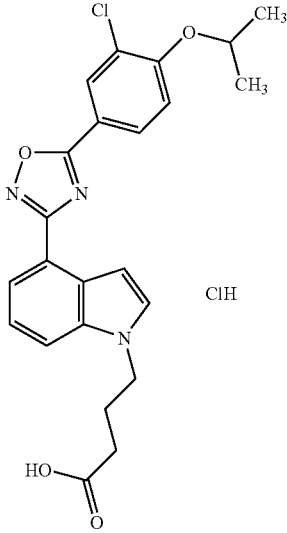 | D79 | 4-[4-(5-{5-chloro-6-[(1-methylethyl)oxy]-3-pyridinyl}-1,2,4-oxadiazol-3-yl)-1H-indol-1-yl]butanoic acid hydrochloride | 441 (MH$^+$ for $^{35}$Cl) |
| E31 | 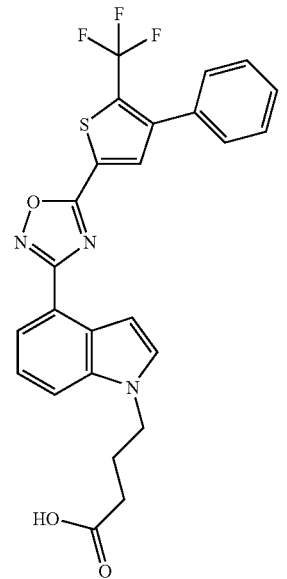 | D80 | 4-(4-{5-[4-phenyl-5-(trifluoromethyl)-2-thienyl]-1,2,4-oxadiazol-3-yl}-1H-indol-1-yl)butanoic acid | 498 (MH$^+$) |

| | Structure | precursor | Name | MS |
|---|---|---|---|---|
| E32 | 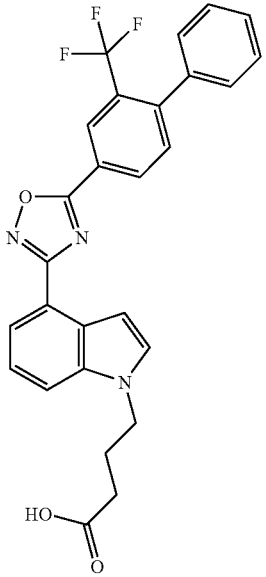 | D81 | 4-(4-{5-[2-(trifluoromethyl)-4-biphenylyl]-1,2,4-oxadiazol-3-yl}-1H-indol-1-yl)butanoic acid | 492 (MH$^+$) |
| E33 | 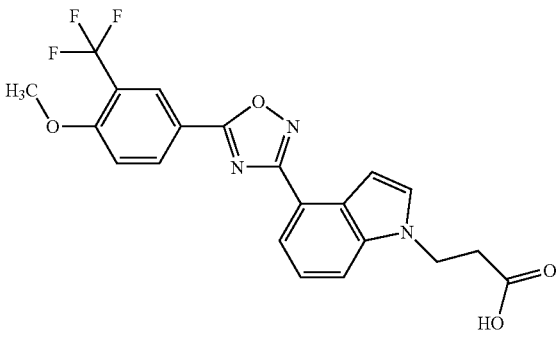 | D82 | 3-(4-{5-[4-(methyloxy)-3-(trifluoromethyl)phenyl]-1,2,4-oxadiazol-3-yl}-1H-indol-1-yl)propanoic acid | 432 (MH$^+$) |
| E34 | 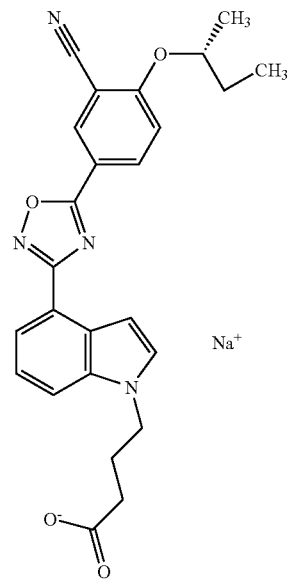 | D83 | sodium 4-{4-[5-(3-cyano-4-{[(1R)-1-methylpropyl]oxy}phenyl)-1,2,4-oxadiazol-3-yl]-1H-indol-1-yl}butanoate | 445 (MH$^+$) |

-continued

| | Structure | precursor | Name | MS |
|---|---|---|---|---|
| E35 | 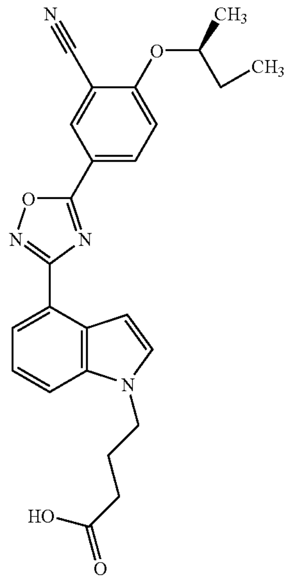 | D84 | 4-{4-[5-(3-cyano-4-{[(1S)-1-methylpropyl]oxy}phenyl)-1,2,4-oxadiazol-3-yl]-1H-indol-1-yl}butanoic acid | 445 (MH$^+$) |
| E36 | 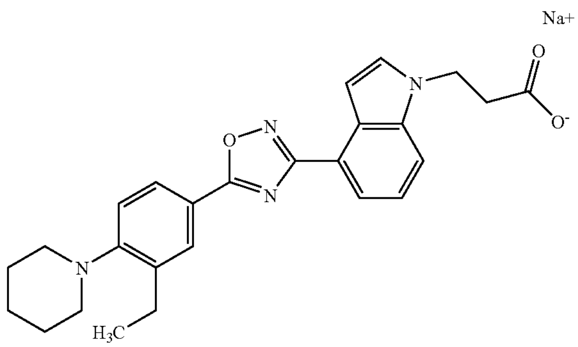 | D85 | sodium 3-(4-{5-[3-ethyl-4-(1-piperidinyl)phenyl]-1,2,4-oxadiazol-3-yl}-1H-indol-1-yl)propanoate | 445 (MH$^+$) |
| E37 | 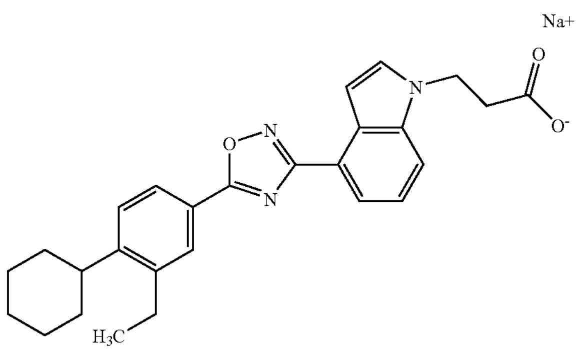 | D86 | sodium 3-{4-[5-(4-cyclohexyl-3-ethylphenyl)-1,2,4-oxadiazol-3-yl]-1H-indol-1-yl}propanoate | 444 (MH$^+$) |
| E38 | 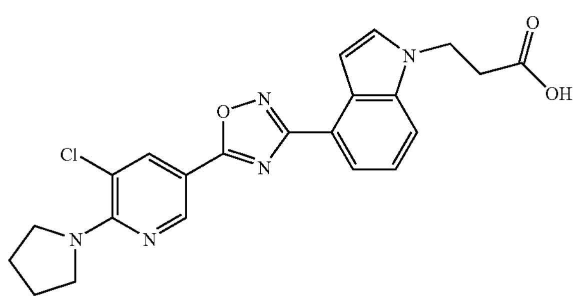 | D87 | 3-(4-{5-[5-chloro-6-(1-pyrrolidinyl)-3-pyridinyl]-1,2,4-oxadiazol-3-yl}-1H-indol-1-yl)propanoic acid | 438 (MH$^+$ for $^{35}$Cl) |

-continued

| | Structure | precursor | Name | MS |
|---|---|---|---|---|
| E39 | 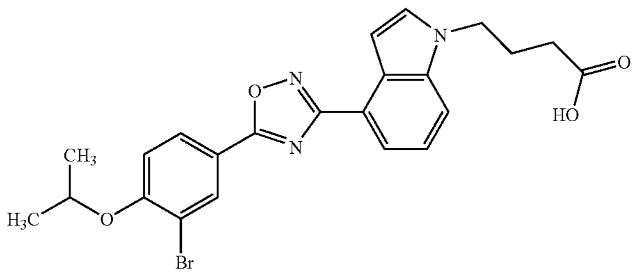 | D88 | 4-[4-(5-{3-bromo-4-[(1-methylethyl)oxy]phenyl}-1,2,4-oxadiazol-3-yl)-1H-indol-1-yl]butanoic acid | 484 (MH+ for 79Br) |
| E40 | 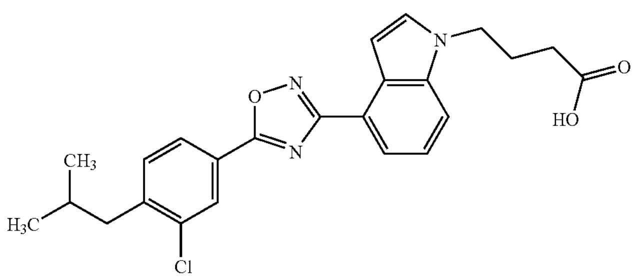 | D89 | 4-(4-{5-[3-chloro-4-(2-methylpropyl)phenyl]-1,2,4-oxadiazol-3-yl}-1H-indol-1-yl)butanoic acid | 438 (MH+ for 35Cl) |
| E41 | 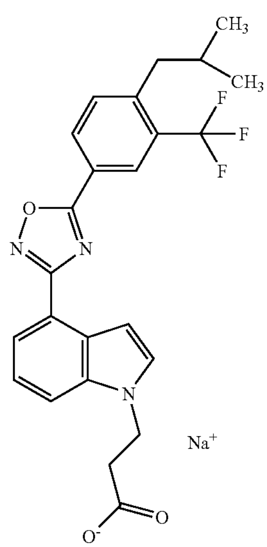 | D90 | sodium 3-(4-{5-[4-(2-methylpropyl)-3-(trifluoromethyl)phenyl]-1,2,4-oxadiazol-3-yl}-1H-indol-1-yl)propanoate | 456 (M − H+) |

116

-continued

| | Structure | precursor | Name | MS |
|---|---|---|---|---|
| E42 | 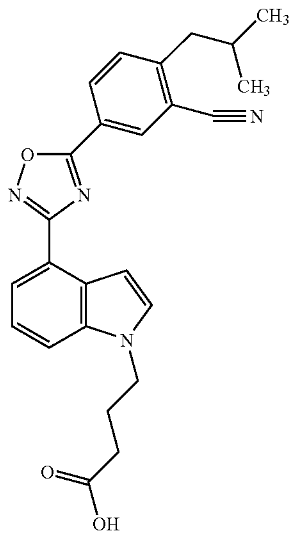 | D91 | 4-(4-{5-[3-cyano-4-(2-methylpropyl)phenyl]-1,2,4-oxadiazol-3-yl}-1H-indol-1-yl)butanoic acid | 429 (MH+) |
| E43 | 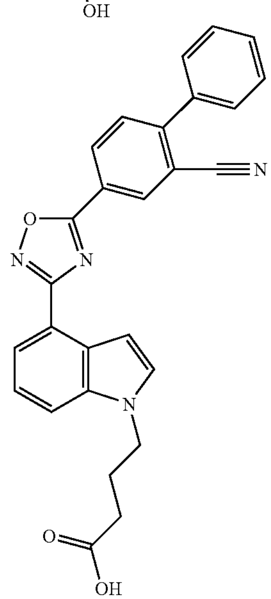 | D92 | 4-{4-[5-(2-cyano-4-biphenylyl)-1,2,4-oxadiazol-3-yl]-1H-indol-1-yl}butanoic acid | 447 (M − H+)− |

Example 44

3-(3-Chloro-4-{5-[4-phenyl-5-(trifluoromethyl)-2-thienyl]-1,2,4-oxadiazol-3-yl}-1H-indol-1-yl)propanoic acid (E44)

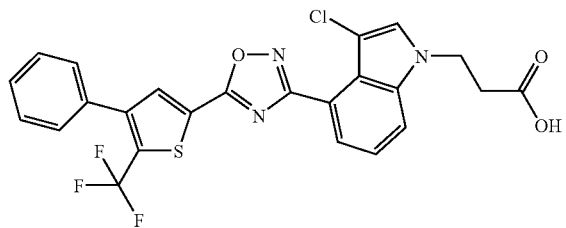

This material was prepared in a similar fashion to E5 (from D93) except that the alkylation step took 4.5 h in the microwave and the hydrolysis step was carried out at room temperature overnight. MS (ES): $C_{24}H_{15}ClF_3N_3O_3S$ requires 517; found 516 (M−H+).

Example 45

Sodium 3-[3-chloro-5-(5-{3-chloro-4-[(trifluoromethyl)oxy]phenyl}-1,2,4-oxadiazol-3-yl)-1H-indol-1-yl]propanoate(E45)

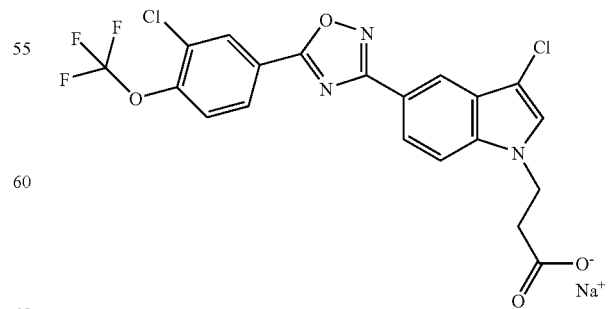

To ethyl 3-[3-chloro-5-(5-{3-chloro-4-[(trifluoromethyl)oxy]phenyl}-1,2,4-oxadiazol-3-yl)-1H-indol-1-yl]propanoate (D97) (150 mg, 2.9 mmol) in ethanol (10 ml) was added 2N NaOH (2 ml, 4 mmol) and the mixture heated at 50° C. for 30 minutes. Evaporated off the ethanol and filtered off the pale cream solid which had precipitated out of the remaining solution. Mass of title compound obtained on drying was 100 mg. δH (400 MHz, $d_6$-DMSO) 2.35 (2H, t), 4.35 (2H, t), 7.73-7.75 (2H, m), 7.86 (1H, d), 7.92 (1H, d), 8.22 (1H, s), 8.30-8.32 (1H, m), 8.49 (1H, d). MS (ES) $C_{20}H_{12}{}^{35}Cl_2F_3N_3O_4$ requires 485; found 486 (MH$^+$)

Example 46

Sodium 3-(3-chloro-5-{5-[3-chloro-4-(propyloxy)phenyl]-1,2,4-oxadiazol-3-yl}-1H-indol-1-yl)propanoate (E46)

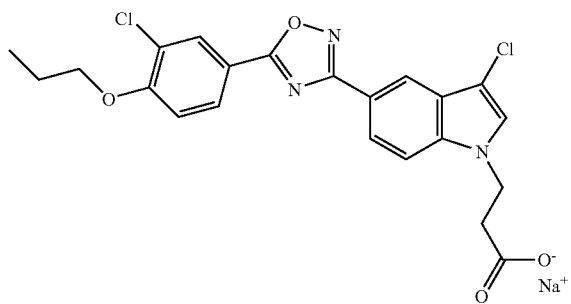

To ethyl 3-(3-chloro-5-{5-[3-chloro-4-(propyloxy)phenyl]-1,2,4-oxadiazol-3-yl}-1H-indol-1-yl)propanoate (D101) (120 mg, 2.5 mmol) in ethanol (10 ml) was added 2N NaOH (2 ml) and the mixture heated at 50° C. for 30 minutes. Evaporated off the ethanol and filtered off the white solid which had precipitated out of the remaining solution. Mass of title compound obtained on drying was 85 mg. δH (400 MHz, $d_6$-DMSO) 1.03 (3H, t), 1.77-1.86 (2H, m), 2.34 (2H, t), 4.17 (2H, t), 4.35 (2H, t), 7.40 (1H, d), 7.71-7.74 (2H, m), 7.91 (1H, d), 8.15 (1H, dd), 8.20-8.21 (2H, m). MS (ES) $C_{22}H_{19}{}^{35}Cl_2N_3O_4$ requires 459; found 460 (MH$^+$).

The following examples were prepared by a similar method to those described above, using 2-60 equivalents of sodium hydroxide (Table 8). The reactions were worked up by removing the ethanol and filtering the resultant solid or extracting the product into ethyl acetate. If required the products were purified by trituration with ether.

| | Structure | precursor | Name | MS |
|---|---|---|---|---|
| E47 | 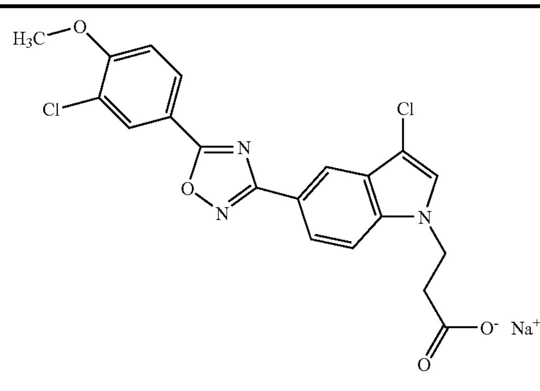 | D102 | sodium 3-(3-chloro-5-{5-[3-chloro-4-(methyloxy)phenyl]-1,2,4-oxadiazol-3-yl}-1H-indol-1-yl)propanoate | 430, 432 (M − H$^+$ for $^{35}Cl_2$, $^{35}Cl^{37}Cl$) |
| E48 | 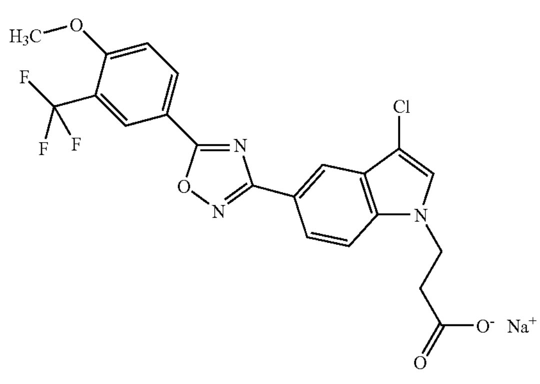 | D103 | sodium 3-(3-chloro-5-{5-[4-(methyloxy)-3-(trifluoromethyl)phenyl]-1,2,4-oxadiazol-3-yl}-1H-indol-1-yl)propanoate | 466 (MH$^+$ for $^{35}Cl$) |

| | Structure | precursor | Name | MS |
|---|---|---|---|---|
| E49 | 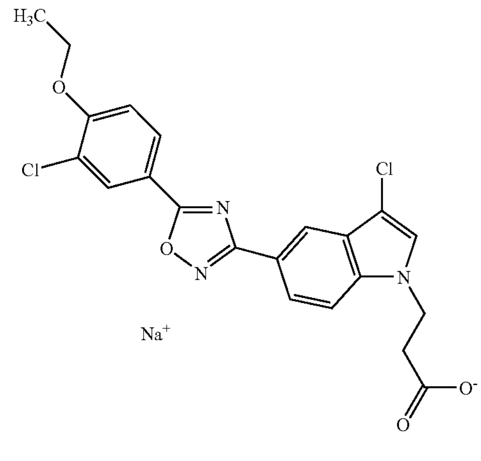 | D109 | sodium 3-(3-chloro-5-{5-[3-chloro-4-(ethyloxy)phenyl]-1,2,4-oxadiazol-3-yl}-1H-indol-1-yl)propanoate | 444, 446 (M − H$^+$ for $^{35}$Cl$_2$, $^{35}$Cl$^{37}$Cl) |
| E50 | 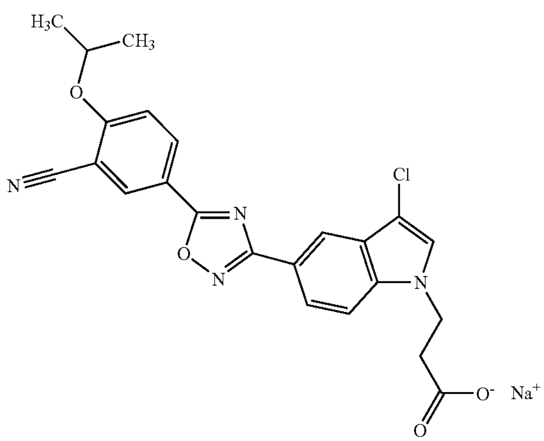 | D104 | sodium 3-[3-chloro-5-(5-{3-cyano-4-[(1-methylethyl)oxy]phenyl}-1,2,4-oxadiazol-3-yl)-1H-indol-1-yl]propanoate | 451 (MH$^+$ for $^{35}$Cl) |
| E51 | 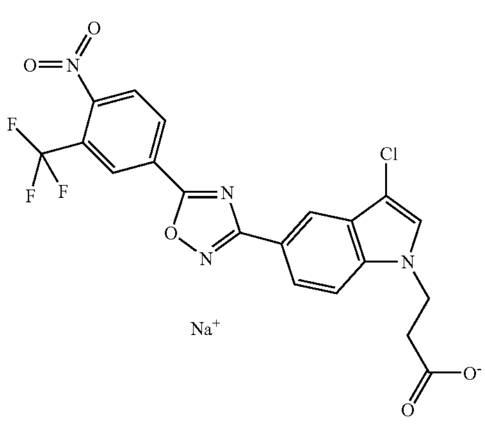 | D105 | sodium 3-(3-chloro-5-{5-[4-nitro-3-(trifluoromethyl)phenyl]-1,2,4-oxadiazol-3-yl}-1H-indol-1-yl)propanoate | 478, 480 in ES$^-$ |

Example 53

Sodium 3-(3-chloro-5-{5-[6-(methyloxy)-3-biphenylyl]-1,2,4-oxadiazol-3-yl}-1H-indol-1-yl)propanoate (E53)

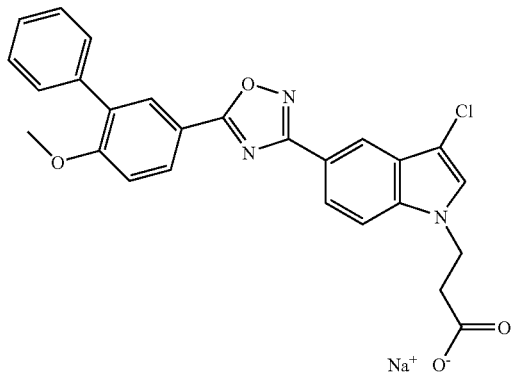

Ethyl 3-(3-chloro-5-{5-[6-(methyloxy)-3-biphenylyl]-1,2,4-oxadiazol-3-yl}-1H-indol-1-yl)propanoate (D107) (90 mg, 0.18 mmol) was heated in ethanol (10 ml) to give a clear solution. This solution was treated with 2N sodium hydroxide (3 ml, 6 mmol) and stirred at 50° C. for 30 minutes. Evaporated off the ethanol and filtered off the white solid that precipitated out of solution, washing the solid with a small amount of water and ether. Stirred solid in a small amount of acetone for 1 hour, filtered, washed with a small amount of ether and dried to yield the title compound as 45 mg of white solid. δH (400 MHz, $d_6$-DMSO) 2.34 (2H, t), 3.91 (3H, s), 4.34 (2H, t), 7.41-7.46 (2H, m), 7.48-7.50 (2H, m), 7.57-7.59 (2H, m), 7.63-7.66 (2H, m), 7.80 (1H, d), 8.10 (1H, d), 8.10-8.25 (2H, m). MS (ES) $C_{26}H_{20}{}^{35}ClN_3O_4$ requires 473; found 474 (MH$^+$).

Example 54

3-(5-{5-[6-(Trifluoromethyl)-3-biphenylyl]-1,2,4-oxadiazol-3-yl}-1H-indol-1-yl)propanoic acid (E54)

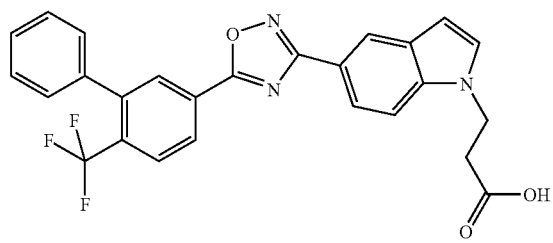

This material was prepared by a similar method to prepare E53. The solvent was a mixture of ethanol and 1,4-dioxane and 0.071 ml of 2M aq. NaOH was used to hydrolyse 51 mg of D113. MS (ES) $C_{26}H_{18}F_3N_3O_3$ requires 477; found 476 (M–H$^+$).

GTPγS Binding Assay

Rat basophilic eukaemia cells (RBL) stably expressing S1P1 receptor were grown to 80% confluency before being harvested into 10 ml Phospho-Buffered Saline (PBS) and centrifuged at 1200 rpm for 5 minutes. After removal of the supernatant, the pellet was re-suspended and homogenised in 20 volumes assay buffer (20 mM HEPES pH 7.4, 100 mM NaCl, 10 mM MgCl$_2$.6H$_2$O, 10 μM GDP Saponin 10 μg/ml). The membrane suspension was further centrifuged for 20 minutes at 20,000 rpm re-homogenised and spun again. Following the second centrifugation the pellet was re-suspended in an appropriate volume (1 ml for each flask of cells) and assayed for protein concentration.

Concentrated stock of S1P was sonicated before serial dilutions were prepared from a starting concentration of $10^{-5}$ M. Diluted membranes (10 μg/well) were incubated with various concentrations of S1P and 0.3 nM $^{35}$S-GTPγS (NEN; specific activity 1250 Ci/mmol) in 96 deep well plates. Binding was performed at 30° C. for 45 minutes and terminated by harvesting the membranes onto GF/B filter plates using a Packard Universal Harvester. After drying the plates for 45 minutes, 50 μl of Microscint 0 was added to each well and binding measured on a Topcount NXT (Perkin Elmer). Data was analysed using Graphpad Prism 4 and expressed as percentage stimulation above basal. EC50 values were defined as the concentration of agonist required to give 50% of the maximal stimulation.

Membrane Preparation (Alternative Method)

For membrane preparations all steps were performed at 4° C. Rat hepatoma cells stably expressing the human S1P1 receptor or Rat Basophilic Leukemia cells (RBL) stably expressing human S1P3 receptor were grown to 80% confluency before being harvested into 10 ml Phospho-Buffered Saline (PBS) and centrifuged at 1200 rpm for 5 minutes. After removal of the supernatant, the pellet was re-suspended and cells were homogenised within a glass Waring blender for 2 bursts of 15 secs in 200 mls of buffer (50 mM HEPES, 1 mM leupeptin, 25 μg/ml bacitracin, 1 mM EDTA, 1 mM PMSF, 2 μM pepstatin A). The blender was plunged into ice for 5 mins after the first burst and 10-40 mins after the final burst to allow foam to dissipate. The material was then spun at 500 g for 20 mins and the supernatant spun for 36 mins at 48,000 g. The pellet was resuspended in the same buffer as above but without PMSF and pepstatin A. The material was then forced through a 0.6 mm needle, made up to the required volume, (usually ×4 the volume of the original cell pellet), aliquoted and stored frozen at –80° C.

S1P1 GTPγS Assay (Alternative Method)

Human S1P1 rat hepatoma membranes (1.5 μg/well) were adhered to a wheatgerm agglutinin (WGA)-coated scintillation proximity assay (SPA) beads (0.125 mg/well) in assay buffer (HEPES 20 mM, MgCl$_2$ 10 mM, NaCl 100 mM and pH adjusted to 7.4 using KOH 5M, GDP 10 μM FAC (final assay concentration) and saponin 90 μm/ml FAC was also added).

After 30 minutes pre-coupling on ice the bead and membrane suspension was dispensed into a white Greiner polypropylene LV384-well plate (5 μl/well), containing 0.1 μl of the compound. 5 μl/well [$^{35}$S]-GTPγS (0.5 nM final radioligand conc) made up in assay buffer was then added to agonist plates. The final assay cocktail (10.1 μl) was then centrifuged at 1000 rpm for 5 minutes then read immediately on a Viewlux reader.

All test compounds were dissolved in DMSO at a concentration of 10 mM and were prepared in 100% DMSO using a 1 in 4 dilution step to provide 11 point dose response curves. The dilutions were transferred to the assay plates ensuring that the DMSO concentration was constant across the plate for all assays.

All data was normalized to the mean of 16 high and 16 low control wells on each plate. A four parameter curve fit was then applied.

Exemplified compounds of the invention that were tested in this assay had a pEC50>5.

S1P3

S1P3 membranes from rat basophilic leukemia cells (RBL-2H3)(1.5 µg/well) were adhered to WGA-coated SPA beads (0.125 mg/well) in assay buffer (HEPES 20 mM, $MgCl_2$ 3 mM, NaCl 100 mM and pH adjusted to 7.4 using KOH 5M), GDP 10 µM FAC and saponin 90 µg/ml FAC was also added).

After 30 minutes pre-coupling on ice the bead and membrane suspension was dispensed into a white Greiner polypropylene LV384-well plate (5 µl/well), containing 0.1 µl of the compound. 5 µl/well [$^{35}$S]-GTPγS (0.5 nM final radio-ligand conc) made up in assay buffer was then added to agonist plates. The final assay cocktail (10.1 µl) was centrifuged at 1000 rpm for 5 minutes then read immediately on a Viewlux reader.

All test compounds were dissolved in DMSO at a concentration of 10 mM and were prepared in 100% DMSO using a 1 in 4 dilution step to provide 11 point dose response curves. The dilutions were transferred to the assay plates ensuring that the DMSO concentration was constant across the plate for all assays.

All data was normalized to the mean of 16 high and 16 low control wells on each plate. A four parameter curve fit was then applied.

Exemplified compounds tested in this assay had a pEC50<6, many had a pEC50<5.

Yeast Assay

Yeast (*Saccharomyces cerevisiae*) cells expressing the human S1P1 receptor were generated by integration of an expression cassette into the ura3 chromosomal locus of yeast strain MMY23. This cassette consisted of DNA sequence encoding the human S1P1 receptor flanked by the yeast GPD promoter to the 5' end of S1P1 and a yeast transcriptional terminator sequence to the 3' end of S1P1. MMY23 expresses a yeast/mammalian chimeric G-protein alpha subunit in which the C-terminal 5 amino acids of Gpa1 are replaced with the C-terminal 5 amino acids of human Gαi1/2 (as described in Brown et al. (2000), *Yeast* 16:11-22). Cells were grown at 30° C. in liquid Synthetic Complete (SC) yeast media (Guthrie and Fink (1991), Methods in Enzymology, Vol. 194) lacking uracil, tryptophan, adenine and leucine to late logarithmic phase (approximately 6 $OD_{600}$/ml).

Agonists were prepared as 10 mM solutions in DMSO. $EC_{50}$ values (the concentration required to produce 50% maximal response) were estimated using 4 fold dilutions (BiomekFX, Beckman) into DMSO. Agonist solutions in DMSO (1% final assay volume) were transferred into black microtitre plates from Greiner (384-well). Cells were suspended at a density of 0.2 $OD_{600}$/ml in SC media lacking histidine, uracil, tryptophan, adenine and leucine and supplemented with 0.1 mM 3-aminotriazole, 0.1M sodium phosphate pH 7.0, and 10 µM fluorescein di-β-D-glucopyranoside (FDGlu). This mixture (50 ul per well) was added to agonist in the assay plates (Multidrop 384, Labsystems). After incubation at 30° C. for 24 hours, fluorescence resulting from degradation of FDGlu to fluorescein due to exoglucanase, an endogenous yeast enzyme produced during agonist-stimulated cell growth, was determined using a fluorescence microtitre plate reader (Tecan Spectrofluor or LJL Analyst excitation wavelength: 485 nm; emission wavelength: 535 nm). Fluorescence was plotted against compound concentration and iteratively curve fitted using a four parameter fit to generate a concentration effect value. Efficacy ($E_{max}$) was calculated from the equation $E_{max} = Max_{[compound\ X]} - Min_{[compound\ X]}/Max_{[S1P]} - Min_{[S1P]} \times 100\%$ where $Max_{[compound\ X]}$ and $Min_{[compound\ X]}$ are the fitted maximum and minimum respectively from the concentration effect curve for compound X, and $Max_{[S1P]}$ and $Min_{[S1P]}$ are the fitted maximum and minimum respectively from the concentration effect curve for Sphingosine-1-Phosphate (available from Sigma). Equieffective molar ratio (EMR) values were calculated from the equation $EMR = EC_{50[compound\ X]}/EC_{50[S1P]}$ Where $EC_{50\ [compound\ X]}$ is the $EC_{50}$ of compound X and $EC_{50\ [S1P]}$ is the $EC_{50}$ of S1P.

Where tested, exemplified compounds of the invention had a pEC50>4.5 in the yeast assay.

The invention claimed is:

1. 4-[4-(5-{5-chloro-6-[(1-methylethyl)oxy]-3-pyridinyl}-1,2,4-oxadiazol-3-yl)-1H-indol-1-yl]butanoic acid; and pharmaceutically acceptable salts thereof.

2. A pharmaceutical composition comprising a compound of claim 1 and one or more pharmaceutically-acceptable excipients.

3. 4-[4-(5- {5-chloro-6-[(1-methylethyl)oxy]-3-pyridinyl}-1,2,4-oxadiazol-3-yl)-1H-indol-1-yl]butanoic acid hydrochloride.

4. A pharmaceutical composition comprising a compound of claim 3 and one or more pharmaceutically-acceptable excipients.

* * * * *